US006436928B1

(12) United States Patent
Shih et al.

(10) Patent No.: US 6,436,928 B1
(45) Date of Patent: Aug. 20, 2002

(54) SELECTIVE NEUROKININ ANTAGONISTS

(75) Inventors: Neng-Yang Shih, North Caldwell; Ho-Jane Shue, Pine Brook; Gregory A. Reichard, Morris Plains; Sunil Paliwal, Scotch Plains; David J. Blythin, North Caldwell; John J. Piwinski, Clinton Township; Dong Xiao, Scotch Plains; Xiao Chen, Edison, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/737,036

(22) Filed: Dec. 14, 2000

Related U.S. Application Data

(60) Provisional application No. 60/172,489, filed on Dec. 17, 1999.

(51) Int. Cl.[7] .................. A61K 31/4166; C07D 233/02; C07D 233/32
(52) U.S. Cl. .................... 514/227.8; 514/396; 514/399; 514/400; 548/316.5; 548/323.5
(58) Field of Search .............................. 514/396, 227.8, 514/399, 400; 548/316.4, 323.5

(56) References Cited

U.S. PATENT DOCUMENTS

| 5,760,018 A | * | 6/1998 | Baker et al. .................. 514/63 |
| 5,952,330 A | | 9/1999 | Rupniak .................. 514/234.5 |
| 6,162,805 A | | 12/2000 | Hefti ....................... 514/236.2 |

FOREIGN PATENT DOCUMENTS

| EP | 0 790 248 | | 8/1997 |
| FR | 5677 | * | 2/1968 |
| WO | WO 94/10165 | | 5/1994 |
| WO | WO 94/13639 | | 6/1994 |

OTHER PUBLICATIONS

Kramer et al, *Science*, 281 (1998), p. 1640–1645.
Stevenson et al, *J. Med. Chem.*, 41 (1998), p. 4623–4635.
Peter Ward et al., *J. Med. Chem.*, 38 (1995), p. 4985–4992.
Raquel M. Teixeira, *European Journal of Pharmacology*, 311 (1996) p. 7–14.
Harrison et al, *Bioorganic & Medicinal Chem. Let.*, 4, 23 (1994), p. 2733–2734.
Oh, et al, Bull. *Korean Chem. Soc.*, 9, 4 (1988), p. 231–235.
Knabe et al, *Pharmazie*, 52 (1997), p. 912–919.
Schulte, et al, *Eur. J. Med. Chem.—Chimica Therapeutica*, 13 (1978), p. 25–31.
Wu et al, *Tetrahedron*, 56 (2000), p. 6279–6290.

* cited by examiner

Primary Examiner—Mukund J. Shah
Assistant Examiner—Sudhaker B. Patel
(74) Attorney, Agent, or Firm—Anita W. Magatti

(57) ABSTRACT

A compound represented by the structural formula

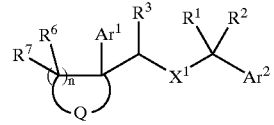

I or a pharmaceutically acceptable salt thereof, wherein
$Ar^1$ and $Ar^2$ are optionally substituted heteroaryl or optionally substituted phenyl;
$X^1$ is —O—, —$SO_{0-2}$—, —$NR^{12}$—, —$NCOR^{12}$— or —$NR^{12}SO_2R^{15}$;

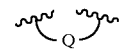

is

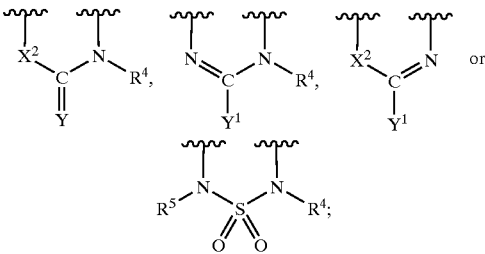

$X^2$ is —O—, —S— or optionally substituted nitrogen;
Y is =O, =S or =$NR^{11}$;
$Y^1$ is H, alkyl, —$NR^{17}R^{13}$, —$SCH_3$, $R^{19}$-aryl $(CH_2)_{n6}$—, $R^{19}$-heteroaryl-$(CH_2)_{n6}$—, —$(CH_2)_{n6}$-heterocycloalkyl, -alkyl-NH—C(O)O-alkyl or —NHC(O)$R^{15}$;
$R^1$, $R^2$, $R^3$ and $R^7$ are H, alkyl, OH-alkyl, cycloalkyl, —$CHF_2$, —$CH_2F$ or —$CF_3$; or $R^1$ and $R^2$ form an alkylene ring; or $R^1$ and $R^2$ together are =O;
$R^6$ is H, alkyl, —$OR^{13}$ or —$SR^{12}$;
and the remaining variables are as defined in the specification, is disclosed, as well as a pharmaceutical compositions comprising said compound, methods of using said compound as a neurokinin antagonist, and the combination of said compounds with a selective serotonin reuptake inhibitor.

23 Claims, No Drawings

SELECTIVE NEUROKININ ANTAGONISTS

CROSS REFERENCE TO RELATED APPLICATIONS

This application claims the benefit of U.S. Provisional Application 60/172,489, filed Dec. 17, 1999.

BACKGROUND OF THE INVENTION

The present invention relates to a genus of substituted cyclic ureas and derivatives thereof useful as antagonists of tachykinin receptors, in particular as antagonists of the neuropeptides neurokinin-1 receptor ($NK_1$).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example respiratory diseases such as chronic lung disease, bronchitis, pneumonia, asthma, allergy, cough, bronchospasm; inflammatory diseases such as arthritis and psoriasis; skin disorders such as atopic dermatitis and contact dermatitis; ophthalmological disorders such as retinitis, ocular hypertension and cataracts; addictions such as alcohol dependence and psychoactive substance abuse; stress related disorders such as post tramautic stress disorder; obsessive/compulsive disorders; eating disorders such as bulemia, anorexia nervosa and binge eating disorders; mania; premenstrual syndrome; central nervous system conditions such as anxiety, general anxiety disorder, panic disorder, phobias, bipolar disorders, migraine, epilepsy, nociception, emesis, depression, psychosis, schizophrenia, Alzheimer's disease, AIDs related dementia and Towne's disease; gastrointestinal disorders such as Crohn's disease and colitis; nausea; bladder disorders; atherosclerosis; fibrosing disorders; obesity; Type II diabetes; pain related disorders such as neuropathic pain, post-operative pain, headache and chronic pain syndromes; and genitourinary disorders such as interstitial cystitis and urinary incontinence.

In particular, $NK_1$ receptors have been reported to be involved in microvascular leakage and mucus secretion, making $NK_1$ receptor antagonists especially useful in the treatment and prevention of asthma, emesis, nausea, depression, anxiety, cough, pain and migraine.

SUMMARY OF THE INVENTION

Compounds of the present invention are represented by the formula I

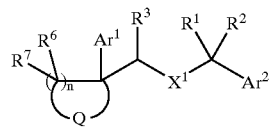

I or a pharmaceutically acceptable salt thereof, wherein $Ar^1$ and $Ar^2$ are independently selected from the group consisting of $R^{17}$-heteroaryl and

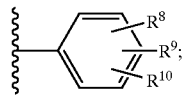

$X^1$ is —O—, —S—, —SO—, —SO_2—, —$NR^{12}$—, —$N(COR^{12})$— or is $N(SO^2R^{15})$—;

$R^1$, $R^2$, $R^3$ and $R^7$ are each independently selected from the group consisting of H, $C_1$–$C_6$ alkyl, hydroxy ($C_1$–$C_3$)alkyl, $C_3$–$C_8$ cycloalkyl, —$CH_2F$, —$CHF_2$ and —$CF_3$; or $R^1$ and $R^2$, together with the carbon to which they are attached, form a $C_3$–$C_6$ alkylene ring; or, when $X^1$ is —O—, —S— or —$NR^{12}$—, $R^1$ and $R^2$ together are =O;

each $R^6$ is independently selected from H, $C_1$–$C_6$ alkyl, —$OR^{13}$ or —$SR^{12}$;

n is 1–4, if n is greater than 1, then $R^6$ and $R^7$ can be the same or different on each carbon;

is selected from the group consisting of

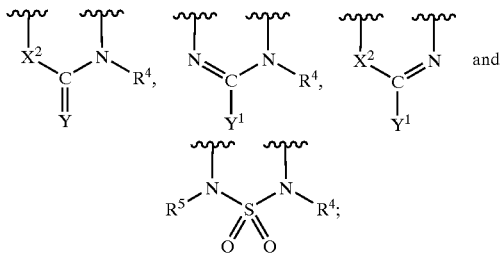

$X^2$ is —O—, —S— or —$NR^5$—;
Y is =O, =S or =$NR^{11}$;
$Y^1$ is H, $C_1$–$C_6$ alkyl, —$NR^{17}R^{13}$, —$SCH_3$, $R^{19}$-aryl $(CH_2)_{n6}$—, $R^{19}$-heteroaryl-$(CH_2)_{n6}$—, —$(CH_2)_{n6}$-heterocycloalkyl, —$(C_1$–$C_3$)alkyl-NH—C(O)O $(C_1$–$C_6)$alkyl or —NHC(O)$R^{15}$;
$R^5$ is H or —$(CH_2)_{n1}$—G, wherein $n_1$ is 0–5, G is H, —$CF_3$, —$CHF_2$, —$CH_2F$, —OH, —O— ($C_1$–$C_6$alkyl), —$SO_2R^{13}$, —O—($C_3$–$C_8$ cycloalkyl), —$NR^{13}R^{14}$, —$SO_2NR^{13}R^{14}$, —$NR^{13}SO_2R^{15}$, —$NR^{13}COR^{12}$, —$NR^{12}(CONR^{13}R^{14})$, —$CONR^{13}R^{14}$, —$COOR^{12}$, $C_3$–$C_8$ cycloalkyl, $R^{19}$-aryl, $R^{19}$-heteroaryl.

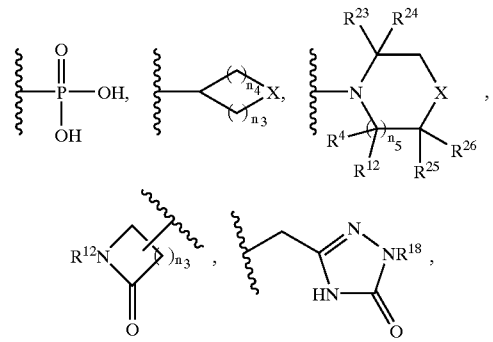

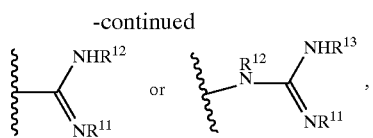

or when $n_1$ is 0, $R^5$ can also be —C(O)$R^{13}$; or —C(S)$R^{13}$; provided that G is not H when n1=0;

X is —$NR^{20}$—, —N(CON$R^{13}R^{14}$)—, —N(C$O_2R^{13}$)—, —N(S$O_2R^{15}$)—, —N(CO$R^{12}$)—, N(S$O_2$NH$R^{13}$)—, —O—, —S—, —SO—, —S$O_2$—, —C$F_2$—, —C$H_2$— or —C$R^{12}$F—;

$R^8$, $R^9$ and $R^{10}$ are independently selected from the group consisting of H, $C_1$–$C_6$ alkyl, $C_3$–$C_8$ cycloalkyl, —O$R^{12}$, halogen, —CN, —N$O_2$, —C$F_3$, —CH$F_2$, —C$H_2$F, —OC$F_3$, —OCH$F_2$, —OC$H_2$F, —COO$R^{12}$, —CON$R^{21}R^{22}$, —N$R^{21}$CO$R^{12}$, —N$R^{21}$C$O_2R^{15}$, —N$R^{21}$CON$R^{21}R^{22}$, —N$R^{21}$S$O_2R^{15}$, —N$R^{21}R^{22}$, —S$O_2$N$R^{21}R^{22}$, —S(O)$_{n5}R^{15}$, $R^{16}$-aryl and $R^{19}$-heteroaryl;

$R^{11}$ is H, $C_1$–$C_6$ alkyl, $C_3$–$C_8$ cycloalkyl, —N$O_2$, —CN, OH, —O$R^{12}$, —O(C$H_2$)$_{n6}R^{12}$, —($C_1$–$C_3$) alkyl-C(O)NH$R^{12}$, $R^{19}$-aryl(C$H_2$)$_{n6}$— or $R^{19}$-heteroaryl(C$H_2$)$_{n6}$—;

$R^4$ and $R^{12}$ are each independently selected from the group consisting of H, $C_1$–$C_6$ alkyl and $C_3$–$C_8$ cycloalkyl;

$R^{13}$ and $R^{14}$ are independently selected from the group consisting of H, $C_1$–$C_6$ alkyl, $C_3$–$C_8$ cycloalkyl, $R^{19}$-aryl (C$H_2$)$_{n6}$— or $R^{19}$-heteroaryl(C$H_2$)$_{n6}$—; or $R^{13}$ and $R^{14}$ together are $C_3$–$C_6$ alkylene and with the nitrogen to which they are attached form a 4–7 membered ring, or one of the carbon atoms in the alklyene chain formed by $R^{13}$ and $R^{14}$ is replaced by a heteroatom selected from the group consisting of —O—, —S— and —N$R^{12}$—;

$R^{15}$ is $C_1$–$C_6$ alkyl, $C_3$–$C_8$ cycloalkyl or —C$F_3$;

$R^{16}$ is 1 to 3 substituents independently selected from the group consisting of H, $C_1$–$C_6$ alkyl, $C_3$–$C_8$ cycloalkyl, $C_1$–$C_6$ alkoxy, halogen and —C$F_3$;

$R^{17}$ is H, $C_1$–$C_6$ alkyl, $C_3$–$C_8$ cycloalkyl, —COO$R^{12}$, —CON$R^{21}R^{22}$, —N$R^{21}R^{22}$, —N$R^{21}$CO$R^{12}$, —N$R^{21}$C$O_2R^{12}$, —N$R^{21}$CON$R^{21}R^{22}$, —N$R^{21}$S$O_2R^{15}$ or —S(O)$_{n5}R^{15}$;

$R^{18}$ is H, $C_1$–$C_6$ alkyl or —P(O)(OH)$_2$;

$R^{19}$ is 1 to 3 substituents independently selected from the group consisting of H, $C_1$–$C_6$ alkyl, $C_3$–$C_8$ cycloalkyl, —OH, halogen, —CN, —N$O_2$, —C$F_3$, —CH$F_2$, —C$H_2$F, —OC$F_3$, —OCH$F_2$, —OC$H_2$F, —O—($C_1$–$C_6$ alkyl), —O—($C_3$–$C_8$ cycloalkyl), —COO$R^{12}$, —CON$R^{21}R^{22}$, —N$R^{21}R^{22}$, —N$R^{21}$CO$R^{12}$, —N$R^{21}$C$O_2R^{12}$, —N$R^{21}$CON$R^{21}R^{22}$, —N$R^{21}$S$O_2R^{15}$ and —S(O)$_{n5}R^{15}$;

$R^{20}$ is H, $C_1$–$C_6$ alkyl, $C_3$–$C_8$ cycloalkyl or —(C$H_2$)$_{n6}$-heterocycloalkyl;

$R^{21}$ and $R^{22}$ are independently selected from the group consisting of H, $C_1$–$C_6$ alkyl, $C_3$–$C_8$ cycloalkyl and benzyl; or $R^{21}$ and $R^{22}$ together are $C_3$–$C_6$ alkylene and with the nitrogen to which they are attached form a 4–7 membered ring, or one of the carbon atoms in the alklyene chain formed by $R^{21}$ and $R^{22}$ is replaced by a heteroatom selected from the group consisting of —O—, —S— and —N$R^{12}$—;

$R^{23}$, $R^{24}$, $R^{25}$ and $R^{26}$ are H, $C_1$–$C_6$ alkyl and can be together as =O; when $n_5$=0, and $R^{25}$ and $R^{26}$=H, X is not O, N, S;

$n_3$ and $n_4$ are independently 1–5, provided that the sum of $n_3$ and $n_4$ is 2–6;
$n_5$ is independently 0–2;
$n_6$ is independently 0–3; and
q and r are independently 1 or 2.

Preferred are compounds of formula I wherein $R^4$ and $R^7$ are each H. Also preferred are compounds of formula I wherein $R^1$ and $R^3$ are each H. Also preferred are compounds of formula I wherein $R^1$, $R^3$, $R^4$ and $R^7$ are each H. $R^6$ is preferably H or —OH. Preferably, $X^1$ is —O— or —N$R^{12}$—. A$r^1$ and A$r^2$ are each preferably $R^8$, $R^9$, $R^{10}$-phenyl, wherein $R^8$, $R^9$ and $R^{10}$ are independently selected. Y is preferably =O, and n is preferably 1 or 2. When Y is =O, $X^2$ is preferably —N$R^5$—. More preferred are compounds of formula I wherein Q is —$X^2$—C(=Y)—N$R^4$— (i.e., the first structure shown in the definition of Q), $R^1$, $R^3$, $R^4$ and $R^7$ are each H; $R^6$ is H or —OH; $X^1$ is —O— or —N$R^{12}$—; A$r^1$ and A$r^2$ are each $R^8$,$R^9$,$R^{10}$-phenyl; Y is =O and $X^2$ is —N$R^5$—; n is 1 or 2; $R^5$ is H or —(C$H_2$)$_{n1}$—G, G is not H when $n_1$=0; $R^{19}$-aryl or $R^{19}$-heteroaryl. Most preferred are compounds of formula I wherein $R^5$is H.

This invention also relates to the use of a compound of formula I in the treatment of, for example, respiratory diseases such as chronic lung disease, bronchitis, pneumonia, asthma, allergy, cough, bronchospasm; inflammatory diseases such as arthritis and psoriasis; skin disorders such as atopic dermatitis and contact dermatitis; ophthalmalogical disorders such as retinitis, ocular hypertension and cataracts; addictions such as alcohol dependence and psychoactive substance abuse; stress related disorders such as post tramautic stress disorder; obsessive/compulsive disorders; eating disorders such as bulemia, anorexia nervosa and binge eating disorders; mania; premenstrual syndrome; central nervous system conditions such as anxiety, general anxiety disorder, panic disorder, phobias, bipolar disorders, migraine, epilepsy, nociception, emesis, depression, psychosis, schizophrenia, Alzheimer's disease, AIDs related dementia and Towne's disease; gastrointestinal disorders such as Crohn's disease and colitis; nausea; bladder disorders; atherosclerosis; fibrosing disorders; obesity; Type II diabetes; pain related disorders such as neuropathic pain, post-operative pain, headache and chronic pain syndromes; and genitourinary disorders such as interstitial cystitis and urinary incontinence. The treatment of mammals, both human and non-human, is contemplated.

Further, the invention relates to a method for antagonizing the effect of Substance P at its receptor site or for the blockade of neurokinin-1 receptors in a mammal, comprising administering an amount of a compound of formula I effective to antagonize the effect of Substance P at its receptor site in a mammal in need of such treatment.

In another aspect, the invention relates to a pharmaceutical composition comprising a compound of formula I in a pharmaceutically acceptable carrier. The invention also relates to the use of said pharmaceutical composition in the treatment of the mammalian disease states listed above.

The compounds of this invention can be combined with a selective serotonin reuptake inhibitor (SSRI) (i.e., the compounds of this invention can be combined with an SSRI in a pharmaceutical composition, or the compounds of this invention can be administered with an SSRI.

Numerous chemical substances are known to alter the synaptic availability of serotonin through their inhibition of presynaptic reaccumulation of neuronally released serotonin. Representative SSRIs include, without limitation; fluoxetine, fluvoxamine, paroxetine and sertaline, and pharmaceutically acceptable salts thereof. Other compounds can readily be evaluated to determine their ability to selectively inhibit serotonin reuptake.

In another aspect, the invention relates to a method of treating the above diseases and disorders comprising administering an effective amount of an NK1 antagonist of formula I in combination with an SSRI described above.

In another aspect, the invention relates to a method of treating the above diseases and disorders comprising administering an effective amount of an NK1 antagonist of formula I in combination with an SSRI selected from: fluoxetine, fluvoxamine, paroxetine and sertaline, and pharmaceutically acceptable salts thereof.

In another aspect, the invention relates to a method of treating emesis, depression, anxiety, and cough comprising administering an effective amount of an NK1 antagonist of formula I in combination with an SSRI described above.

In the methods of this invention wherein a combination of an NK1 antagonist of this invention (compound of formula I) is administered with an SSRI described above, the compound of formula I and SSRI can be administered simultaneously, consecutively (one after the other within a relatively short period of time), or sequentially (first one and then the other over a period of time). In general, when the antagonists are administered consecutively or sequentially, the NK1 antagonist of this invention (compound of formula I) is administered first.

Preferred are compounds of formula Ia and Ib

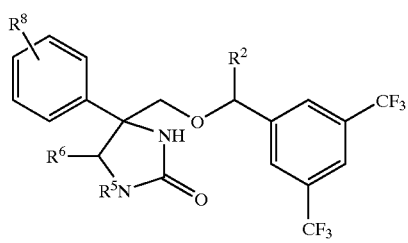

Ia

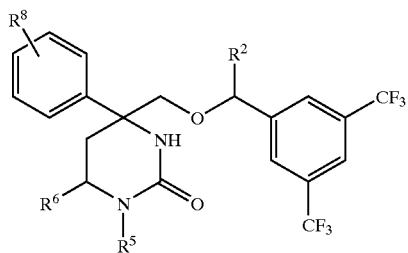

Ib wherein $R^8$ is H or halogen; $R^2$ is H, —$CH_3$ or —$CH_2OH$; $R^6$ is H or —OH; and $R^5$ is selected from the group consisting of hydrogen and groups of the formula —$(CH_2)_{n1}$—G as follows,

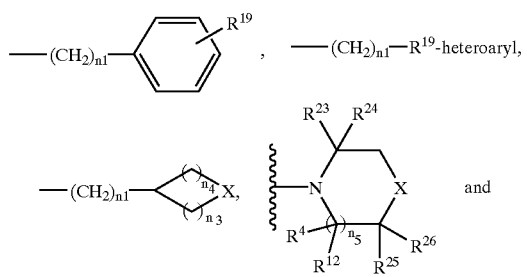

-continued

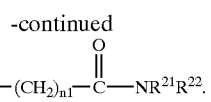

or —$(CH_2)_{n1}$—G', wherein $n_1$ is 2–4 and G'is H, —OH, —$OCH_3$—, —OEt, —O(i-Pr), —O-cyclopropyl, or —$CONR^{13}R^{14}$, wherein $R^{13}$ and $R^{14}$ are independently selected from the group consisting of H, —$CH_3$, Et, i-Pr, or cyclopropyl (Et is ethyl and i-Pr is isopropyl).

Also preferred are compounds of the formula Ic and Id

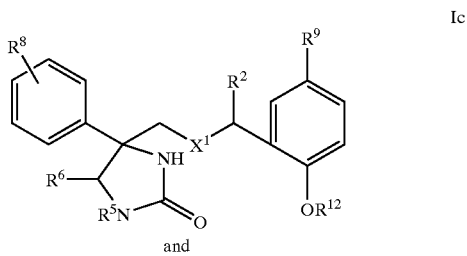

Ic and

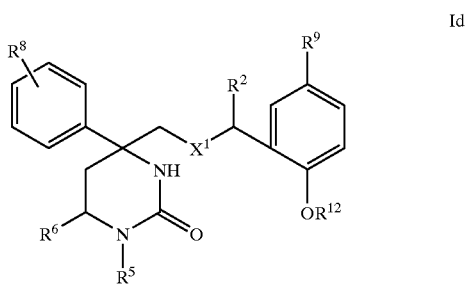

Id wherein $X^1$ is —O—, —NH—, —N($CH_3$)— or —(COCH_3)—; $R^8$ is H or halogen; $R^2$ is H, —$CH_3$ or —$CH_2OH$; $R^9$ is —$OCF_3$ or 5-(trifluoromethyl)-1H-tetrazol-1-yl; $R^6$ is H or —OH; $R^{12}$ is —$CH_3$ or cyclopropyl; and $R^5$ is selected from the group consisting of hydrogen and groups of the formula —$(CH_2)_{n1}$—G as shown above for structures Ia and Ib.

Preferred compounds of the invention are the compounds of examples 2, 61, 79a, 79b, 92, 93, 126, 127, 128, 129, 165a, 165b, 166a and 166b.

DETAILED DESCRIPTION

As used herein, the term "alkyl" means straight or branched alkyl chains. "Lower alkyl" refers to alkyl chains of 1–6 carbon atoms and, similarly, lower alkoxy refers to alkoxy chains of 1–6 carbon atoms.

"Cycloalkyl" means cyclic alkyl groups having 3 to 8 carbon atoms.

"Aryl" means phenyl, naphthyl, indenyl, tetrahydronaphthyl, indanyl, anthracenyl or fluorenyl. $R^{16}$-aryl and $R^{19}$-aryl refer to such groups wherein substitutable ring carbon atoms have an $R^{16}$ or an $R^{19}$ substituent.

"Halogen" refers to fluoro, chloro, bromo or iodo atoms.

"Heteroaryl" refers to 5- to 10-membered single or benzofused aromatic rings comprising 1 to 4 heteroatoms independently selected from the group consisting of —O—, —S—, —N= and —NH—, provided that the rings do not include adjacent oxygen and/or sulfur atoms. Examples of single-ring heteroaryl groups are furanyl, imidazolyl, isoxazolyl, isothiazolyl, oxadiazolyl, oxazolyl, pyrazinyl, pyrazolyl, pyridyl, pyrimidyl, pyrrolyl, tetrazolyl, thiadiazolyl, thiazolyl, thienyl, triazolyl and triazinyl.

Examples of benzofused heteroaryl groups are benzimidazolyl, benzofuranyl, benzo-thiophenyl, benzoxazolyl, indolyl and quinolyl. N-oxides of nitrogen-containing heteroaryl groups are also included. All positional isomers are contemplated, e.g., 2-pyridyl, 3-pyridyl and 4-pyridyl, and when $R^4$ or $R^5$ is heteroaryl, it can be joined to the nitrogen atom of the "—Q—" group either by a ring carbon or a ring nitrogen. $R^{19}$-heteroaryl refer to such groups wherein substitutable ring carbon atoms have an $R^{19}$ substituent. When $R^8$, $R^9$ or $R^{10}$ is heteroaryl, it is preferably tetrazolyl substituted by H, $C_1$–$C_4$ alkyl, $C_3$–$C_8$ cycloalkyl, —$CF_3$, —$SO_2$-($C_1$–$C_6$ alkyl) or —$OCF_3$.

"Heterocycloalkyl" refers to a 4- to 7-membered saturated ring comprising 1 to 3 heteroatoms independently selected from the group consisting of —O—, —S— and $NR^{21}$—, wherein $R^{21}$ is H or $C_1$–$C_6$ alkyl, and wherein the remaining ring members are carbon. Where a heterocyclic ring comprises more than one heteroatom, no rings are formed where there are adjacent oxygen atoms, adjacent sulfur atoms, or three consecutive heteroatoms. Examples of heterocyclic rings are tetrahydrofuranyl, pyrrolidinyl, tetrahydropyranyl, piperidinyl, morpholinyl, thiomorpholinyl and piperazinyl.

In the above definitions, wherein variables $R^1$ to $R^{26}$ are said to be independently selected from a group of substituents, we mean that $R^1$, $R^2$, $R^3$, etc., are independently selected, but also that where an $R^8$, for example, occurs more than once in a molecule, those occurrences are independently selected (e.g., if $X^1$ is —$NR^{12}$— wherein $R^{12}$ is hydrogen, G can be —$COOR^{12}$ wherein $R^{12}$ is methyl). Similarly, $R^8$, $R^9$ and $R^{10}$ can be independently selected from a group of substituents, and where more than one $R^8$, $R^9$ or $R^{10}$ is other than hydrogen, the substituents are independently selected; those skilled in the art will recognize that the size and nature of the substituent(s) will affect the number of substituents which can be present.

The "Q" groups are always joined to the rest of the molecule as shown, i.e., they are attached left-to-right, where —$X^2$— or —$NR^5$— is attached to the carbon to which $R^6$ and $R^7$ are attached, and —$NR^4$— is always attached to the carbon to which $Ar^1$ is attached.

Compounds of formula I can have at least one asymmetrical carbon atom and all isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention which have an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, tartaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention which are acidic (e.g., those compounds which possess a carboxyl group) form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared using methods known to those skilled in the art. Typical procedures are described below, although the skilled artisan will recognize that other procedures may be applicable, and that the procedure may be suitably modified to prepare other compounds within the scope of formula I.

Method 1

Compounds of formula I wherein $X^1$ is —O— or —S— and n is 1 can be prepared by the following method.

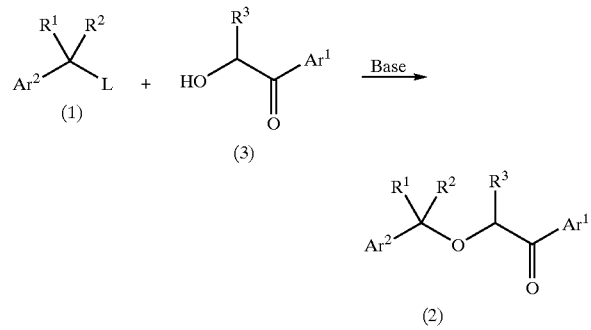

An alcohol (3), in which $Ar^1$ and $R^3$ are as defined above is converted to the ketone (2), by reaction with an activated derivative (1) of the alcohol (4), in which $Ar^2$, $R^1$ and $R^2$ are as defined above.

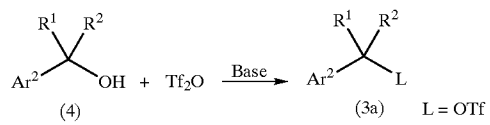

This reaction is most favorable when $R^1$, $R^2$ and $R^3$ are each H but, depending on the leaving group L, it may work effectively if either $R^1$, $R^2$ or $R^3$ is $C_1$–$C_6$ alkyl. A leaving group, L, of choice is $CF_3SO_2$— (triflate) but others also suffice, such as Br or I. The base used may vary but is preferably one of the hindered non-nucleophilic kind, of which an example is 2,6-di-tert-butyl-4-methyl pyridine.

The alkylating agent (3a) in which L is triflate may be prepared from the alcohol-type starting material (4) using triflic anhydride and the same hindered, non-nucleophilic base as is used for the alkylation.

The ketone (2) may be used to prepare compounds in which n is 1, $X^2$ is —$NR^5$— and Y is =O (5). Reaction of (2) with a metallic cyanide (e. g. KCN) and $(NH_4)_2CO_3$ results in the formation of the hydantoin, a process well known to those skilled in the art of organic synthesis:

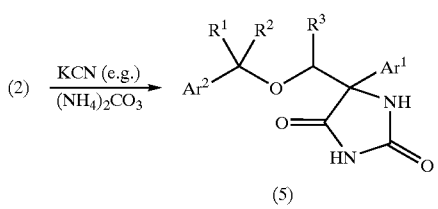

Selective reduction of the amide carbonyl and not the urea carbonyl may be accomplished by using a mixture of lithium aluminum hydride (LAH) and AlCl$_3$ as a preferred method although other methods are also available, such as the use of LAH in ether or THF at or above room temperature, up to the boiling point of the solution.

The reaction produces compounds of the invention in which R$^4$ and R$^5$ are both H. Introduction of a substituent, R$^5$, may be performed relatively selectively although in some cases a second substituent R$^4$ (where R$^4$=R$^5$ in this case) may be introduced at the same time. Such substitution reaction at the nitrogen atoms of (5) may be accomplished using one of many sets of conditions used for such transformations, for example, use of an organic base, such as triethylamine or Hunig's Base (di-isopropyl ethylamine) and the appropriate alkylating agent, L—R$^5$.

Reaction of the hydantoin (5) with p-methoxybenzyl chloride in acetone in the presence of K$_2$CO$_3$ and a catalytic quantity of tetra-n-butylammonium iodide produces the derivative (5A) which can be readily reduced to a mixture of alcohols (5B) by use of mild reducing conditions. Suitable reagents are LAH in THF at 0–30° C. for 1–6 hrs.

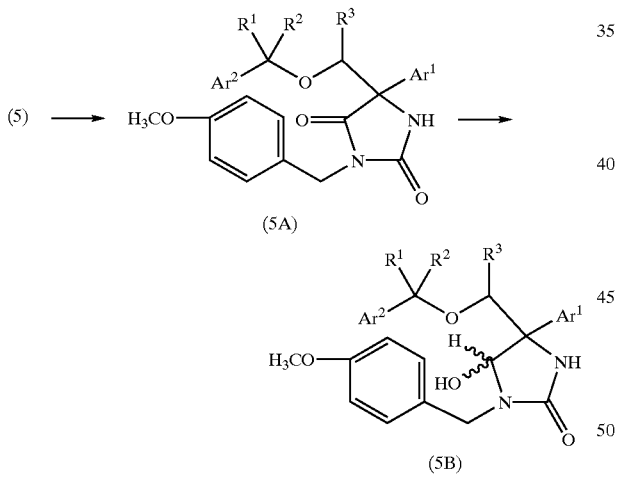

Subsequent removal of the PMB protecting group may be carried out using Ce(NH$_4$)$_2$(NO$_3$)$_6$ (CAN) in a neutral solvent, preferably a CH$_3$CN/water mixture. The mixture of chiral alcohols can frequently be separated and purified by chiral HPLC, preferably on one of the carbohydrate-based columns, such as one of the Daicel Chiralcel® or Chiralpak® series of columns.

Method 2

Compounds of formula I wherein X$^1$ is —O— or —S— and Y is =O or =S can be prepared by the following method.

The ketone (2) may also be made by the following sequence of reactions. The alcohol (1) may be converted to its alkoxide anion using a strong base, such as lithium bis(trimethyl silyl)amide or the like, followed by reaction, in an inert solvent, such as THF, with the N,O-dimethyl amide of the iodo-acid (7) to produce (8) which is known as a "Weinreb amide".

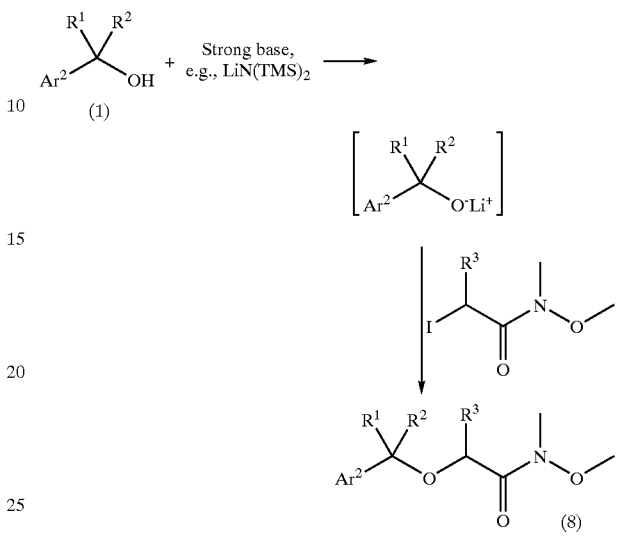

Addition of an organometallic derivative of Ar$^1$ (9) results in formation of the ketone (2). Suitable organometallic reagents include the Grignard (M is Mg) or lithium reagent. Suitable media for this reaction include neutral, non-reactive solvents such as ether or THF.

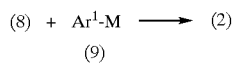

The ketone (2) may next be reacted with trimethylsilyl-cyanide in the presence of a Lewis acid catalyst, such as ZnI$_2$, and subsequently treated with saturated NH$_3$—CH$_3$OH at ambient temperature to yield an intermediate which may be reduced directly to diamine (10) using a powerful hydride reducing agent such as LAH in a neutral solvent such as THF.

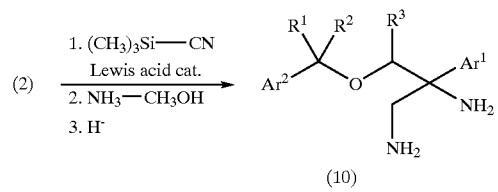

Reaction of the diamine (10) with a reagent known to introduce a carbonyl between two amines located in the correct position leads to the cyclic ureas (5) which are compounds of the invention. Examples of such reagents are COCl$_2$, carbonyl diimidazole and methyl or ethyl chloroformate. Subsequent modification by introduction of R$^4$ and R$^5$ groups may be performed as described in Method 1.

The reaction described above can also be used to prepare compounds of the invention in which X$^1$ is —S— by employing the thiol corresponding to the alcohol (4) shown above. In addition, reagents known to introduce the —C(=S)— function between two appropriately placed nitrogen atoms (such as thiocarbonyl diimidazole) may be used to prepare compounds in which Y is =S.

A further use of compounds such as 10A is to introduce the guanidine functions into compounds of the invention. Reacting (10A) with $CH_3$ I in a neutral solvent, such as $CH_3CN$, THF, or a mixture of the two, produces the S-methyl derivative (10B) which may then be reacted with an amine, $R^{11}$—$NH_2$, to produce guanidines (10C) or a tautomer.

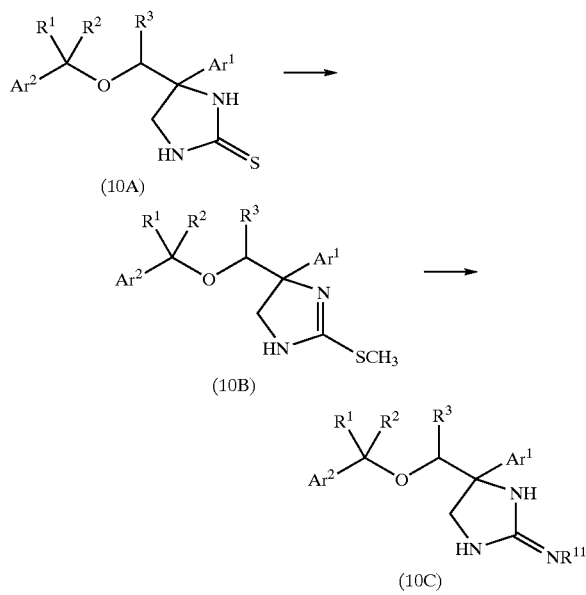

The diamine (10) is also a useful intermediate for preparation of products of the invention in which $X^2$ is —$NR^5$—. The group $R^5$ is introduced by use of an aldehyde or ketone precursor of $R^5$ by a process of reductive amination (otherwise known as reductive alkylation of the amine (10)). A proviso of this method is that the $R^5$ group may not contain a quaternary carbon atom next to the nitrogen atom. It also cannot be H, nor certain other of the definitions of $R^5$, for example, when G is —OH, —$SO_2R^{13}$ or —$NR^{13}R^{14}$ etc., then $n_1$ cannot be 0. To describe the process, the starting material (10D) will be used. By reacting (10) with (10D) in a neutral solvent, such as 1,2-dichloroethane, in the presence of a suitable reducing agent (sodium triacetoxyborohydride is particularly suitable for this reaction), and conventional work-up, a product (10E) is formed ($R^5$ is —$(CH_2)n_1$—G in which $n_1$ is 0 and G is

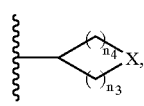

which $n_3=n_4=2$ and X=O:

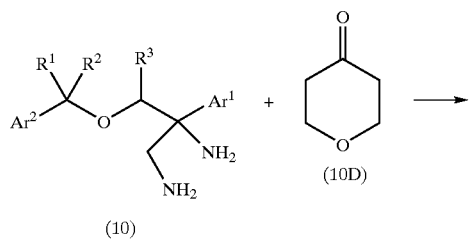

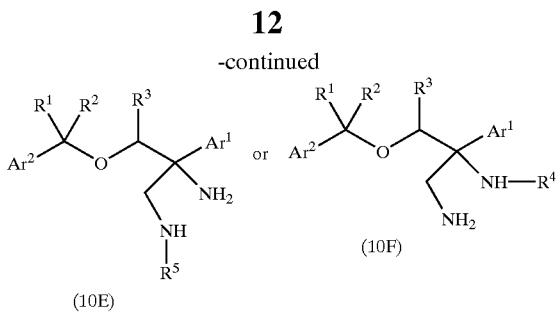

A variable amount of the isomeric structure (10F) (see above) may also form in this reaction, depending upon the reactants. It may be separated from (10E) by conventional chromatographic methods and reacted, as above, to yield compounds of the invention in which $R^4$ is the introduced substituent instead of $R^5$.

Reactions with other precursors of the $R^5$ group are also possible, as will be evident to one skilled in the arts of organic and medicinal chemistry. Ring closing of (10E) may be carried out by direct cyclization to make many of the Q groups of the invention in which an $R^5$ group is present and where Y is =O or =S, or compounds wherein Y is =N—$R^5$ can be made by the sequence of reactions described earlier for the synthesis of (10C).

A further use for the diamine (10) is in the preparation of compounds of the invention in which $Y^1$ is as defined above, except that it is not —$NH_2$, —$NHCH_3$ or —$SCH_3$. The diamine (10) may be heated with a carboxylic acid, $Y^1$—$CO_2H$, in a high boiling, neutral solvent, such as toluene to produce the amidines (10G) of the invention:

(10) + $Y^1$—$CO_2H$ ⟶

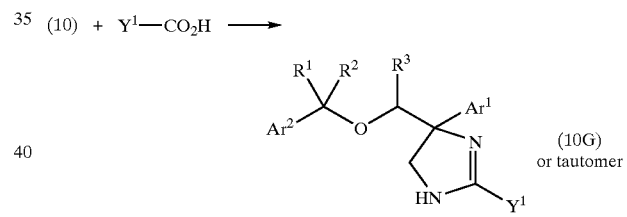

Method 3

An alcohol (3) may be reacted with an O-substituted hydroxylamine derivative, preferably methoxylamine to yield the oxime derivative (11). Conversion of the oxime to the alkoxide may be performed using a strong base, such as NaH, in a non-hydroxylic solvent, such as THF. Reaction of this anion with the substituted alkyl halide (12), in which Hal is preferably I or Br, produces the oxime-ether (13).

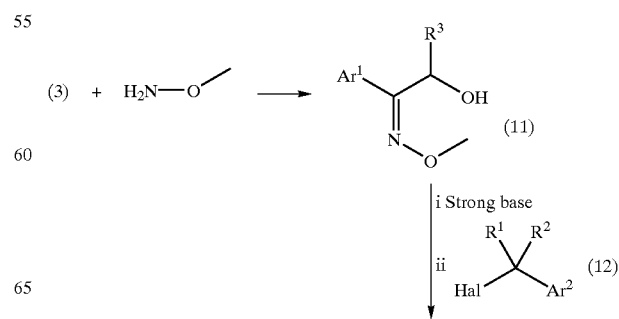

-continued

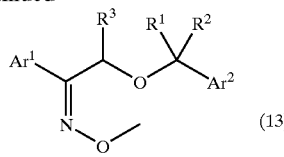
(13)

Cleavage of the oxime-ether (13) under acidic conditions, for instance, using 6N HCl at elevated temperature for 5 to 50 hours results in isolation of the ketone (2).

Further processing of (2) may be performed as described above in Method 1.

Method 4

Compounds of formula I wherein $X^1$ is —O— and n is 2–4 can be prepared by the following method (only $R^6$ is shown in the formulae, but both $R^6$ and $R^7$ can be present).

A diprotected aryl glycine ester, such as (14), in which "Prot" is a protecting group, preferably benzyl, and "E" is an ester group, preferably methyl or ethyl, may be converted to its anion using a strong base, such as lithium diisopropylamide, in an ether solvent, such as THF, at a temperature of about −78° C. Reaction of the anion with a halo-nitrile (15), in which "Hal" is preferably I, at temperatures between −78° C. and 0° C. results in the protected intermediate (16).

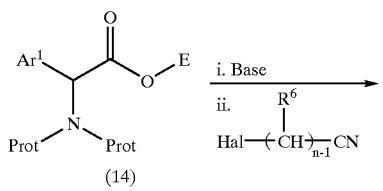
(14)

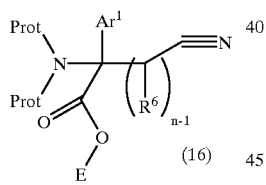
(16)

Reduction of the ester and nitrile simultaneously using a powerful hydride reducing agent, such as LAH, in an inert solvent, such as THF, at a temperature between about −78° C. and 0° C., produces aminoalcohol (17).

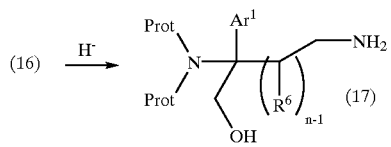
(17)

Removal of the protecting groups under standard conditions (e.g. 20% Pd(OH)$_2$ on active carbon in methanol if "Prot" is benzyl) yields the di-amine alcohol (18) which may be cyclized using one of the reagents known to introduce a C=O, C=S or —SO$_2$— group between two appropriately placed nitrogen atoms (e.g. COCl$_2$; carbonyl diimidazole; thiocarbonyl diimidazole, etc.) to yield (19).

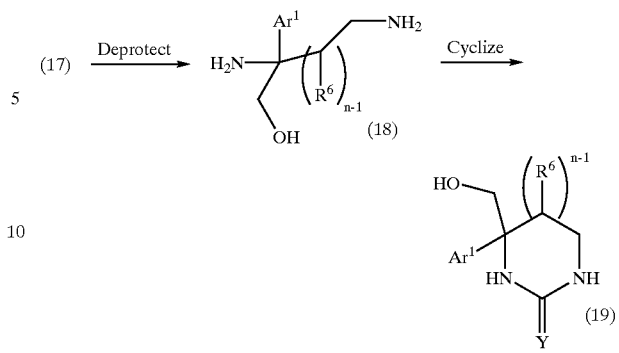
(19)

wherein =Y is =O or =S; the thio-urea can be prepared in a similar manner.

The alcohol (19) may be converted to a compound of the invention (20), by reaction of the mono-anion prepared by using a strong base, such as NaH, with a benzyl halide in the presence of Ag$_2$O. "Hal" is as defined above and the solvent is preferably a polar, non-hydroxylic solvent such as DMF.

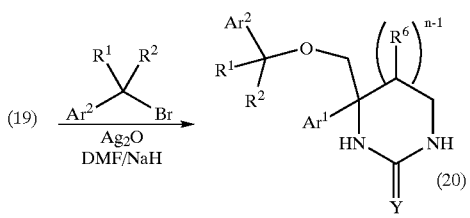
(20)

Subsequent modification by introduction of $R^4$ and $R^5$ groups may be performed as described in Method 1.

Method 4a

The intermediate (17), above, may also be converted to compounds of the invention via its di-BOC protected derivative (21).

Removal of the original protecting groups (if they are benzyl groups or similar) by hydrogenolysis in the presence of (BOC)$_2$O yields the di-BOC derivative (21).

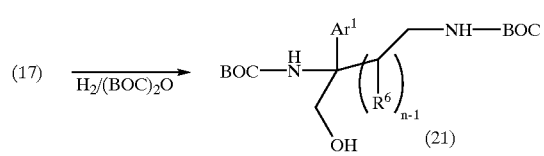
(21)

Such intermediates may be converted to the ethers (22) by reaction with an aryl halide (23), preferably a bromide or iodide. Use of silver oxide (Ag$_2$O) as a catalyst and base is desirable.

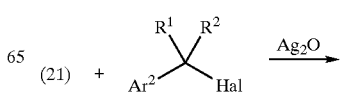

-continued

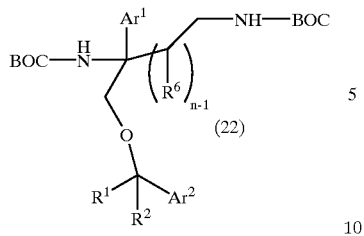

(22)

Removal of the BOC protecting groups under standard conditions (e.g. HCl/ether) produces the diamine which may be cyclized to compounds of the invention using the same reagents as described earlier in Method 2, e.g. $COCl_2$, carbonyl diimidazole, sulfonyl diimidazole, etc.

Method 5

Compounds of the invention in which $X^1$ is one of the nitrogen-containing groups may be synthesized from the amino ketone derivatives (10G), some of which may be commercially available while others can be synthesized by well-known literature techniques. Protection of the amino group in (10G), for instance as its BOC derivative, allows the hydantoin-forming reaction to occur to produce intermediates (10H) where "Prot" is the previously-introduced protecting group, e.g. BOC:

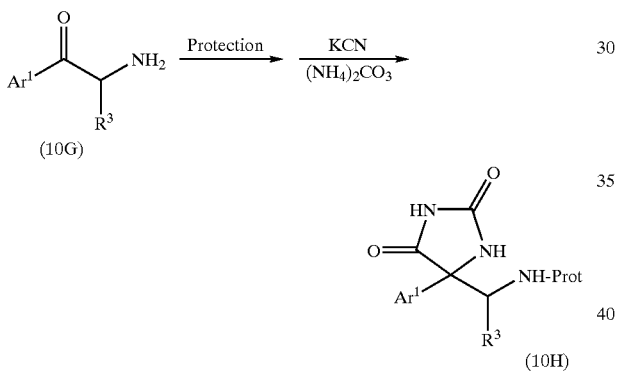

Reduction of one of the carbonyl groups preferentially, as described previously, using the $LiAlH_4/AlCl_3$ mixed reagents, followed by removal of the protecting group by an appropriate method (e.g., $CF_3CO_2H$ or HCl if it is BOC) produces the amine (10I)

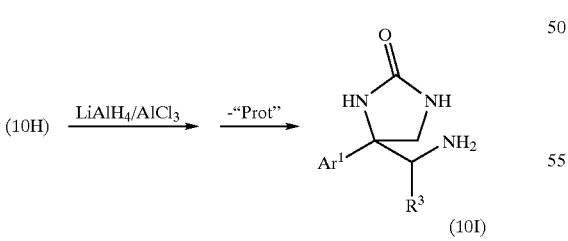

Reductive alkylation of the amine group with an aldehyde or ketone (10J) under conditions described for this transformation earlier (using sodium triacetoxyborohydride) or using one of the many published procedures known to carry out this reaction (e.g. sodium borohydride in an alcohol solvent) results in the amine (10K) which may be further modified by reactions well known in the art to produce other compounds of the invention, (10L) and (10M).

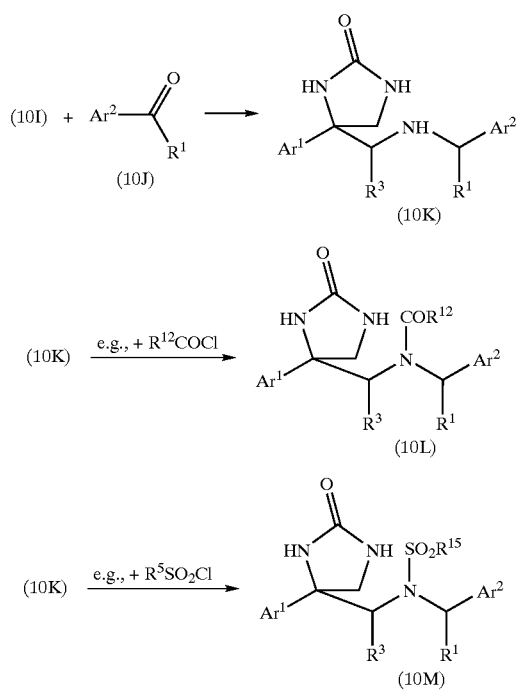

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
| --- | --- |
| —COOH | —COOalkyl, —COObenzyl, —COOphenyl |
| \NH/ | \NCOalkyl/, \NCObenzyl/, \NCOphenyl/, |
| | \NCH₂OCH₂CH₂Si(CH₃)₃/, \NC(O)OC(CH₃)₃/, |
| | \N-benzyl/, \NSi(CH₃)₃/, \NSi(CH₃)₂—C(CH₃)₃/ |
| —NH₂ | (succinimide) |

TABLE 1-continued

| Group to be Protected | Group to be Protected and Protecting Group |
|---|---|
| —OH | —OCH₃, —OCH₂OCH₃, —OSi(CH₃)₃,  or —OCH₂phenyl |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation for treatment of respiratory diseases; inflammatory diseases; skin disorders; ophthalmological disorders; addictions; stress related disorders; obsessive/compulsive disorders; eating disorders; mania; premenstrual syndrome; central nervous system conditions; gastrointestinal disorders; bladder disorders; atherosclerosis; fibrosing disorders; obesity; Type II diabetes; pain related disorders; and genitourinary disorders; may be varied or adjusted from about 1 mg to about 1500 mg, preferably from about 50 mg to about 500 mg, more preferably from about 20 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 1500 mg/day, in two to four divided doses.

Following are examples of preparing compounds of formula I. As used herein, RT is room temperature, Me is methyl, Bu is butyl, Br is bromo, Ac is acetyl, Et is ethyl, Ph is phenyl, THF is tetrahydrofuran, EtOAc is ethyl acetate, Et₂O is ether, LAH is lithium aluminum hydride, CDI is 1,1-carbonyl diimidazole; HOBT is hydroxybenzotriazole; DEC is 1,2-diethylaminoethyl chloride; TFA is trifluoroacetic acid; Et₃N is triethylamine, MTBE is t-butyl methyl ether; DAST is diethylaminosulfur trifluoride.

EXAMPLE 1

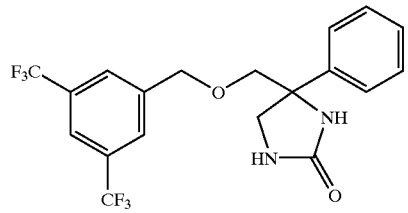

Method 1

Step 1:

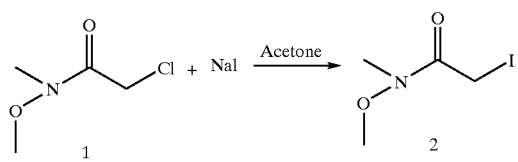

To a solution of 2-chloro-N-methylacetamide 98% (10.4 g, 74 mmol) in acetone (120 ml), NaI (12.2 g, 81.4 mmol) was added. The flask was filled with N₂ and covered with aluminum foil. After stirring at RT for 30 h, the reaction mixture was filtered. The filtrate was concentrated under vacuum to give a dark brown oil. The crude product was directly used without further purification in the next step.

Step 2:

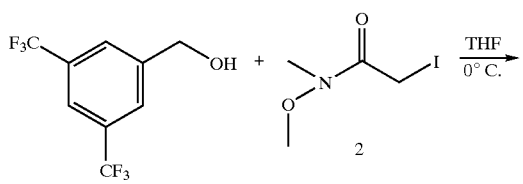

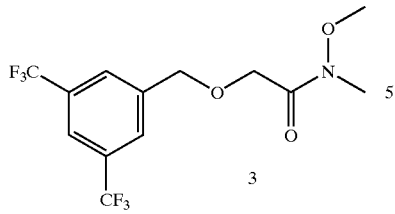

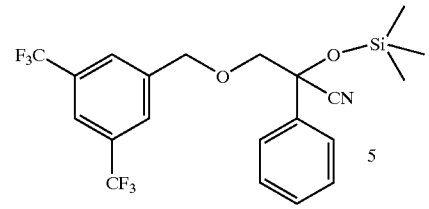

To a cooled solution of 3,5-bis(trifluoromethyl)benzyl alcohol (18.06 g, 74 mmol) in anhydrous THF (140 ml) at 0° C., solid KN(TMS)$_2$ (16.24 g, 81.4 mmol) was added slowly. The reaction was kept at 0° C. for 1 h. A solution of 2 in anhydrous THF (60 ml) was then added dropwise into the cooled solution. The reaction was allowed to gradually warm to RT over night under a N$_2$ atmosphere. After quenching with saturated NH$_4$Cl, the reaction was made slightly acidic with 1N HCl and extracted with EtOAc (200 ml×4). The combined organic layer was washed with brine (200 ml×2), dried over MgSO$_4$, filtered and concentrated. The crude material was purified by flash chromatography, eluting with 20% EtOAc in hexane to give 3 as an oil (12.3 g, 35.6 mmol, 48% yield).

Step 3:

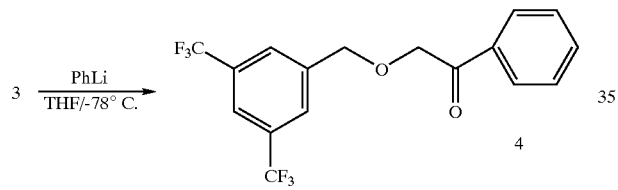

To a cooled solution of 3 (12.2 g, 35.34 mmol) in anhydrous THF (150 ml) at −75° C., phenyl lithium (22.58 ml, 40.64 mmol) was added dropwise. The reaction mixture was kept at low temperature for 1.5 h, then the cold bath was removed and the reaction was allowed to warm up to RT under N$_2$ protection. The reaction was cooled in an ice-water bath and quenched with saturated NH$_4$Cl solution (200 ml) using a dropping funnel followed by neutralizing the aqueous solution to pH ~7 with 1N HCl. After stirring for 15 min. the mixture was extracted with EtOAc (200 ml×4). The EtOAc extracts were combined, washed with brine (200 ml×2), dried over MgSO$_4$, filtered and concentrated to give a brown oil. The crude material was purified by flash grade silica gel chromatography, eluting with 15% EtOAc in hexane to give compound 4 (10.7 g, 28.44 mmol) with ~80% yield. FAB MS [M+1]$^+$ 263.1.

Step 4:

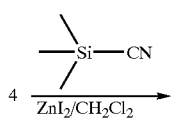

Trimethyl silyl cyanide (0.92 ml, 6.9 mmol) was added to a flask containing a solution of 4 (2.0 g, 5.52 mmol) in CH$_2$Cl$_2$ (11 ml), cooled with a water bath, followed by addition of ZnI$_2$ (88 mg, 0.276 mmol). The reaction was finished in 1 h. The insoluble ZnI$_2$ was filtered off and rinsed with CH$_2$Cl$_2$. Evaporation of the solvent yielded a light yellow oil as crude product which was used in the next step.

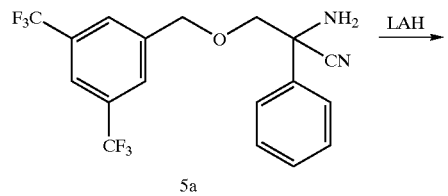

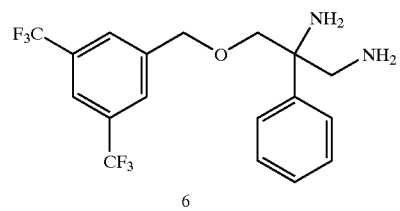

The crude material 5 was treated with saturated NH$_3$—CH$_3$OH (10 ml) and heated in an oil bath under N$_2$ at 45° C. After 2 h of heating, solid was filtered off and the filtrate was concentrated to give 5a.

To a suspension of LAH (0.84 g, 22 mmol) in anhydrous Et$_2$O (40 ml) at −78° C., a suspension of 5a in anhydrous Et$_2$O (40 ml) was added through an addition funnel under the protection of N$_2$. The reaction mixture was stirred at RT over night. After the reaction was complete, Et$_2$O (250 ml) was added. The reaction was quenched with saturated Na$_2$SO$_4$ solution and stirred for 2 h. The solid was filtered off and the filtrate was dried over MgSO$_4$, filtered again and treated with 4 M HCl in dioxane (3 ml). Evaporation of all the volatile solvents gave the crude product, which was further purified on Biotage cartiledge, eluting with 7.5% NH$_4$OH—CH$_3$OH (1:9) in 92.5% in CH$_2$Cl$_2$ to give 6 as an oil. FAB MS [M+1]$^+$ 393.1.

Step 5

To a solution of 6 (0.155 g, 0.395 mmol) in anhydrous THF (12 ml) was added 3 Å molecular sieves (200 mg) and 1,1'-carbonyl diimidazole (76.6 mg, 0.474 mmol). The mixture was stirred at RT overnight under N$_2$. Diluted with 200 ml EtOAc, the reaction mixture was washed with brine (100 ml×2), dried over MgSO$_4$, filtered and concentrated. The crude material was purified by flash chromatography, eluting with 5% NH$_4$OH—CH$_3$OH(1:9) in 95% CH$_2$Cl$_2$, to give the title compound as a solid with a 97% yield. FAB MS [M+1]$^+$419.1.

Method 2

Step 1:

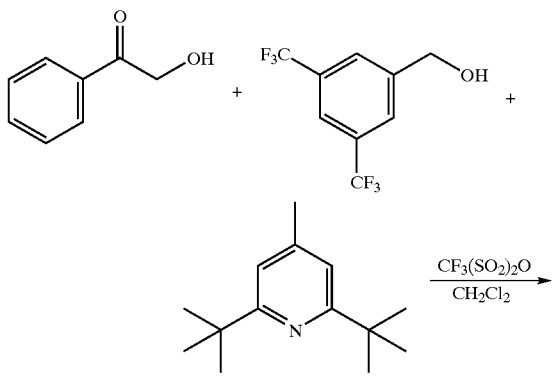

A mixture of 3,5-bis(trifluoromethyl)benzyl alcohol (39.9 g, 0.163 mol) and 2,6-di-t-butyl-4-methyl-pyridine (68.56 g, 0.33 mol) was placed in a 2 liter, 3-neck flask and vacuum dried overnight. To this green mixture was added dry $CH_2Cl_2$ (600 ml) (cooled with a water bath), followed by slow addition of trifluoromethylmethane sulfonic anhydride (50 g, 0.177 mol) through a dropping funnel under a $N_2$ atmosphere. After stirring at RT for 4 h, a solution of 2-hydroxy-acetophone (20.36 g, 0.149 mol) in dry $CH_2Cl_2$ (120 ml) was added slowing through a dropping funnel under $N_2$. The reaction mixture was stirred at RT for 5 days, then solid was filtered off. The filtrate was washed with brine (200 ml, 3×), dried ($MgSO_4$), filtered and concentrated to give a dark brown oil which was purified with flash grade silica gel (1 Kg), eluting with 10% EtOAc/hexane. Compound 4 was obtained as a solid (39.63 g, 0.11 mol, 74% yield).

Step 2:

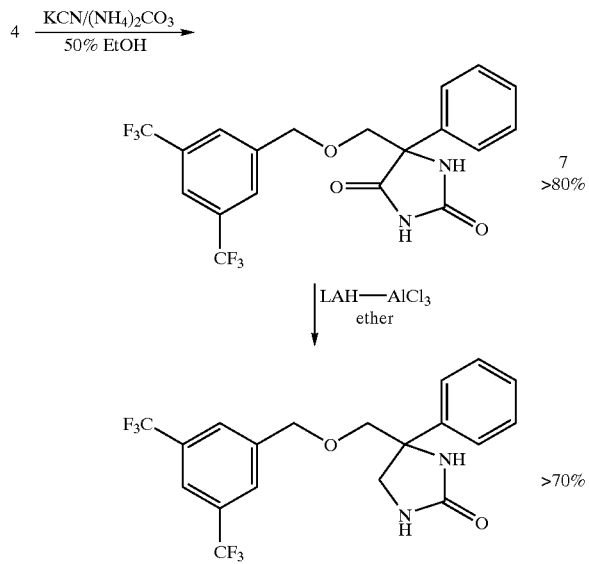

A mixture containing compound 4 (39.5 g, 109 mmol), KCN (10.64 g, 163 mmol) and $(NH_4)_2CO_3$ (37.47 g, 380 mmol) in 50% EtOH/$H_2O$ was heated in an oil bath at 60° C. under the $N_2$ atmosphere for 22 h. After cooling, ice-water (780 ml) was added and the mixture was stirred for 1 h. The white solid was filtered and rinsed with water. The solid was crystallized from hot dichloroethane. Pure compound 7 was obtained as a white solid (39 g, 90 mmol, 83%).

To a one-liter round bottom flask (cooled with an ice-water bath) containing $AlCl_3$ (24.6 g, 186 mmol) was slowly added 1 M LAH solution in $Et_2O$ (140 ml, 140 mmol) under an $N_2$ atmosphere. After stirring at 0° C. for 10 min. a solution of compound 7 (20 g, 46.2 mmol) in dry THF (170 ml) was added slowly to the LAH—$AlCl_3$ mixture. It was gradually warmed to RT and stirred at RT for 3 days. After completion, the reaction mixture was diluted with THF (200 ml) and excess LAH was decomposed with saturated $Na_2SO_4$ and 3 N NaOH. The mixture was stirred for 1 h at RT and solid was filtered off through a celite pad. The filtrate was dried over $MgSO_4$, filtered and concentrated to give the title compound as a foam which was purified on flash silica gel, eluting with 3.5% (1:9) $NH_4OH/CH_3OH$ in 96.5% $CH_2Cl_2$ to give pure title compound (16 g, 40 mmol, 87% yield) as a solid.

The racemic title compound was separated on a chiral column by using either a ChiralPak AS (Hexane/IPA (80:20)) or a Chiralcel OD ($CH_3CN$) column to give enantiomer A and enantiomer B (mp 138–140° C.). Enantiomer B: HRMS calculated for [M+1]: $C_{19}H_{17}F_6N_2O_2$ 419.1194, Found: 419.1190; C, H, N analysis: calculated C, 54.57; H, 3.71; N, 6.55; F 27.25 Found: C 54.55; H, 3.89; N, 6.59; F, 27.22; rotation in $CH_3OH$ $[\alpha]^{20}_D = -67.0°$.

EXAMPLE 2

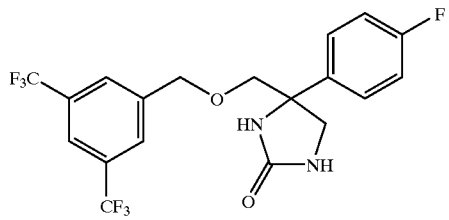

Part A:

Step 1:

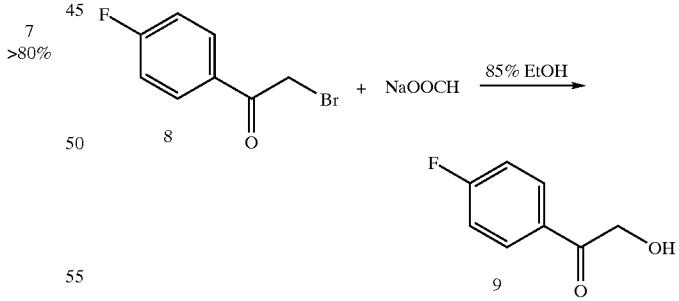

A suspension of 2-bromo-4'-fluoroacetophenone, 8, (30 g, 0.1368 mol) and HCOONa (59.2 g, 0.87 mol) in 85% EtOH (360 ml) was heated to 80° C. for 5 h. After cooling, it was stirred at RT over night under $N_2$. The reaction was stopped by evaporating off the EtOH, and the residue was redissolved in brine (500 ml) and extracted with EtOAc (200 ml×3). The combined organic layers were dried ($MgSO_4$), filtered and concentrated. The purified product was obtained by triturating the crude material with $CH_2Cl_2$, EtOAc and hexane to give 9 as a solid (18 g, 116 mmol, 85% yield).

Step 2:

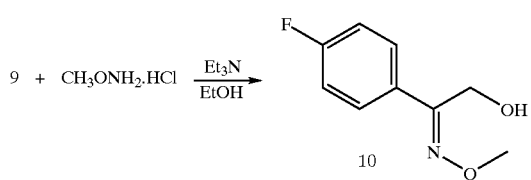

To a suspension of 9 (5.0 g, 32.44 mmol) in absolute EtOH (50 ml), 3Å molecular sieves (0.8 g), $CH_3NH_2 \cdot HCl$ (4.146 g, 48.67 mmol) and $Et_3N$ (6.77 ml, 48.67 mmol) were added. The mixture was heated to 85° C. under $N_2$ for 2.5 h. The mixture was cooled to RT, the solvent was evaporated under reduced pressure, and the crude product was redissolved in EtOAc (350 ml). This organic layer was washed with brine (150 ml×3), dried ($MgSO_4$), filtered and evaporated to dryness to give 10 as a solid (13.5 g, 7.36 mmol) in 97% yield.

Step 3:

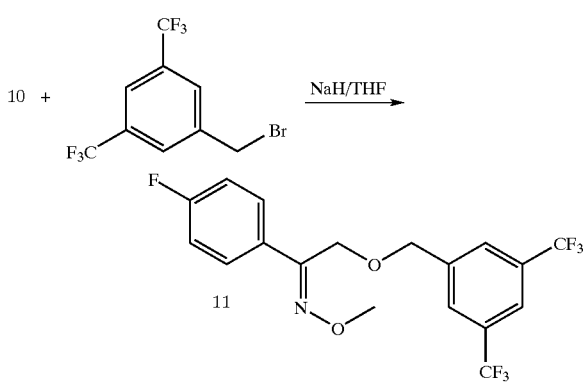

To a cooled solution of 10 (12.0 g, 65.5 mmol) in anhydrous THF (60 ml) (cooled in an ice-water bath) was added 60% NaH in mineral oil (3.14 g, 78.61 mmol). After stirring at RT for 15 min, the yellow suspension was treated with a solution of 3,5-bis(trifluoromethyl)benzyl bromide (13.62 ml, 72.05 mmol) in THF (13.62 ml). TLC indicated that the reaction was complete after 1.5 h at RT. Solvent was evaporated and the residue was redissolved in EtOAc (200 ml). This solution was washed with brine (50 ml×2), dried ($MgSO_4$), filtered and concentrated to give 11 as an oil (26.5 g, 64.77 mmol, 98% yield) FAB MS $[M+1]^+$ 410.1.

Step 4:

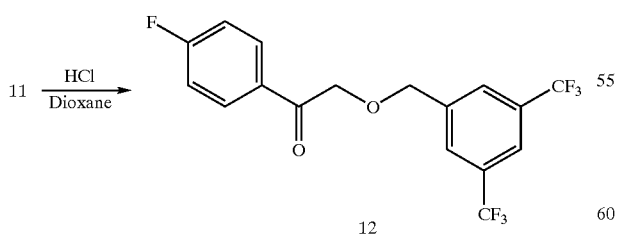

To a solution of 11 (26 g, 63.55 mmol) in dioxane (116 ml) was added 6 N HCl (378 ml, 2.268 mol). The mixture was heated at 100° C. for 2 days. After cooling to RT, the reaction mixture was poured into ice-cold KOH solution (120 g, ~2.142 mol in 240 ml $H_2O$). The products were extracted with $CH_2Cl_2$ (200 ml×3) from aqueous solution, dried ($MgSO_4$) and filtered. Solvents were evaporated to give a crude product as a brown oil. The final product was further purified by flash chromatography, eluting with 10% EtOAc in hexane to give 12 as a solid (13.41 g, 35.27 mmol, 55.5% yield).

Part B:

Step 1:

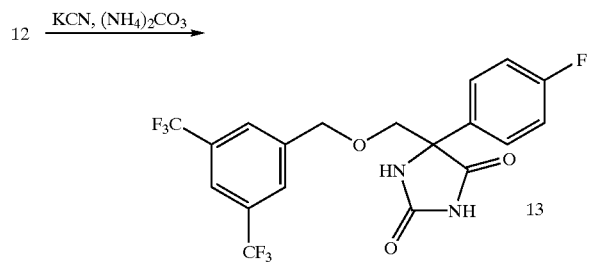

To the mixture of 12 (3.23 g, 8.5 mmol) in 1:1 $EtOH/H_2O$ (20 ml), KCN (0.83 g, 12.8 mmol) and $(NH_4)_2CO_3$ (2.86 g, 29.8 mmol) were added. The mixture was heated to 56° C. overnight, then cooled to RT. Iced water (60 ml) was added to the complete reaction. After 30 min, the solid was filtered off and rinsed with $CH_2Cl_2$ to give 13 as a white powdery product (3.12 g, 82%). FAB MS $[M+1]^+$ 451.1.

Step 2:

To a cooled 3-neck flask containing $AlCl_3$ (1.4 g, 10.7 mmol) at 0° C., 1M LAH in $Et_2O$ (8 ml, 8 mmol) was added dropwise via a syringe. A solution of 13 (1.2 g, 2.67 mmol) in anhydrous THF (10 ml) was added slowly and the reaction mixture was allowed to stir at RT overnight. After the reaction was complete, THF (100 ml) was added and excess LAH was decomposed with saturated $Na_2SO_4$ and 4N NaOH. After stirring for 1 h, the organic layer was separated, dried ($MgSO_4$), filtered and concentrated. The crude material was purified by flash silica gel eluting with 3.5% $NH_3$—$CH_3OH$ (1:9)/96.5% $CH_2Cl_2$ to give the title compound as a white foam (0.95 g, 0.22 mmol, 82% yield). FAB MS $[M+1]^+$ 437.1.

The racemic compound was separated with a Chiralcel OD column, eluting with $CH_3CN$ to give enantiomers A and B. The enantiomers A and B were reduced separately with LAH—$AlCl_3$ to give chiral compounds A and B. Pure chiral B was obtained by crystallization from hot $CH_3CN$ and hexane. Enantiomer B: HRMS calculated for [M+1]: $C_{19}H_{16}F_7N_2O_2$ 437.11 03, Found: 437.1100; C, H, N analysis: calculated C, 52.30; H, 3.46; N, 6.42; Found: C 52.38; H, 3.42; N, 6.31; rotation in $CH_3OH$ $[\alpha^{20}_D=-55.7$, mp: 130—132° C.

EXAMPLE 3

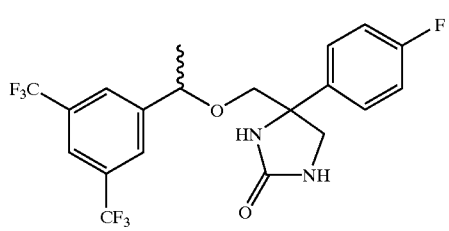

-continued

Step 1:

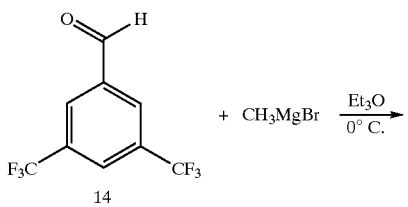

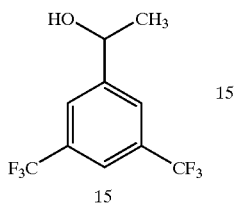

Step 3:

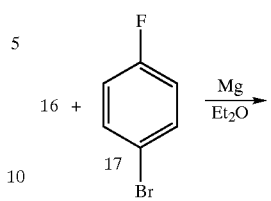

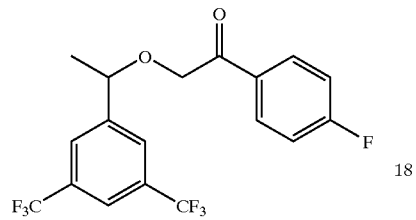

To the cooled solution of 3,5-bis(trifluoromethyl) benzaldehyde 14 (15 g, 62 mmol) in anhydrous Et$_2$O (100 ml) at 0° C., 3 M CH$_3$MgBr (25 ml, 75 mmol) was added dropwise. The reaction was kept at 0° C. for another 2 h, then stirred at RT for 2 h. The reaction was quenched by pouring into ice cold saturated NH$_4$Cl. Routine work-up gave 15 as an off-white solid product (15.4 g).

Step 2:

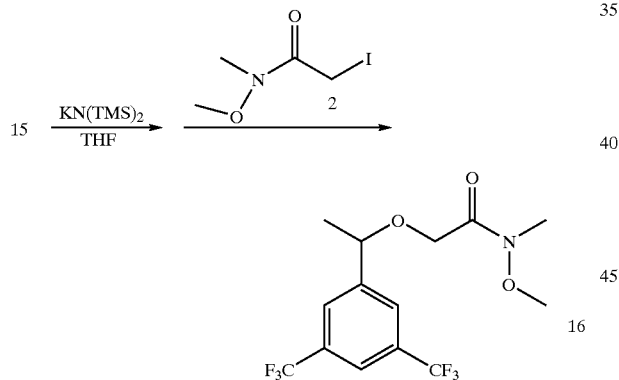

To the cooled solution of 15 (18.8 g, 72.9 mmol) in anhydrous THF (100 ml) at 0° C. was added solid KN(TMS)$_2$ (17.4 g, 87 mmol) portionwise. After stirring at 0° C. for 1 h, the potassium salt solution of 15 was added dropwise to a solution of 2 (17.5 g, 76.4 mmol) in anhydrous THF (20 ml). The reaction was kept at 0° C. overnight and quenched with saturated NH$_4$Cl (300 ml). The aqueous layer was extracted with CH$_2$Cl$_2$ (300 ml×3). The combined organic layer was washed with brine (300 ml), dried (MgSO$_4$), filtered and concentrated to a yellow oil (22 g). The crude product was further purified on silica gel (1:4 EtOAc/hexane) to give 16 as a pale yellow material (11 g, 31 mmol, 43% yield).

In a cooled flask (ice water bath) containing Mg turnings (1.12 g, 46.2 mmol) in anhydrous Et$_2$O (100 ml) was slowly added 4-bromofluoro-benzene 17 (7.7 g, 44 mmol), followed by a catalytic amount of 1,2-dibromoethane. After completion of the addition, the reaction was heated at 80° C. overnight under a N$_2$ atmosphere. After cooling, a solution of 16 (7.9 g, 22 mmol) in anhydrous Et$_2$O (40 ml) was added slowly to the Grignard solution at RT. After reaction was complete, a saturated NH$_4$Cl solution was slowly added under a N$_2$ atmosphere. The product was extracted from aqueous solution with CH$_2$Cl$_2$, combined, dried (Na$_2$SO$_4$), filtered and evaporated to give 18 as an oil. The crude material was purified on flash grade silica gel (400 g) eluting with 15% EtOAc/85% hexane to give 18 (7 g, 1.78 mmol, 87% yield). FAB MS (M+1)$^+$ 395.0.

Step 4:

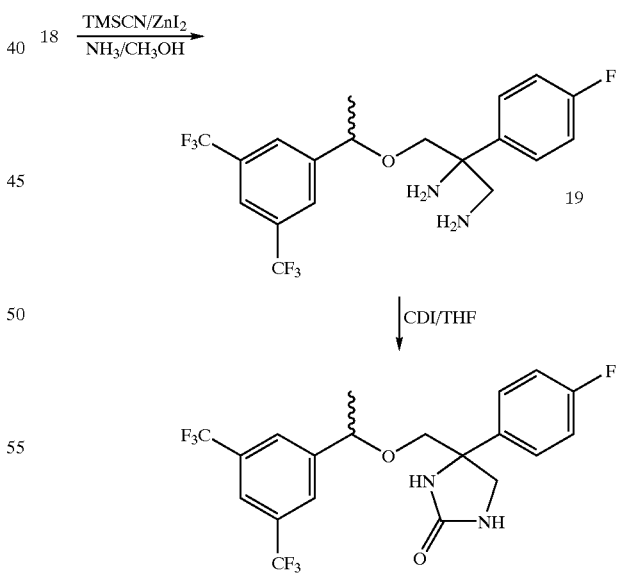

Compound 19 was prepared by an analogous method to that of Example 1 (step 4) using compound 18 in place of compound 4.

The title compound was prepared by a method analogous to that described for Example 1 (step 5) using compound 19 in place of compound 6. Two sets of diastereomers A and B were isolated by flash silica chromatography at compound 19 stage and these were cyclized separately to the title compounds with CDI reagent. Diastereomer A of the title compound, FAB MS [M+1]+ 451.1265, calculated [M+1]+ 451.1257; Diastereomer B of the title compound, FAB MS [M+1]+ 451.1261, calculated [M+1]+ 451.1257.

EXAMPLE 4

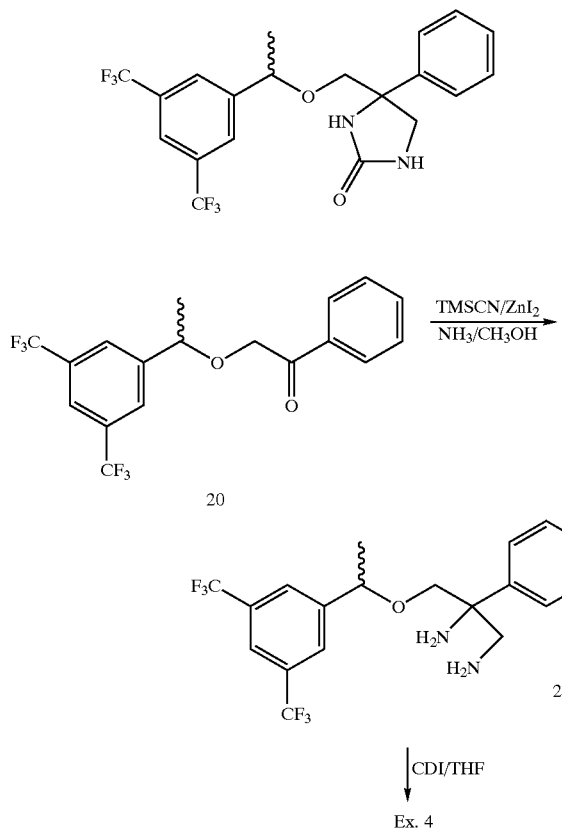

The title compound was prepared by an analogous method to that described for Examples 1 and 3 using α-methyl-3,5-bis(trifluoromethyl)-benzyl alcohol in place of 3,5-bis(trifluoromethyl)benzyl alcohol. Two sets of diastereomers were isolated by flash silica chromatography at compound 21 stage and cyclized separately to the title compound with CDI reagent. Diastereomer A of the title compound, FAB MS [M+1]+ 433.1358, calculated [M+1]+ 433.1351; diastereomer B of the title compound, FAB MS [M+1]+ 433.1358, calculated [M+1]+ 433.1351.

EXAMPLE 5

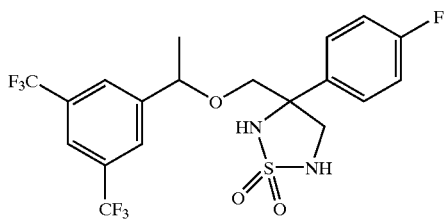

To a solution of compound 19 (0.22 g, 0.52 mmol) (prepared from compound 18 in Example 3) in pyridine (2 ml), sulfamide (50 mg, 0.52 mmol) was added. The mixture was refluxed for 24 h. After cooling, the reaction was diluted with EtOAc (200 ml), washed with 0.5 N HCl, brine, dried (MgSO4), filtered and concentrated to give a gum which was further purified on silica gel (1:4 EtOAc/hexane) to give the title compound as an off-white solid (40 mg, 16% yield). FAB MS [M+1]+ 487.3.

EXAMPLE 6

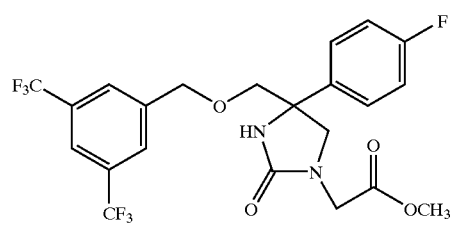

A mixture of the product of Example 2 (0.42 g, 0.96 mmol), toluene (5 ml), CH3ONa (0.13 g, 2.3 mmol) and Bu4NHSO4 (3.3 mg, 0.01 mmol) was heated to 90° C. for 1 h. Methyl bromoacetate (0.35 g, 2.3 mmol) was added later. After stirring at 80° C. for 48 h, the reaction was cooled to RT and product was extracted from the aqueous layer with CH2Cl2 (50 ml, 3×), washed with brine, and the organic layer was dried (MgSO4), filtered and concentrated to give a cloudy gum (0.4 g) which was further chromatographed with 3% NH3—CH3OH (1:9)/97% CH2Cl2 to give pure title compound as a solid (35 mg, 0.07 mmol, 8% yield). Electrospray MS [M+1]+ 509.1.

EXAMPLE 7

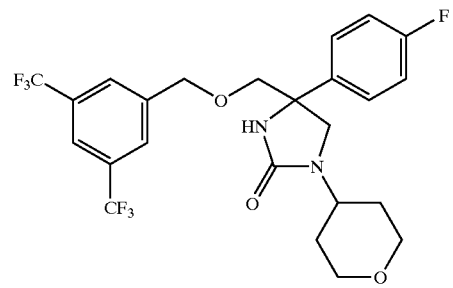

Step 1:

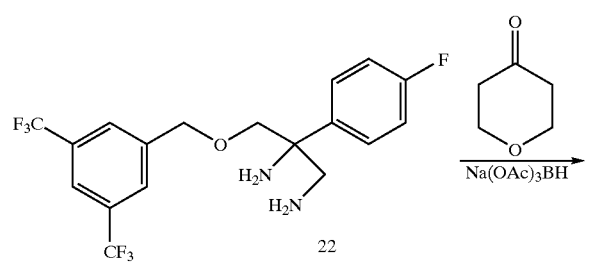

-continued

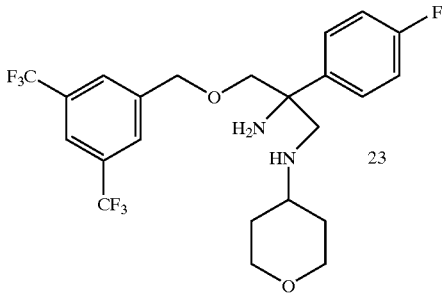

23

To the mixture of 22 (0.205 g, 0.5 mmol) (prepared analogously to the procedures described for 6 in Example 1) in dichloroethane (4 ml) were added tetrahydro-4H-pyranone (50 mg, 0.5 mmol) and sodium triacetoxyborohydride (0.21 mg, 1 mmol). After stirring overnight at RT, the reaction mixture was worked-up. The crude product was further purified on silica gel, eluting with 3.5% [1:9] $NH_3$—$CH_3OH$ in 96.5% $CH_2Cl_2$. Compound 23 was obtained as an oil (0.21 g, 0.43 mmol, 84% yield). FAB MS $[M+1]^+$ 495.45.

Step 2:

A mixture of 23 (0.15 g, 0.303 mmol) and CDI (120 mg, 0.74 mmol) in THF (5 ml) was stirred under a $N_2$ atmosphere at RT overnight. After work-up, a gummy material was obtained as a crude product which was then purified by chromatography, eluting with 2% $NH_3$—$CH_3OH$ (1:9)/98% $CH_2Cl_2$ to give the title compound as a white foam (0.11 g, 0.22 mmol, 73%). FAB MS $[M+1]^+$ 521.2.

EXAMPLE 8

24

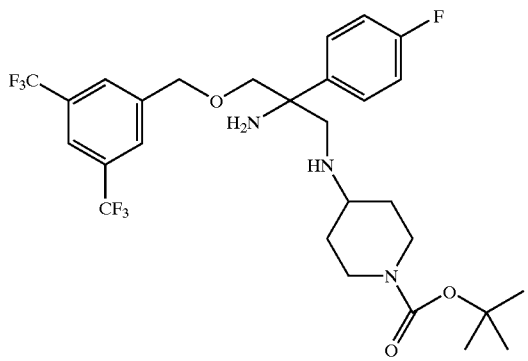

The title compound 24 was prepared by an analogous method to that described for compound 23 in Example 7 using 1-t-butoxylcarbonyl-4-piperidone in place of tetrahydro-4H-pyranone. FAB MS $[M+1]^+$ 594.1.

EXAMPLE 9

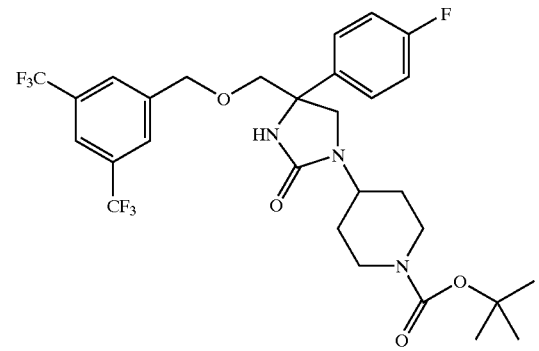

The title compound was prepared from compound 24 by an analogous method to that described for the title compound of Example 7. FAB MS $[M+1]^+$ 620.2.

EXAMPLE 10

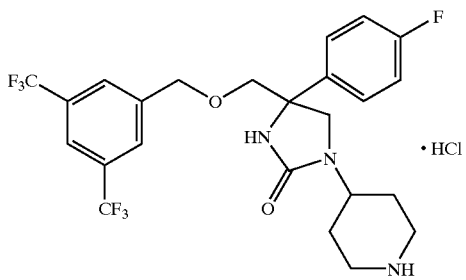

· HCl

A solution of the product of Example 9 (95 mg, 0.153 mmol) in $CH_2Cl_2$ (1 ml) was treated with 4M HCl in dioxane (2 ml) for 2 h. The reaction was worked-up by evaporating solvents and excess HCl. The title compound was obtained as an off-white salt. FAB MS $[M+1]^+$ 520.3.

EXAMPLE 11

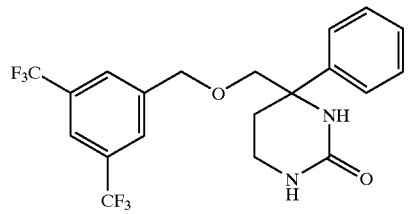

Step 1:

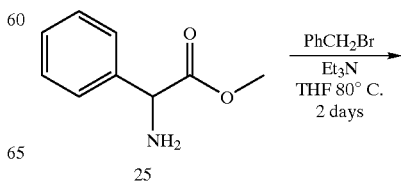

25

$\xrightarrow[\substack{Et_3N \\ THF\ 80°\ C. \\ 2\ days}]{PhCH_2Br}$

-continued

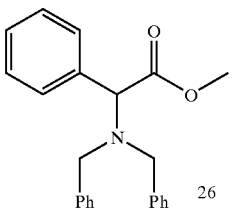

26

To a suspension of (R-(−)-2-phenylglycine methyl ester hydrochloride salt 25 (10 g, 49.6 mmol) in anhydrous THF (30 ml) and anhydrous DMF (10 ml) at RT were added Et$_3$N (22.13 ml, 158.9 mmol) and benzyl bromide (14.74 ml, 123.9 mmol). After 5 h of heating, the reaction mixture was treated with another equivalent of benzyl bromide (5.89 ml, 49.6 mmol) and Et$_3$N (6.9 ml, 49.6 mmol). The solution was heated at 80° C. under a N$_2$ atmosphere overnight. Additional benzyl bromide (6.9 ml, 49.6 mmol) was added next day and heating continued at 80° C. overnight to complete the reaction. After completion, the reaction mixture was cooled to RT, and poured into a separatory funnel containing NaHCO$_3$ solution and EtOAc. The aqueous layer was extracted with EtOAc (200 ml×3). The combined organic layer was washed with brine (300 ml), dried over MgSO$_4$, filtered and concentrated. Crude product was purified by chromatography (3% EtOAc in hexane) to give 26 as an oil (8.36 g, 22.62 mmol, 46% of yield). Electrospray MS [M+1]$^+$ 346.1.

Step 2:

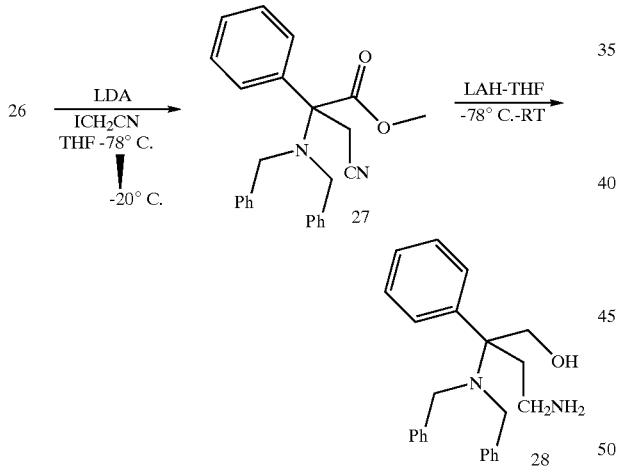

To a cooled solution of 26 (18 g, 52.11 mmol) in anhydrous THF (125 ml) at −78° C., a 2M LDA (32.6 ml, 65.2 mmol) solution in THF/n-heptane was added slowly. The reaction mixture was kept at this low temperature for another 2 h under a N$_2$ atmosphere, then treated with 95% ICH$_2$CN (4.97 ml, 65.2 mmol) dropwise through a syringe. The reaction was stirred at −78° C. for 4 h and −20° C. overnight. A mixture of chilled saturated aqueous NH$_4$Cl solution was added to quench the reaction. The separated aqueous layer was extracted with EtOAc (200 ml×3). The combined organic layers were washed with brine (300 ml), dried over MgSO$_4$, filtered and concentrated. The residue was purified by flash chromatography (15% EtOAc in hexane) to afford 27 as an oil (10.24 g, 51.2%). Electrospray MS [M+1]$^+$ 385.1.

To a solution of 27 (6.0 g, 15.6 mmol) in anhydrous THF (100 ml) was added 1 M LAH in THF (100 ml, 100 mmol) slowly at −78° C. under a N$_2$ atmosphere. The reaction mixture was let to stir from −78° C. to RT overnight. After completion, the reaction was diluted with THF (100 ml) and quenched (cooled in an ice-bath) with a Na$_2$SO$_4$ saturated aqueous solution slowly through a dropping funnel. The mixture was stirred at RT for 1 h, then filtered and concentrated. The crude product was triturated with CH$_3$OH and EtOAc and filtered. The solid (2.24 g) was the desired pure compound. The filtrate was further purified by flash grade silica gel, eluting with 6% NH$_4$OH—CH$_3$OH (1:9)/94% CH$_2$Cl$_2$ to give compound 28 (1.3 g) as a solid with a total yield of 64%.

Step 3:

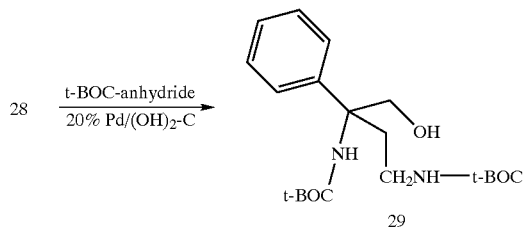

To a solution of 28 (1.27 g, 3.523 mmol) in CH$_3$OH (150 ml) was added t-BOC anhydride (1.8 g, 8.24 mmol) and 20% Pd(OH)$_2$ on carbon (0.254 g). The mixture was hydrogenolyzed at 50 psi in a Parr Shaker overnight. After completion, excess catalyst was filtered and rinsed with CH$_3$OH. Solvent was concentrated and gave the crude product 29, which was further purified on flash grade of silica gel, eluting with 5% NH$_3$—CH$_3$OH (1:9) in 95% CH$_2$Cl$_2$ to give 29 as a white solid (1.14 g, 2.99 mmol) with a 85% of yield. Electrospray MS [M+1]$^+$ 381.1.

Step 4:

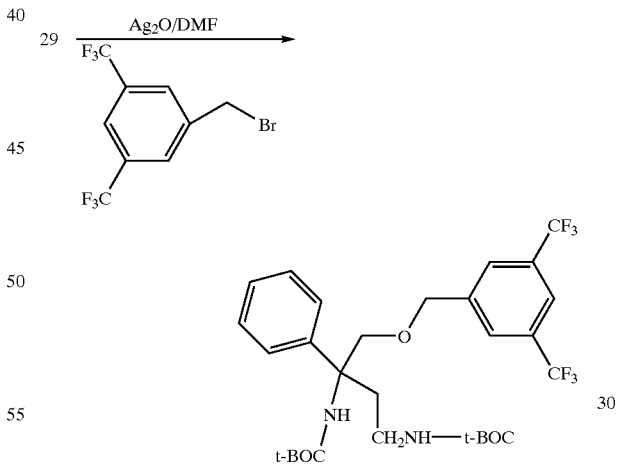

To a solution of 29 (2.4 g, 6.306 mmol) (from another batch) in anhydrous DMF (20 ml) was added 4 Å molecular sieves (1 g), 3,5-bis(trifluoromethyl)benzyl bromide (1.736 ml, 9.459 mmol) and Ag$_{2O}$ (2.998 g, 12.61 mmol) under a N$_2$ atmosphere. The reaction was stirred at RT in the dark overnight. EtOAc (300 ml) was added, and the mixture was washed with brine (100 ml×2), dried over MgSO$_4$, filtered and evaporated to give 30 as a yellow oil. It was purified by chromatography, eluting with 0.75% NH$_3$—CH$_3$OH (1:9)/

99.5% CH$_2$Cl$_2$ to give 30 as a solid (2.4 g, 3.9 mmol, 63% yield). Electrospray MS [M+1]$^+$ 607.1.

Step 5:

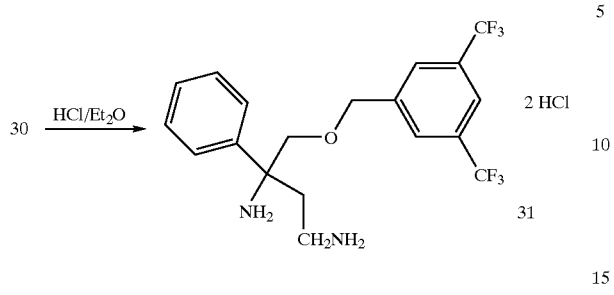

To a solution of 30 (1.38 g, 2.27 mmol) in CH$_2$Cl$_2$ (8.5 ml) was added 2N HCl/Et$_2$O (8.5 ml, 17 mmol). The solution was stirred at RT overnight under a N$_2$ atmosphere. After the reaction was complete, all solvents were evaporated to give compound 31 as a solid. Crude yield: 1.08 g, 99.6%.

Step 6:

To a suspension of 31 (1.07 g, 2.233 mmol) in anhydrous THF (30 ml) was added 4 Å molecular sieves (1.0 g), Et$_3$N (0.653 ml, 4.69 mmol) and CDI (0.434 g, 2.679 mmol) at 0° C. The reaction mixture was stirred at ambient temperature overnight under a N$_2$ atmosphere. After completion, the reaction mixture was evaporated and the residue was partitioned between EtOAc and water (300 ml). The organic layer was combined and washed with brine (50 ml×3), dried over MgSO$_4$, filtered and concentrated to give a clear oil of the title compound. The crude product was further purified on flash grade silica gel, eluting with 5% NH$_4$OH—MeOH (1:9)/95% CH$_2$Cl$_2$ to give the title compound as a solid (0.46 g, 1.06 mmol) in a 48% of yield. Electrospray MS [M+1]$^+$ 433.1.

EXAMPLE 12

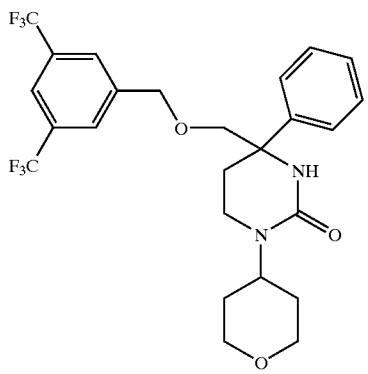

Step 1:

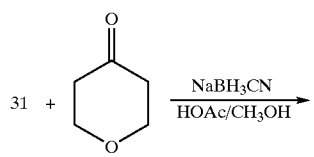

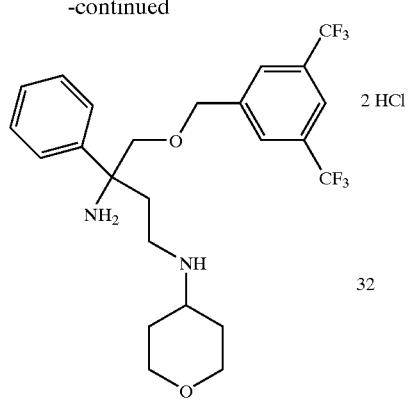

To a cooled solution of 31 (0.5 g, 1.044 mmol) in CH$_3$OH (14.65 ml) was added Et$_3$N (0.29 ml, 2.088 mmol), Na$_2$SO$_4$ (200 mg) and tetrahydro-4H-pyran-4-one (98 μl, 1.044 mmol) at 0° C. under N$_2$ atmosphere. After 1 h, NaBH$_3$CN (103.5 mg, 1.566 mmol) and HOAc (125.6 μl, 2.088 mmol) were added. The reaction was stirred at 0° C. for 3 h and 1 N NaOH was added until solution reached pH=10. The volatile solvent was evaporated in vacuo. The residue was redissolved in CH$_2$Cl$_2$ (300 ml) and washed with aqueous mixture of saturated NaHCO$_3$—NaCl—H$_2$O. The combined organic layer was dried over MgSO$_4$, filtered and evaporated to give 32 as an oil. The crude product was passed through 50 g of flash grade silica gel, eluting with 5% NH$_3$—CH$_3$OH (1:9)/95% CH$_2$Cl$_2$ to give 32 as an oil (0.28 g, 0.57 mmol, 55%). Part of this material (100 mg) was redisolved in CH$_2$Cl$_2$ and two equivalents of HCl-ether solution was added. After stirring for 10 min, solvents were evaporated to give HCl salt of compound 32 as a solid. Electrospray MS [M+1]$^+$ 491.1.

Step 2:

To a solution of 32 (180 mg, 0.367 mmol) in anhydrous THF (7.0 ml) was added 4 Å molecular sieves (300 mg) and CDI (71.4 mg, 0.44 mmol). The reaction mixture was stirred at RT for over 50 h. A small amount of NaHCO$_3$ solution was added to quench the reaction. The cloudy mixture was diluted with EtOAc (200 ml). The organic layer was washed with brine (50 ml×3), dried over MgSO$_4$, filtered and concentrated. The crude product was purified on 30 g of flash grade silica gel, eluting with 5% NH$_3$—CH$_3$OH (1:9)/95% CH$_2$Cl$_2$ to give the title compound as a solid (0.118 g, 0.23 mmol, 63%). FAB MS [M+1]$^+$ 517.1.

EXAMPLE 13

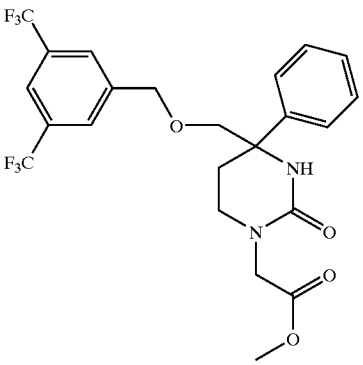

To a cooled solution of the product of Example 11 (0.36 g, 0.832 mmol) in anhydrous DMF (2 ml) at 0° C. was added 60% NaH (40 mg, 0.998 mmol) in mineral oil. After stirring 30 min, methylbromo acetate (88 µl, 0.915 mmol) was added. The reaction was stirred at 0° C. to RT overnight under a $N_2$ atmosphere. EtOAc (300 ml) was added and the mixture was washed with brine (100 ml×3), dried over $MgSO_4$, filtered and concentrated to give a crude material. It was separated on flash grade silica gel (50 g), eluting with 5% $NH_3$—$CH_3OH$ (1:9) in 95% $CH_2Cl_2$ to give the title compound as a gummy oil (15 mg, 0.029 mmol, 3.5%). Electrospray MS $[M+1]^+$ 505.1.

EXAMPLE 14

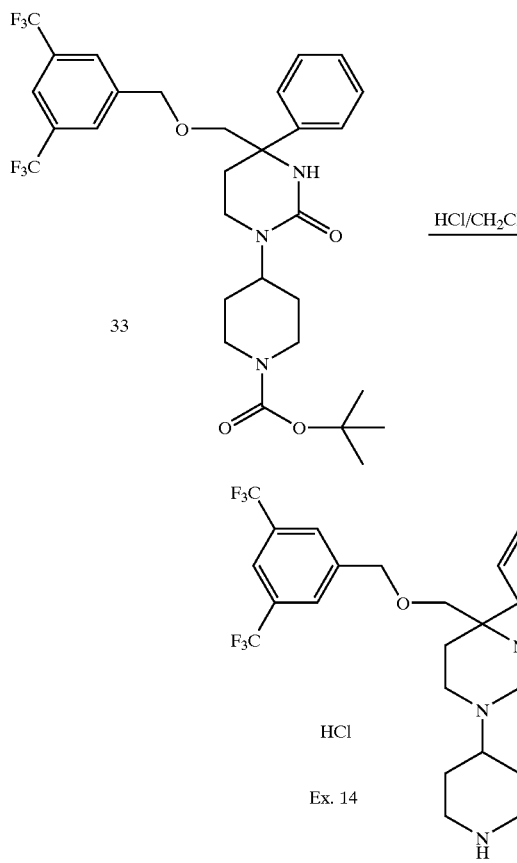

Compound 33 was prepared by an analogous method to that described in Examples 8 and 9 using compound 31 as starting material in place of compound 22. Electrospray MS $[M+1]^+$ 616.1.

To a solution of 33 (328 mg, 0.533 mmol) in $CH_2Cl_2$ (2.66 ml) was added 2N HCl—$Et_2O$ (2.66 ml, 5.33 mmol). The reaction mixture was stirred at RT for 18 h under a $N_2$ atmosphere. Crude title compound was obtained by evaporating off the solvents and used directly in the following step. FAB MS $[M+1]^+$ 516.1.

EXAMPLE 15

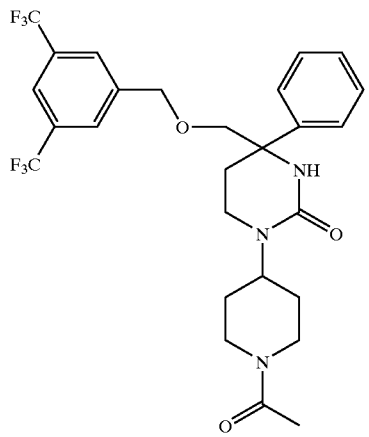

To a solution of the product of Example 14 (110 mg, 0.199 mmol) in anhydrous $CH_2Cl_2$ (2.2 ml) was added $Et_3N$ (61 µl, 0.438 mmol), followed by the addition of HOAc (12 µl, 0.2 mmol), HOBT (27 mg, 0.2 mmol) and DEC (46 mg, 0.24 mmol). The reaction mixture was stirred at RT for 3 h under a $N_2$ atmosphere. After completion, $CH_2Cl_2$ (200 ml) was added and the reaction mixture was washed with brine (50 ml×2), dried over $MgSO_4$, filtered and evaporated to give the title compound as a foam. The crude material was purified on flash grade silica gel, eluting with 5% $NH_4OH$/ $CH_3OH$ (1:9)/95% $CH_2Cl_2$ to afford the title compound as a white solid (90 mg, 0.16 mmol, 81%). Electrospray MS $[M+1]^+$ 558.1.

EXAMPLE 16

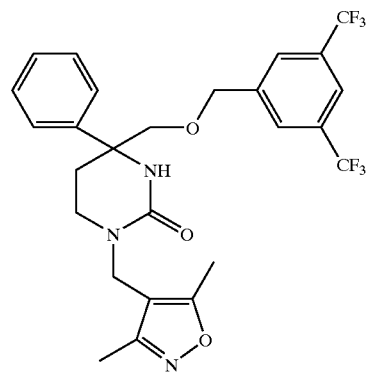

The title compound was prepared by an analogous method to that described in Example 13 using 4-chloromethyl-3,5-dimethyl-isoxazole in place of methylbromo acetate and 60% NaH in mineral oil (1.5 equivalent). Electrospray MS $[M+1]^+$ 542.1.

EXAMPLE 17

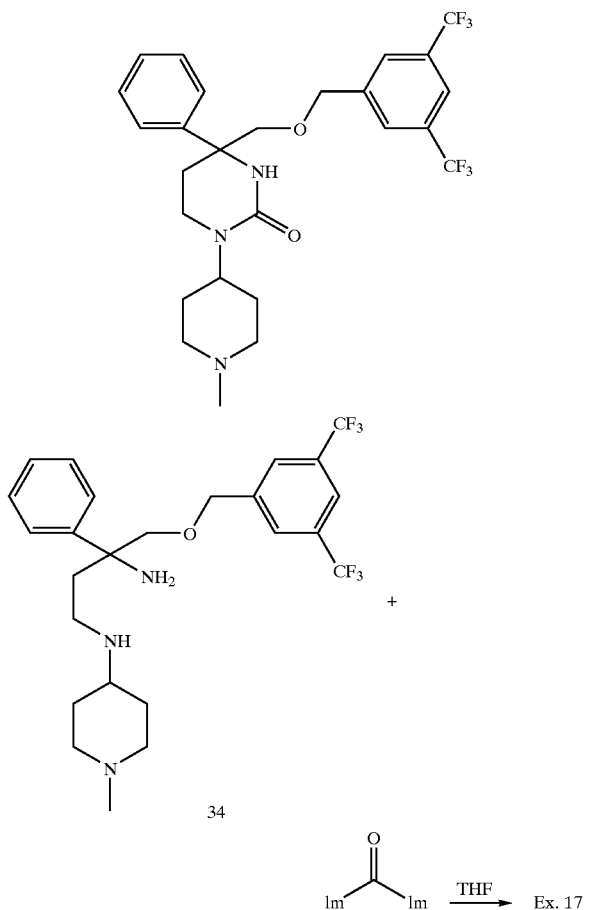

The title compound and compound 34 were prepared by a method analogous to that described in Examples 12 using 1-methyl-4-piperidone in place of tetrahydro-4H-pyran-4-one. Electrospray MS [M+1]$^+$ 530.1.

EXAMPLE 18

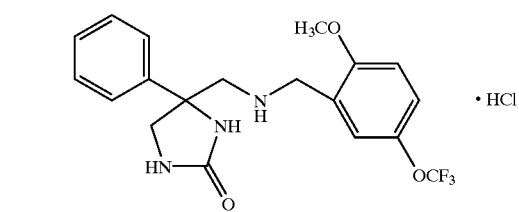

Step 1:

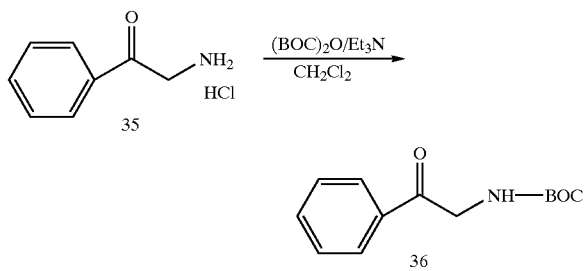

To a solution of 35 (14.8 g, 86.23 mmol) and Et$_3$N (36 ml, 258.69 mmol) in CH$_2$Cl$_2$ (200 ml), (BOC)$_{2O}$ (20.70 g, 94.85 mmol) was added at RT. Stirred for 18 h, the reaction was stopped by diluting with CH$_2$Cl$_2$ (100 ml) and transferred into a separatory funnel. The organic mixture was washed with water (100 ml×2), dried over Na$_2$SO$_4$, filtered, and concentrated to give a light yellow solid 36 (20 g, 85 mmol, 99%). This crude product was used without purification in the following step.

Step 2:

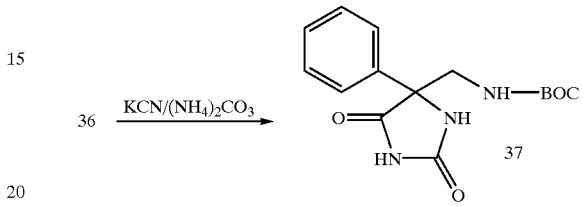

In a flask containing 36 (20.28 g, 86.195 mmol), (NH$_4$)$_2$CO$_3$ (28.99 g, 301.68 mmol) and KCN (8.42 g, 129.29 mmol) was added a (1:1) mixture of EtOH and water (180 ml). The mixture was heated to 56° C. under N$_2$ atmosphere for 48 h. The reaction was cooled with an ice bath and then the precipitate was filtered off. The residue was rinsed with water, then hexane, and air dried to give 37 as a white solid (20 g). The filtrate was diluted with EtOAc (500 ml) and the organic layer was separated, dried over Na$_2$SO$_4$, filtered and concentrated. The solid was triturated with Et$_2$O then CH$_2$Cl$_2$, and dried in air to give additional 37 (4.8 g) as a solid (total 24.8 g, 81.2 mmol, 94%).

Step 3:

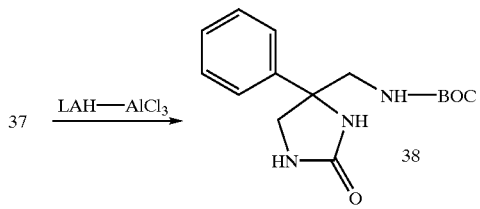

To a 3-neck flask equipped with a N$_2$ inlet was added AlCl$_3$ (10.48 g, 78.60 mmol). An ice-bath was placed under the flask. A solution of 1M LAH in Et$_2$O (59 ml, 59 mmol) was added dropwise to the cooled flask. After 10 min, a solution of hydantoin 37 (6 g, 19.65 mmol) in anhydrous THF (100 ml) was added to the reaction mixture slowly. The reaction was kept at 0° C. for additional 15 min then gradually warmed up to RT overnight. In a cooling bath, the reaction was carefully quenched with water (3 ml), followed by 15% NaOH (3 ml) and water (9 ml) under an atmosphere of N$_2$. Stirred for 15 min, the reaction mixture was filtered and rinsed with EtOAc, the THF. The filtrate was transferred to a separatory funnel containing water (50 ml). The organic layer was separated, dried over Na$_2$SO$_4$, filtered, and concentrated to give 38 as a white solid (4.5 g, 15.44 mmol, 79%). The crude product was used without further purification. FAB MS [M+1]$^+$ 292.1.

39

Step 4:

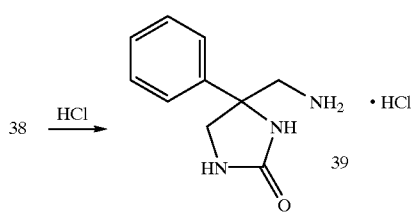

To a solution of 38 (0.9 g, 3.09 mmol) in CH$_3$OH (20 ml), a 4 N HCl (8 ml, 31 mmol) solution in dioxane was added. After stirring at RT for 2 h, the reaction was stopped by evaporating off the volatile solvents. CH$_3$OH was added twice with subsequent evaporation. A white foam (0.65 g, 2.85 mmol, 92% yield) was obtained as crude product, which was used directly in the following step.

Step 5:

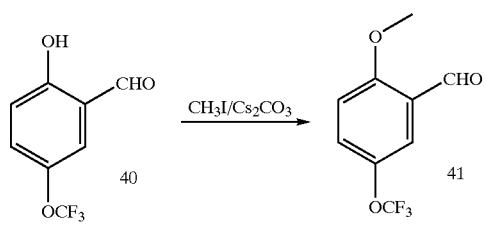

To a solution of alcohol 40 (0.5 g, 2.43 mmol) in dioxane (2.5 ml), water (0.15 ml) was added, followed by Cs$_2$CO$_3$ (3.96 g, 12.15 mmol) and CH$_3$I (0.45 ml, 7.29 mmol). The mixture was heated to 72° C. in a sealed tube for 3 h. The reaction mixture was then cooled to RT and concentrated. The residue was flashed through silica gel, eluting with 40% EtOAc/hexane. Compound 41 was obtained as an oil (0.52 g, 2.36 mmol, 97% yield).

Step 6:

To a solution of 39 (0.28 g, 1.23 mmol) in (9:1) of trifluoroethanol/Et$_3$N (10 ml), aldehyde 41 (0.27 g, 1.23 mmol) was added, followed by 3 Å molecular sieves (1.5 g) and sodium triacetoxyborohydride (0.91 g, 4.31 mmol). This turbid reaction was made clear by adding dichloroethane (15 ml). After 18 h, the reaction mixture was filtered and rinsed with EtOAc (200 ml) and CH$_3$OH (200 ml). The combined filtrate was concentrated. The residue was redissolved in EtOAc (250 ml) and washed with saturated NaHCO$_3$ (100 ml). The organic layer was dried over Na$_2$SO$_4$, filtered and concentrated. The crude material was purified on flash silica gel, eluting with EtOAc/Et$_3$N (9:1) to give the title compound as an oil (0.3 g, 0.76 mmol, 62% yield), FAB MS [M+1]$^+$ 396.1. The compound was treated with one equivalent of 1 N HCl—Et$_2$O solution and isolated as a HCl salt.

40

EXAMPLE 19

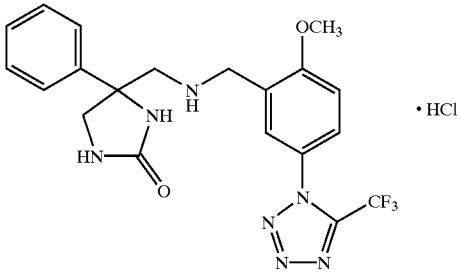

Step 1:

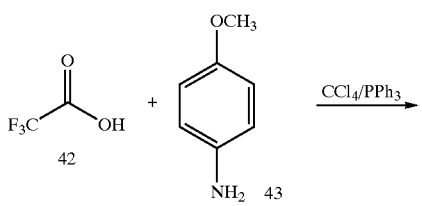

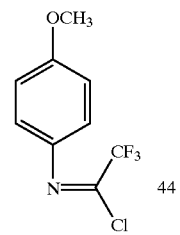

To a solution of triphenyl phosphine (99.5 g, 379.43 mmol) in CCl$_4$ (51 ml), Et$_3$N (16.98 ml, 121.80 mmol) and trifluoro acetic acid, 42, (7.8 ml, 101.08 mmol) were added. After stirring at 0° C. for 10 min, a solution of p-anisidine 43 (15 g, 121.80 mmol) in CCl$_4$ (51 ml) was added. The reaction mixture was refluxed for 3 h. Cooled down to RT, the reaction mixture was filtered and rinsed 10 with hexane until there was no yellow color filtered off. The filtrate was concentrated and the brown residue was distilled at 110° C. to give the desired product 44 (17 g, 71.55 mmol, 59% yield) as a yellow oil.

Step 2:

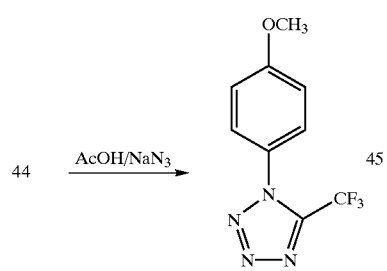

To a solution of compound 44 (7 g, 29.46 mmol) in AcOH (110 ml) was added NaN$_3$ (6.13 g, 94.27 mmol). The reaction mixture was heated at 70° C. overnight. After cooling to RT, the reaction mixture was filtered and the filtrate was diluted with CH$_2$Cl$_2$ (200 ml) and washed with saturated NaHCO$_3$ (100 ml) solution, water (100 ml) and dried over Na$_2$SO$_4$, filtered and concentrated. Compound 45 (7 g, 28.67 mmol, 98% yield) was obtained and used directly without further purification.

Step 3:

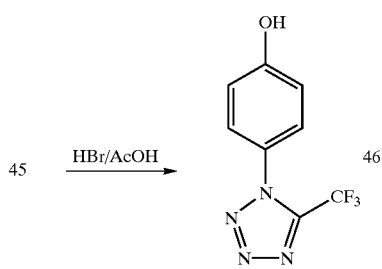

To the flask containing compound 45 (15 g, 61.43 mmol) and AcOH (100 ml) was added 48% aqueous HBr (100 ml). The reaction mixture was heated to 100° C. for 48 h. After cooling to RT, the reaction mixture was concentrated to half of its volume on the rotary evaporator and extracted with EtOAc (200 ml×2). The combined organic layer was washed with water (150 ml×3), dried over $Na_2SO_4$, filtered and concentrated to give 46 (8.0 g, 34.76 mmol, 57% yield) which was used without further purification.

Step 4:

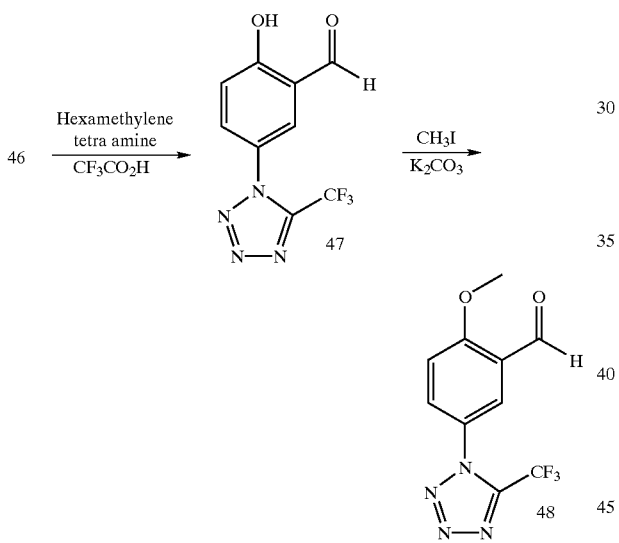

To the solution of phenol 46 (4 g, 17.39 mmol) in TFA (40 ml) was added hexamethylene tetramine (11.2 g, 79.89 mmol). The reaction mixture was heated at 70° C. under a $N_2$ atmosphere for 48 h. Cooled to RT, the reaction mixture was poured into 2 N $H_2SO_4$ (100 ml). This mixture was then extracted with EtOAc (200 ml, 2×), dried over $Na_2SO_4$, filtered and concentrated to give compound 47 (3.4 g, 13.17 mmol, 76% yield) as a crude product which was used in the next step directly.

Compound 47 (3.4 g, 13.17 mmol) was dissolved in anhydrous DMF (20 ml). To this solution was added $K_2CO_3$ (3.6 g, 26.34 mmol) and $CH_3I$ (1.7 ml, 26.34 mmol). The reaction mixture was stirred at RT for 3 h and then poured into a separatory funnel containing water (125 ml) and EtOAc (250 ml). The organic layer was washed with water (100 ml×2), brine (100 ml) and concentrated. The crude product was purified by flash silica gel, eluting with hexane/EtOAc (9:1) to give 48 as a white solid (3 g, 1.02 mmol, 84%)

Step 5:

To a solution of hydrochloride salt of 39 (0.25 g, 1.098 mmol), a (9:1) mixture of trifluoroethanol/$Et_3N$ (20 ml) and aldehyde 48 (0.3 g, 1.098 mmol) was added followed by 3Å molecular sieves (1.5 g). The reaction mixture was stirred under $N_2$ protection for 0.5 h before sodium triacetoxy borohydride (0.81 g, 3.83 mmol) was added. After 18 h of stirring, the reaction was filtered and rinsed with a (1:1) mixture of $CH_3OH$/EtOAc (200 ml). The filtrate was concentrated and purified with flash grade silica gel, eluting with EtOAc/$Et_3N$ (9:1) to give the title compound (0.3 g, 0.67 mmol, 61% yield) FAB MS $(M+1)^+$ 448.1. The compound was treated with one equivalent of 1N HCl—$Et_2O$ solution and isolated as a HCl salt.

EXAMPLE 20

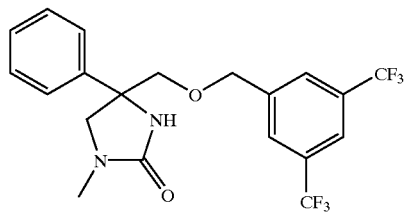

Step 1:

To the solution of hydantoin compound 7 (0.1 g, 0.23 mmol) (Example 1, method 2) in anhydrous DMF (1 ml), $K_2CO_3$ (45 mg, 0.322 mmol) was added. After stirring at RT for 25 min, $CH_3I$ (29 μl, 0.46 mmol) was added. After stirring at RT overnight, the reaction mixture was quenched by pouring into EtOAc (100 ml). The organic layer was washed with a saturated $K_2CO_3$ (100 ml×2) solution, dried over $Na_2SO_4$, filtered and concentrated. The crude product was purified by flash chromatography (EtOAc/hexane 1:4) to give compound 49 as a solid (67 mg, 0.17 mmol, 74% yield). FAB MS $[M+1]^+$ 447.1.

Step 2:

To a 2-neck flask containing $AlCl_3$ (0.37 g, 2.77 mmol), 1 M LAH(2.07 ml, 2.07 mmol) in $Et_2O$ was added slowly. Stirred for a few minutes, a solution of hydantoin 49 (0.31 g, 0.69 mmol) in anhydrous $Et_2O$ (5 ml) was added to the white suspension. The reaction mixture was left at RT for 48 h and quenched by adding water (1 ml), dropwise, followed by 15% NaOH (1 ml). The white precipitate was filtered and rinsed with EtOAc. The filtrate was washed with brine (50 ml), dried over $Na_2SO_4$, filtered and concentrated. The crude product was purified by flash chromatography (2% $CH_3OH$ in $CH_2Cl_2$) and the title compound was isolated as a solid (0.22 g, 0.51 mmol, 74% yield). FAB MS $[M+1]^+$ 433.1.

EXAMPLE 21

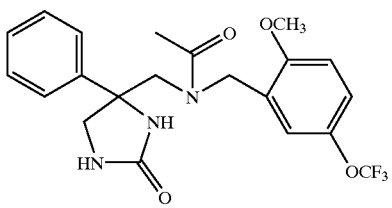

To the mixture of the compound of Example 18 (0.05 g, 0.126 mmol) in CH$_2$Cl$_2$ (2 ml), Et$_3$N (35 μl, 0.252 mmol) and CH$_3$COCl (18 μl, 0.252 mmol) were added. The reaction mixture was left at RT overnight and flashed through silica gel, eluting with EtOAc/Et$_3$N (9:1), to give the title compound as a foam (35 mg, 0.075 mmol, 60% yield). FAB MS [M+1]$^+$ 438.1.

EXAMPLE 22

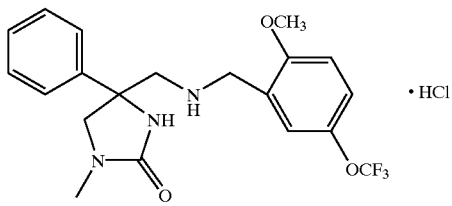

Step 1:

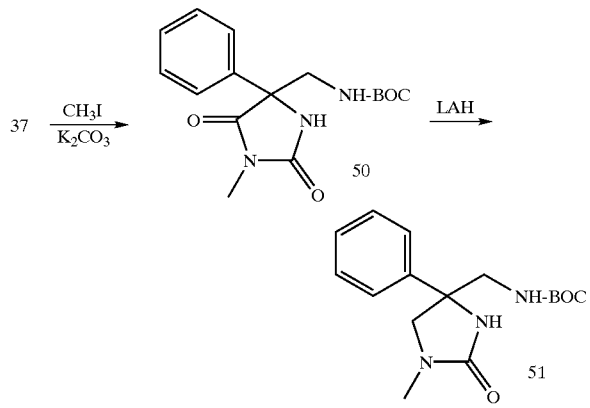

To the solution of 37 (2 g, 6.55 mmol) in anhydrous DMF (12 ml), K$_2$CO$_3$ (1.27 g, 9.19 mmol) was added. After stirring at RT for 0.5 h, CH$_3$I (0.82 ml, 13.17 mmol) was added. After stirring at RT overnight, the reaction was diluted with EtOAc (150 ml) and washed with water (100 ml×2), dried over Na$_2$SO$_4$, filtered, and concentrated to give a white solid as the crude 50. The crude material was further purified on the flash grade silica gel, eluting with 20% EtOAc in hexane to give pure 50 as a solid (1.88 g, 5.89 mmol, 90% yield).

To a cooled flask containing AlCl$_3$ (3.14 g, 23.55 mmol) at 0° C., 1M solution of LAH in anhydrous THF (18 ml 18 mmol) was added slowly. The resulting white slurry was treated with a solution of hydantoin 50 (1.88 g, 5.89 mmol) in anhydrous THF (40 ml). The reaction mixture was stirred at RT for 3 days. Water (2 ml) was added carefully to quench the remaining reactants, followed by 15% NaOH (2 ml) and water (6 ml). The mixture was then poured into a separatory funnel containing EtOAc (200 ml), and the organic layer was washed with water (100 ml×2), dried over Na$_2$SO$_4$, filtered and concentrated. The crude product 51 (1.28 g, 4.19 mmol, 72% yield) was used directly in the next step.

Step 2:

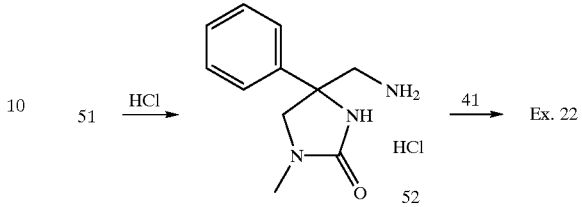

The mixture of BOC compound 51 (1.28 g, 4.19 mmol) in 4 M HCl solution of dioxane (25 ml, 100 mmol) was stirred at RT for 18 h. After completion, all solvents were evaporated off and the residue was dried by azotropical distillation with CH$_3$OH twice. The foamy crude product 52 (0.1 g, 0.487 mmol) was dissolved in a solution of CF$_3$CH$_2$OH/Et$_3$N 9:1 (10 ml). To this clear solution, aldehyde 41 (0.107 g, 0.487 mmol) was added, followed by 3 Å molecular sieves (0.7 g). After stirring at RT for 45 min, NaBH(OAc)$_3$ (0.36 g, 1.7 mmol) was added. The reaction was stirred overnight at RT. After reaction was complete, the mixture was filtered and washed with CH$_3$OH and EtOAc. Evaporation of all solvents gave the title compound as a crude product which was further purified by silica gel chromatography with EtOAc/hexane (1:1) as eluting solvents to give the title compound (80 mg, 0.195 mmol, 40%) as an oil. FAB MS [M+1]$^+$ 410.1.

The compound was treated with one equivalent of 1 N HCl—Et$_2$O solution and isolated as the HCl salt.

EXAMPLE 23

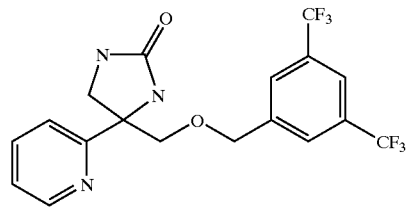

Step 1:

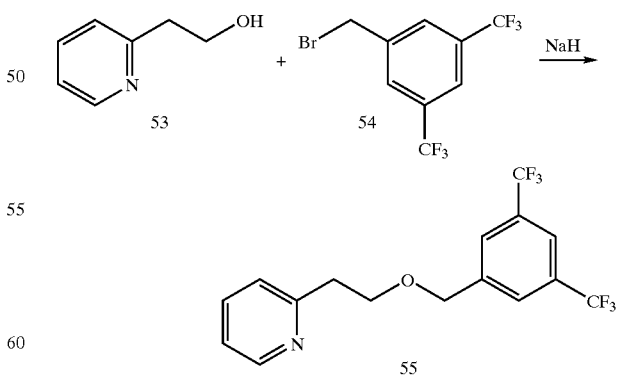

A solution of the alcohol 53 (10 g, 81.2 mmol) in anhydrous DMF (50 ml) was cooled to 0° C. and treated with 60% NaH (3.6 g, 89.3 mmol) in mineral oil portionwise. The cooling bath was removed after 30 min and the reaction was stirred at RT for 2 h. The reaction mixture was cooled again to 0° C. and then treated with bromide 54. After stirring for 4 h, the reaction was quenched by pouring into EtOAc (250 ml). The organic mixture was washed with water (200 ml,×4), brine (50 ml), dried over Na$_2$SO$_4$, filtered and concentrated. The crude product was purified on a Biotage 75 S column, eluting with hexane/EtOAc (5:1) to give 55 (22.2 g, 63.6 mmol, 78% yield). Electrospray MS [M+1]$^+$ 350.1.

Step 2:

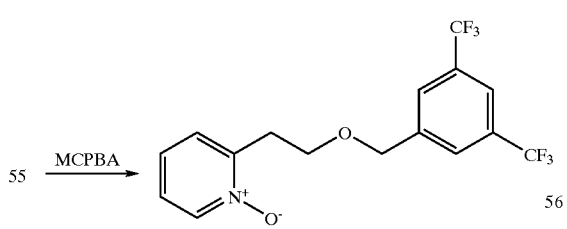

A solution of 55 (10 g, 28.6 mmol) in CH$_2$Cl$_2$ (50 ml) was treated with MCPBA (6.2 g, 28.6 mmol). After 2 h, additional 2 g of MCPBA was added and the mixture was stirred for 6 h. The mixture was poured into EtOAc (250 ml) and washed with saturated aqueous Na$_2$S$_2$O$_3$ (200 ml), saturated aqueous NaHCO$_3$ (200 ml), and brine, dried over Na$_2$SO$_4$, filtered and concentrated to give the N-oxide 56 as a lightly colored solid (10.18 g, 27.9 mmol, 97.5% yield). Electrospray MS [M+1]$^+$ 366.1.

Step 3:

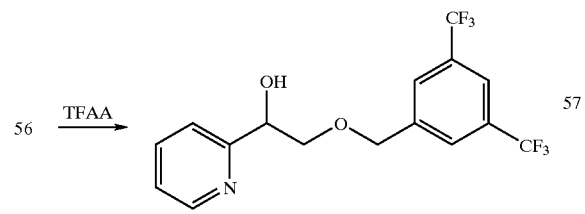

A mixture of N-oxide 56 (6.0 g, 16.43 mmol) and trifluoroacetic anhydride (17.3 g, 82. 2 mmol) in CH$_2$Cl$_2$ (75 ml) was heated under reflux for 4 h and then stirred at RT overnight. The reaction mixture was concentrated in vacuo. The residue was dissolved in THF (40 ml) and saturated aqueous NaHCO$_3$ was added until gas no longer evolved. EtOAc (200 ml) and brine (200 ml) were added and the organic phase was separated. The aqueous phase was extracted with EtOAc (150 ml,×2). The combined organic layers were washed with brine (200 ml), dried over Na$_2$SO$_4$, filtered and concentrated to give a crude orange oil, which was further purified on the Biotage column, eluting with hexane/EtOAc (4:1) to give 57 (4.11 g, 11.26 mmol, 68.5% yield). Electrospray MS [M+1]$^+$ 366.9.

Step 4:

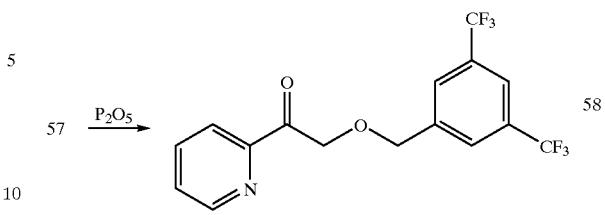

CH$_2$Cl$_2$ (100 ml) was added to a solution of alcohol 57 (4.11 g, 11.25 mmol) in warm DMSO (11 ml). The solution was cooled to 0° C. and P$_2$O$_5$(6.39 g, 22.5 mmol) was then added portionwise over 30 min, followed by addition of Et$_3$N (6.3 ml, 45 mmol). The reaction mixture was stirred at RT for 18 h, then quenched with saturated aqueous NaHCO$_3$. The aqueous layer was extracted with EtOAc (200 ml,×3). The combined organic phases were washed with brine (200 ml), dried over Na$_2$SO$_4$, filtered and concentrated. The crude product was triturated with hexane to give a light tan powder as desired product. The filtrate was further purified on the Biotage column, eluting with hexane/EtOAc (4:1) to give 58 as tan solid (2.46 g, 6.74 mmol, 60.25%). Electrospray MS [M+1]$^+$ 364.1.

Step 5:

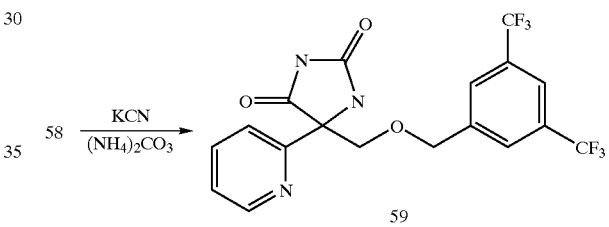

A suspension of ketone 58 (2.30 g, 6.30 mmol) in a mixture of (1:1) water/EtOAc (30 ml) was treated with (NH$_4$)$_2$CO$_3$ (2.12 g, 22.1 mmol) followed by KCN(0.62 g, 9.5 mmol). The solution was heated to 60° C. and stirred overnight. After cooling to RT, the reaction mixture was taken up in EtOAc (100 ml) and washed with water (100 ml×2). The separated organic layer was dried over Na$_2$SO$_4$, filtered and concentrated in vacuo. The crude product was purified on a Biotage column, eluting with hexane/EtOAc (1:1) to give the desired product 59 as a white solid ( 2.03 g, 4.69 mmol,. 74.5% yield). Electrospray MS [M+1]$^+$ 434.1.

Step 6:

To a cooled flask containing AlCl$_3$ (614 mg, 4.6 mmol) at 0° C., a 1M solution of LAH in Et$_2$O (3.5 ml, 3.5 mmol) was added dropwise. 10 min later, a solution of hydantoin 59 (500 mg, 1.15 mmol) in anhydrous THF (10 ml) was added slowly. After 25 min at 0° C., the reaction was complete as determined by TLC. Water (3 ml) was added slowly to the reaction mixture, followed by 15% NaOH (3 ml) and water (9 ml). After stirring at RT for 15 min, the emulsion was filtered and rinsed with EtOAc and THF. The filtrate was washed with water (50 ml), dried over Na$_2$SO$_4$, filtered and concentrated. The crude product was purified on the Biotage column, eluting with EtOAc/Et$_3$N (9:1) to give the title compound as a solid (0.229 g, 0.546 mmol, 47.5% yield). Electrospray MS [M+1]$^+$ 420.1.

EXAMPLE 24

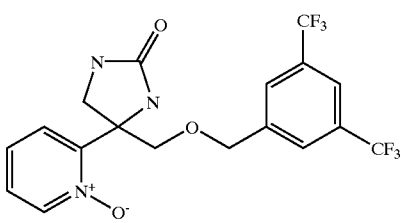

The title compound was prepared by a similar method to that described in Example 23, Step 2, using the cyclic urea, 56, of Example 23 in place of ether 55. Yield was 67.1%. Electrospray MS [M+1]$^+$ 436.1.

EXAMPLE 25

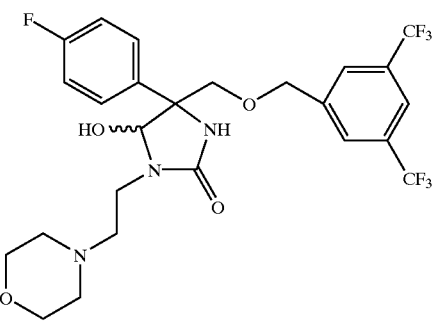

Step 1:

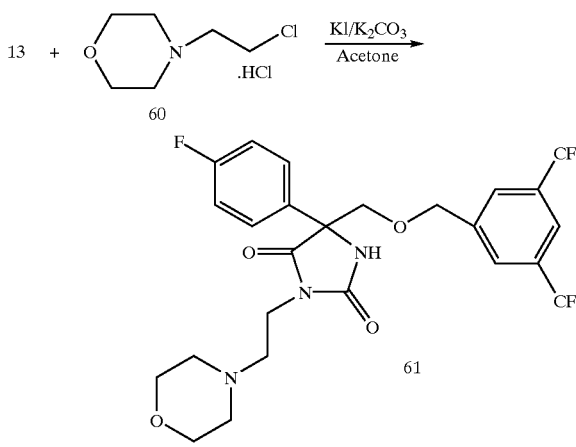

To the flask containing compound 13 (1.35 g, 3 mmol) in acetone (45 ml), 4-(2-chloroethyl)morpholine hydrochloride salt, 60, (0.614 g, 3.3 mmol) was added, followed by KI (0.1 g, 0.6 mmol) and K$_2$CO$_3$ (1.24 g, 9 mmol). The reaction mixture was heated to reflux for 44 h. After cooling to RT, EtOAc (60 ml) was added and the organic mixture was washed with water (20 ml), dried over MgSO$_4$, filtered and concentrated to give 61 as an oil. The crude product was further purified on a silica gel column, eluting with 20% EtOAc/CH$_2$Cl$_2$ to give 61 (1.3 g, 2.3 mmol, 76% of yield).

Step 2:

To a cooled flask containing AlCl$_3$ (0.35 g, 2.63 mmol) at 0 IC under a N$_2$ atmosphere, 1 M solution of LAH in Et$_2$O (2.0 ml, 2.0 mmol) was added dropwise. Stirred for 5 min, a solution of 61 (0.37 g, 0.66 mmol) in anhydrous THF (10 ml) was added slowly. The reaction mixture was allowed to stir from 0° C. to RT over the weekend and quenched with 20% NaOH (1 ml). The solids were filtered and rinsed well with CH$_2$Cl$_2$ after stirring for 15 min. The filtrate was concentrated and purified on flash grade silica gel, eluting with 5% CH$_3$OH in CH$_2$Cl$_2$ to give the title compound as a white foam (70 mg, 0.13 mmol, 20% of yield). High Resolution MS: [M+1]$^+$measured 566.1899, calculated 566.1890.

EXAMPLE 26

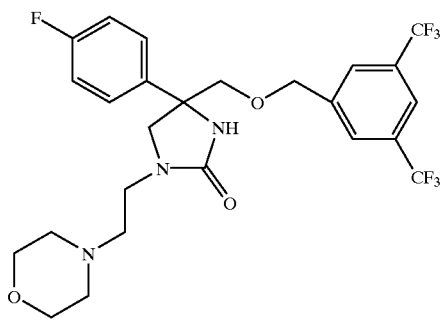

To a cooled flask containing AlCl$_3$ (1.23 g, 9.24 mmol) at 0° C. under N$_2$ atmosphere, 1 M solution of LAH in Et$_2$O (7.0 ml, 7.0 mmol) was added dropwise. Stirred for 5 min, a solution of 61 (1.3 g, 2.3 mmol) in anhydrous THF (25 ml) was added slowly. The reaction mixture was allowed to stir at 0° C. for 15 min then heated at 70° C. for 64 h. The reaction was quenched with 20% NaOH (2 ml) and stirred at RT for 15 min. The solids were filtered and rinsed well with CH$_2$Cl$_2$. The filtrate was concentrated and purified on flash grade silica gel, eluting with 5% CH$_3$OH in CH$_2$Cl$_2$ to give the title compound as a gummy solid (0.46 g, 0.8 mmol, 36% yield). High Resolution MS: [M+1]$^+$ measured 550.1948, calculated 550.1941.

EXAMPLE 27

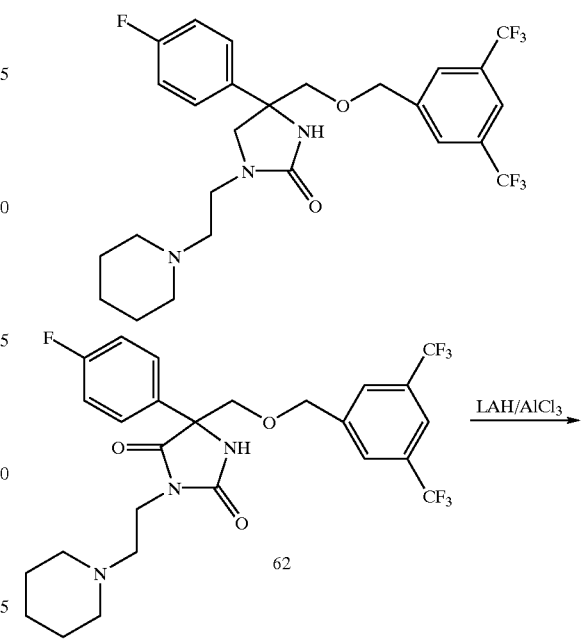

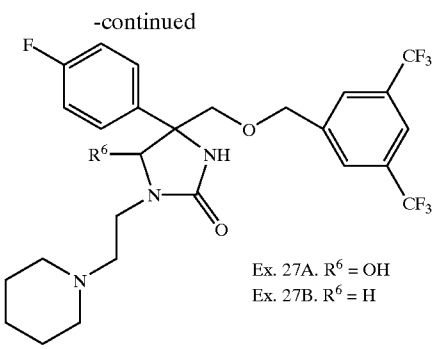

Ex. 27A. R⁶ = OH
Ex. 27B. R⁶ = H

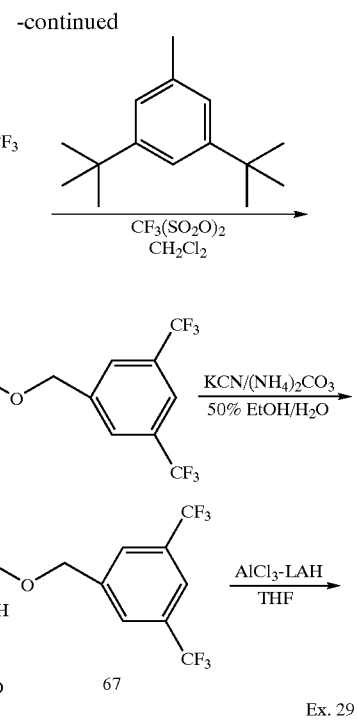

Ex. 29

Compound 62 was prepared in a similar method as described in Example 25 using 2-chlorethyl-1-piperidine in place of 4-(2-chloroethyl)-morpholine. A mixture of Ex. 27A and Ex. 27B was separated by flash column chromatography, eluting with 2~5% CH₃OH in CH₂Cl₂ to afford Ex. 27A (33% yield) (FAB MS [M+1]⁺ 564) and Ex. 27B (43% yield) FAB MS [M+1]⁺ 549.

EXAMPLE 28

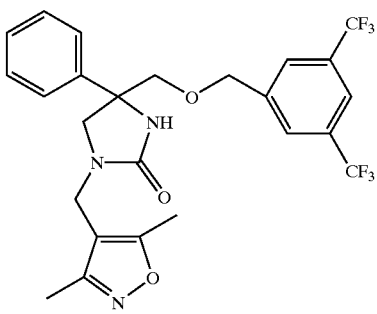

The title compound was prepared by an analogous method to that described in Example 16 using the compound of Example 1 in place of the compound of Example 11 to give the title compound in a 22% yield. FAB MS [M+1]⁺ 546.3.

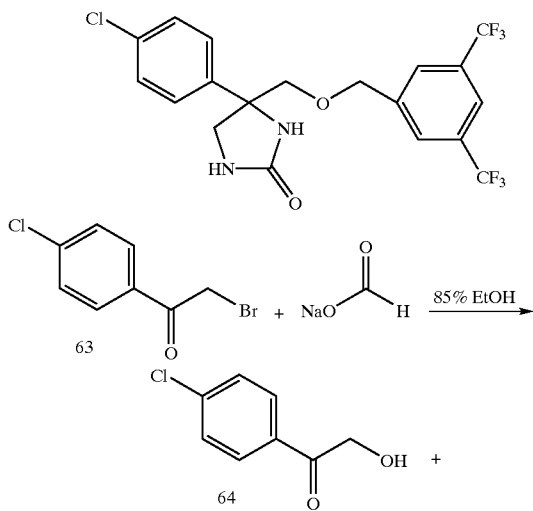

The title compound was prepared by analogous methods as described for Examples 1 and 2, except for the preparation of ketone intermediate 66. Compound 66 was prepared by treatment of compound 64 (24.1 g, 98.8 mmol) and 2,6-di-t-butyl-4-methyl pyridine (42 g, 206 mmol) in dry CH₂Cl₂ (400 ml) at 0° C. with slow addition of trifluoromethyl-methane sulfonic anhydride (30 g, 107 mmol) under a N₂ atmosphere. After stirring at RT for 1 h, a solution of compound 64 (14 g, 82.3 mmol) in CH₂Cl₂ (200 ml) was added dropwise. After stirring at RT for 6 days, the solid was filtered and filtrate was washed with brine, dried (MgSO₄), filtered and concentrated to give a crude 66 as a brown oil. Compound 66 was obtained by purification through a flash grade silica gel, eluting with 8% EtOAc/hexane to give 66 as an oil (19.5 g, 50 mmol, 61% of yield). Compound 67 was synthesized from compound 66 with a 60% of yield and title compound was prepared from 67 by selective reduction with AlCl₃—LAH in a 52% yield. FAB MS [M+1]⁺ 467.

EXAMPLE 30

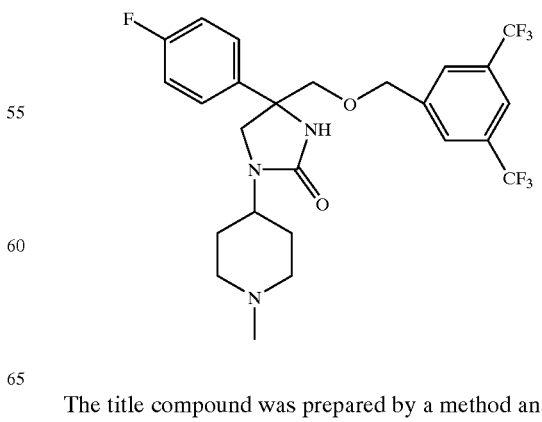

The title compound was prepared by a method analogous to that described in Example 7 by using compound 22 and replacing tetrahydro-4 H-pyranone with 1 methyl-4-piperidone. HRMS [M+1]+ calculated, 534.1992; found, 534.1987.

EXAMPLE 31

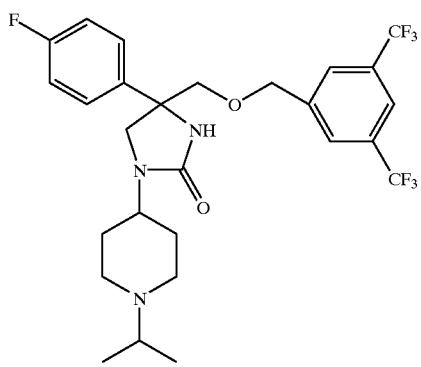

To a solution of the product of Example 10 (0.2 g, 0.36 mmol) in dichloroethane (3 ml) and acetone (21 mg, 0.36 mmol) at RT was added Na(OAc)$_3$BH (0.15 g, 0.72 mmol). The mixture was stirred at RT for two days under a N$_2$ atmosphere. After completion, to the reaction was added CH$_2$Cl$_2$ (50 ml) and saturated NaHCO$_3$ solution, followed by routine work-up to give a crude product. Product was purified on flash grade silica gel, eluting with 3% NH$_4$OH—CH$_3$OH (1:9)/97% CH$_2$Cl$_2$ to afford pure title compound as a solid (0.12 g, 0.22 mmol) in a 62% of yield. FAB MS [M+1]+ 562.4.

EXAMPLE 32

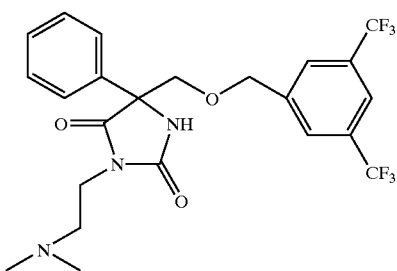

The title compound was prepared by a method analogous to that described in Example 25 for compound 61 in step 1, using compound 7 in place of compound 13 and N,N-dimethyaminoethyl chloride hydrochloride in place of 1-(2-chloro-ethyl)-morpholine hydrochloride. The title compound was obtained as a solid in a 96% yield. Electrospray MS [M+1]+ 504.1.

EXAMPLE 33

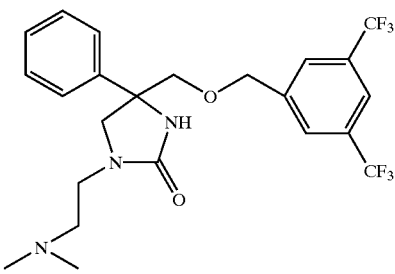

Reduction of the compound from Example 32 with LAH-ALCl$_3$ complex, analogous to the method described in Example 26, gave the title compound in a 32% yield. Electrospray MS [M+1]+ 490.1.

EXAMPLE 34

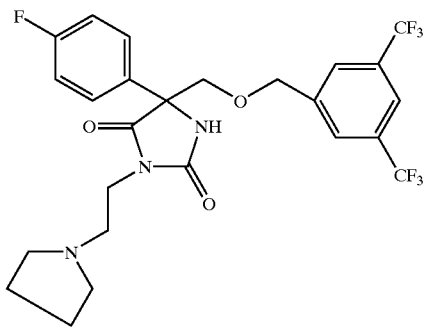

The title compound was prepared by an analogous method to that described in Example 25, Step 1, using 1-(2-chloroethyl)pyrrolidine HCl salt in place of 1-(2-chloroethyl)-morpholine hydrochloride salt. The title compound was obtained as a solid in a 77% yield. Electrospray MS [M+1]+ 548.1.

EXAMPLE 35

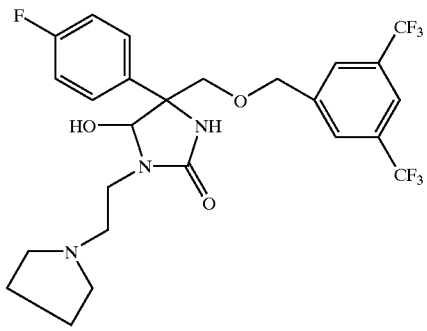

Reduction of compound the product of Example 34 with LAH—ALCl$_3$ complex as described in Example 26, heating at 70° C. for 1 day, gave the title compound in a 36% yield. Electrospray MS [M+1]+ 550.1

EXAMPLE 36

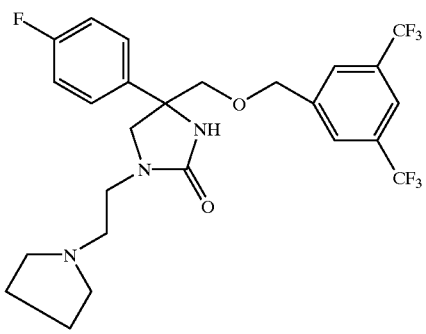

Reduction of the product of Example 34 with LAH-ALCl₃ complex at 70° C. for 1 day, analogous to the method as described in Example 26, gave the title compound in a 11% yield. Electrospray MS [M+1]⁺ 534.1.

EXAMPLE 37

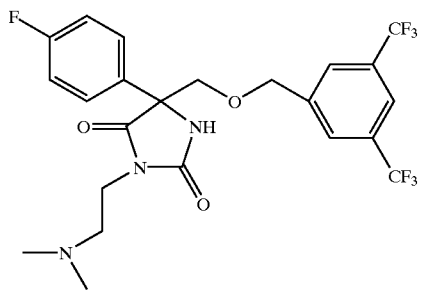

The title compound was prepared by an analogous method to that described in Example 25, Step 1, using 2-dimethylamine ethyl chloride hydrochloride salt in place of 1-(2-chloroethyl)-morpholine hydrochloride salt. The title compound was obtained as a solid in a 83% of yield. Electrospray MS [M+1]⁺ 522.1.

EXAMPLE 38

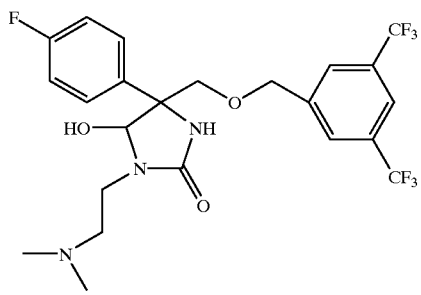

Reduction of the product of Example 37 with LAH-ALCl₃ complex at 70° C. for 1 day, analogous to the method described in Example 26, gave the title compound in a 26% yield. Electrospray MS [M+1]⁺ 524.1

EXAMPLE 39

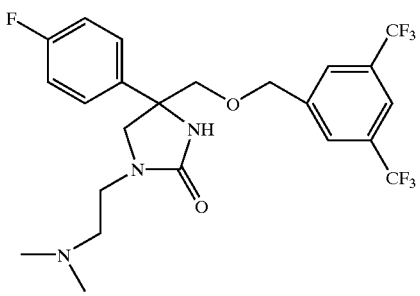

Reduction of the product of Example 38 with LAH—ALCl₃ complex at 70° C. for 1 day, analogous to the method described in Example 26, gave the title compound in a 15% yield. Electrospray MS [M+1]⁺ 508.1.

EXAMPLE 40

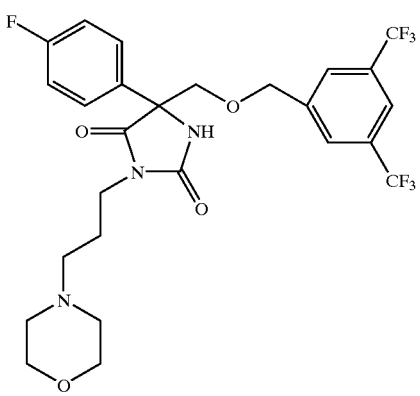

The title compound was prepared by an analogous method to that described in Example 25, Step 1, using 3-chloropropyl-morpholine in place of 1-(2-chloroethyl) morpholine hydrochloride. The title compound was obtained as a solid in a 57% yield. FAB MS [M+1]⁺ 578.1.

EXAMPLE 41

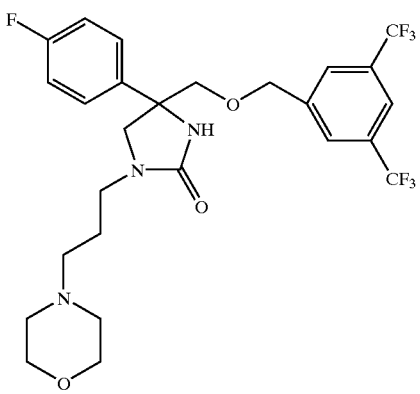

Reduction of the compound from Example 40 with LAH—ALCl₃ complex, analogous to the method as described in Example 26, gave the title compound in a 9% yield. Electrospray MS [M+1]⁺ 564.1.

EXAMPLE 42

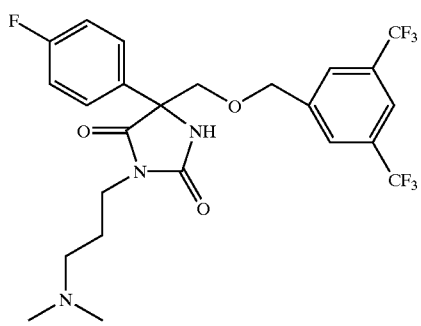

The title compound was prepared by an analogous method to that described in Example 25, Step 1, using N,N-dimethylaminopropyl chloride HCl in place of 1-(2-chloroethyl)-morpholine hydrochloride. The title compound was obtained as a solid in a 69% yield. FAB MS [M+1]$^+$ 536.1.

EXAMPLE 43

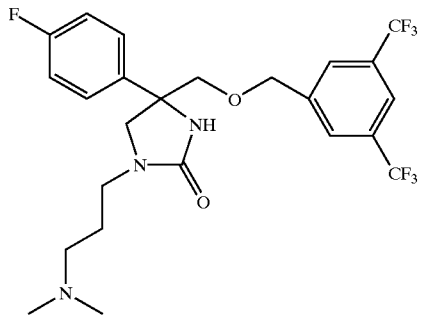

Reduction of the compound from Example 42 with LAH—ALCl$_3$ complex, analogous to the method as described in Example 26, gave the title compound in a 1.5% yield. Electrospray MS [M+1]$^+$ 522.3.

EXAMPLE 44

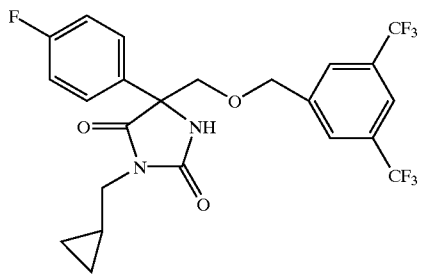

The title compound was prepared by an analogous method to that described in Example 25, Step 1, using bromomethyl cyclopropane replacing 1-(2-chloroethyl)-morpholine hydrochloride. The title compound was obtained as a solid in a 94% of yield. FAB MS [M+1]$^+$ 505.1.

EXAMPLE 45

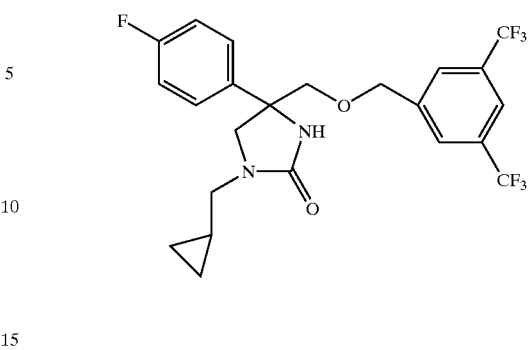

Reduction of the compound from Example 44 with LAH—ALCl$_3$ complex, analogous to the method as described in Example 26, gave the title compound in a 57% yield. Electrospray MS [M+1]$^+$ 491.1.

EXAMPLE 46

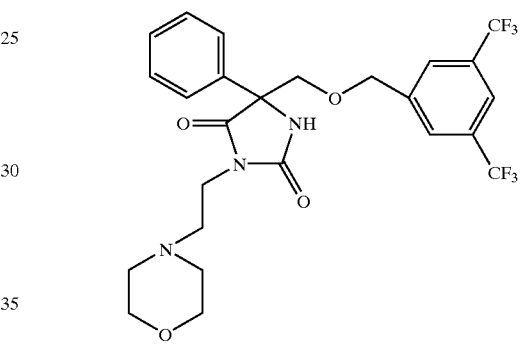

The title compound was prepared by an analogous method to that described in Example 25, Step 1, using compound 7 in place of compound 13. The title compound was obtained as a solid in a 90% yield. FAB MS [M+1]$^+$ 546.1.

EXAMPLE 47

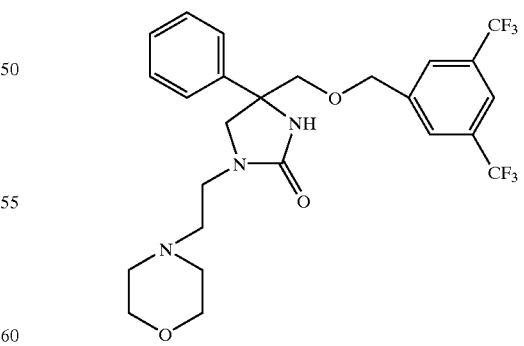

Reduction of the compound from Example 46 with LAH—ALCl$_3$ complex, analogous to the method as described in Example 26, gave the title compound in a 67% yield. Electrospray MS [M+1]$^+$ 532.1.

EXAMPLE 48

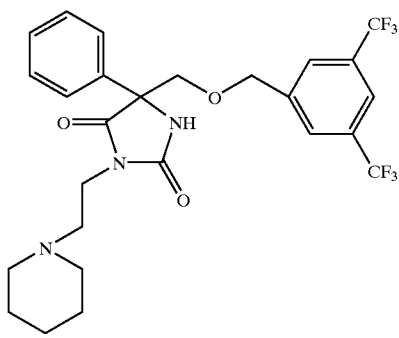

The title compound was prepared by an analogous method to that described in Example 25, Step 1, using compound 7 in place of compound 13 and 1-(2-chloroethyl)-piperidine hydrochloride in place of 1-(2-chloroethyl)-morpholine hydrochloride. The title compound was obtained as a solid in a 90% yield. FAB MS [M+1]+ 544.3.

EXAMPLE 49

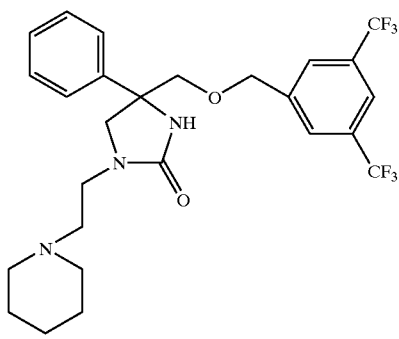

Reduction of the compound from Example 48 with LAH—ALCl$_3$ complex, analogous to the method as described for Example 26, gave the title compound in a 52% yield. Electrospray MS [M+1]+ 530.1.

EXAMPLE 50

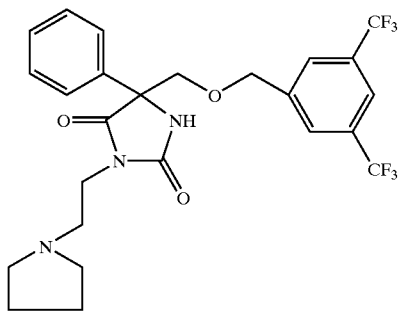

The title compound was prepared by an analogous method to that described in Example 25, Step 1, using compound 7 in place of compound 13 and 1-(2-chloroethyl)-pyrrolidine hydrochloride in place of 1-(2-chloroethyl)-morpholine hydrochloride. The title compound was obtained as a solid in a 76% yield. Electrospray MS [M+1]+ 530.1.

EXAMPLE 51

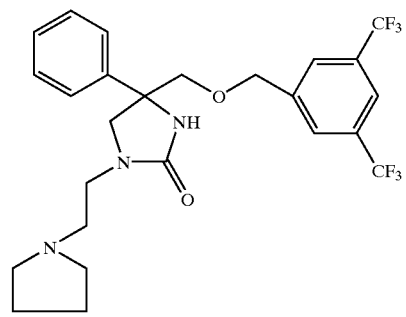

Reduction of the compound from Example 50 with LAH—ALCl$_3$ complex, analogous to the method as described in Example 26, gave the title compound in a 65% yield. Electrospray MS [M+1]+ 516.1.

EXAMPLE 52

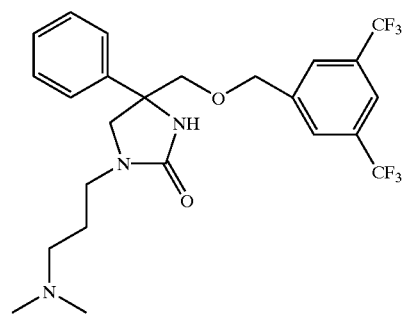

The title compound was prepared by a method analogous to Example 42, using 7 in place of 13. Reduction of the resulting hydantoin with LAH/AlCl$_3$ complex, analogous to the method described in Example 26, gave the title compound in 8% yield. FAB MS [M+1] 504.1.

EXAMPLE 53

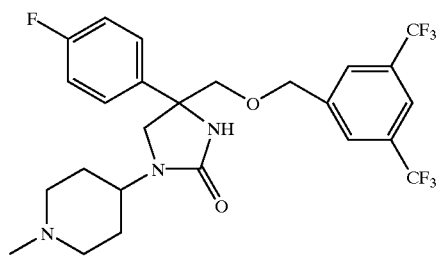

The title compound was prepared by a method analogous to that described in Example 7, using N-methylpiperidone in place of tetrahydro-4H-pyranone. The title compound was obtained as a solid in a 28% yield. FAB MS [M+1] 534.

EXAMPLE 54

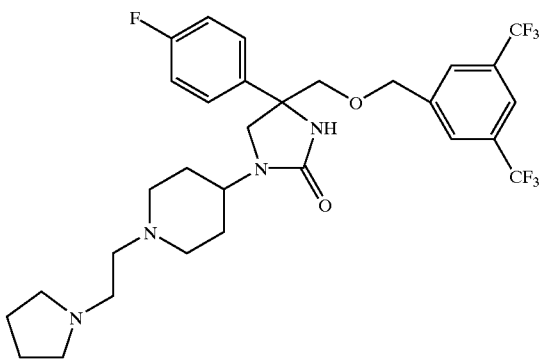

A solution of the product of Example 10 (0.3 g, 0.54 mmol) in CH$_2$Cl$_2$ (3 ml), N, N-diisopropylethylamine (0.24 g, 1.9 mmol), and 1-(2-chloroethyl)pyrrolidine hydrochloride (92 mg, 0.54 mmol) was stirred under an atmosphere of N$_2$ at RT for 14 days. After work-up, a cloudy gum was obtained as a crude product which was purified by chromatography, eluting with 4.5% NH$_3$—CH$_3$OH (1:9)/95.5% CH$_2$Cl$_2$ to give the title compound as an off-white solid (20 mg, 7%). FAB MS [M+1] 617.1.

EXAMPLE 55

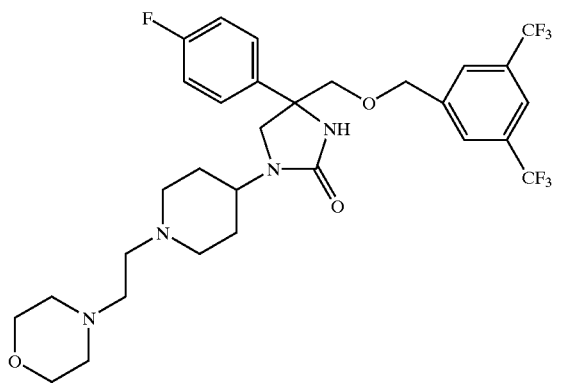

The title compound was prepared by a method analogous to Example 54, using 4-(2-chloroethyl)morpholine in place of 1-(2-chloroethyl)pyrrolidine. The title compound was obtained as a solid in a 35% yield. FAB MS [M+1] 633.3.

EXAMPLE 56

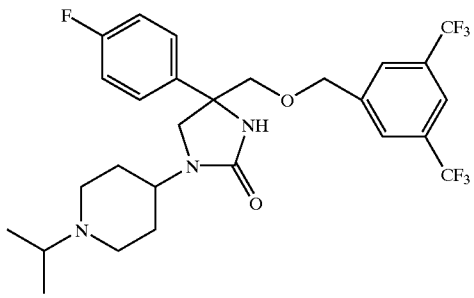

A solution of the product of Example 10 (0.2 g, 0.36 mmol) in 1, 2 -dichloroethane (3 ml), acetone (21 mg, 0.36 mmol), and Na(OAc)$_3$BH (0.15 g, 0.72 mmol) was stirred under N$_2$ atmosphere at RT for 2 days. After work-up, a solid was obtained as a crude product which was then purified by chromatography, eluting with 3% NH$_3$—CH$_3$OH (1:9)/97% CH$_2$Cl$_2$ to give the title compound as a white solid (120 mg, 60%). FAB MS [M+1] 562.4.

EXAMPLE 57

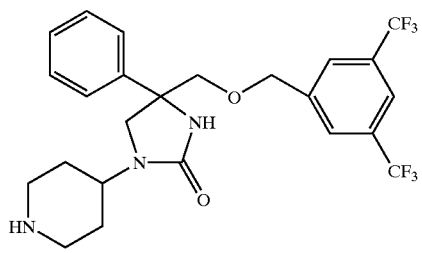

The title compound was prepared by a method analogous to Example 10, using 6 in place of 22. The title compound was obtained as a HCl salt, FAB MS [M+1] 502.1.

EXAMPLE 58

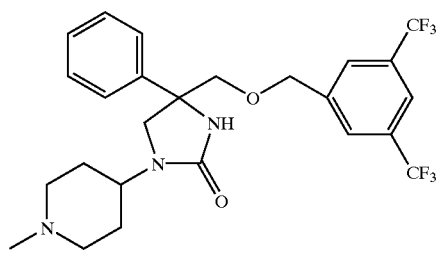

A solution of the product of Example 57 (0.3 g, 0.56 mmol) in CH$_2$Cl$_2$ (3 ml), N, N-diisopropylethylamine (0.14 g, 1.12 mmol), and CH$_3$I (71 mg, 0.5 mmol) was stirred under N$_2$ atmosphere at 0° C. for 2 h. After work-up, a solid was obtained as a crude product which was then purified by chromatography, eluting with 3.5% NH$_3$—CH$_3$OH (1:9)/96.5% CH$_2$Cl$_2$ to give the title compound as a white solid (90 mg, 36%). FAB MS [M+1] 516.1.

EXAMPLE 59

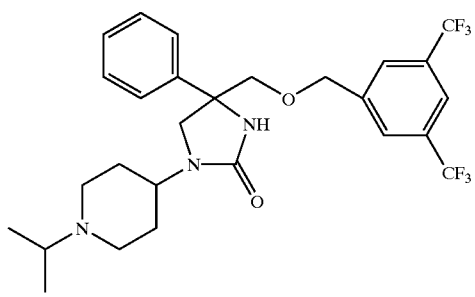

The title compound was prepared by a method analogous to Example 56, using the product of Example 57 in place of Example 10. The title compound was obtained as a solid in a 52% yield. FAB MS [M+1] 544.2.

EXAMPLE 60

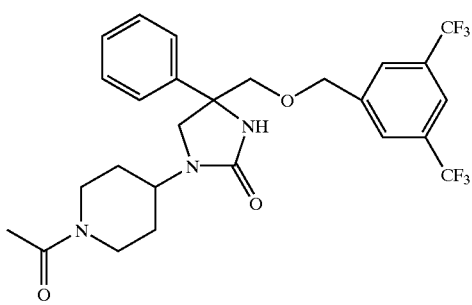

The title compound was prepared by a method analogous to Example 15, using Example 57 in place of Example 14. The title compound was obtained as a solid in a 80% yield. FAB MS [M+1] 544.1.

EXAMPLE 61

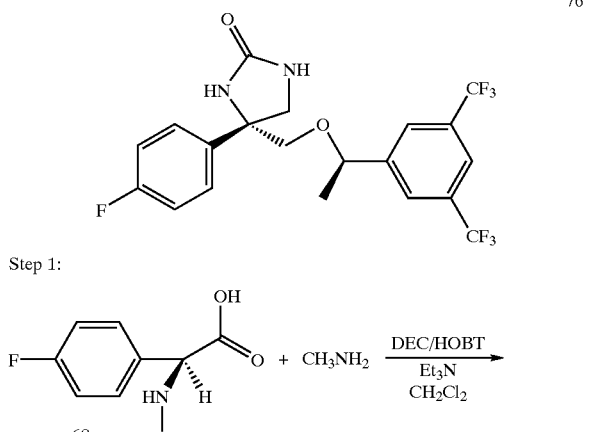

Step 1:

To a cooled solution of (S)-N-tBoc-4-fluoro-phenyl glycine in anhydrous $CH_2Cl_2$ at 0° C., HOBT (3.66 g, 22.4 mmol), $Et_3N$ (3.12 ml, 22.4 mmol), DEC (4.29 g, 22.4 mmol) and 2M $CH_3NH_2$ in THF (10.23 ml, 20.46 mmol) were added. After stirring at 0° C. for 30 min, the reaction mixture was gradually warmed up to RT under $N_2$ protection over night. Diluted with $CH_2Cl_2$ (300 ml), the reaction mixture was washed with 10% citric acid (2×100 ml), saturated $NaHCO_3$—NaCl solution (2×100 ml), brine (1×100 ml). The combined organic layer was dried over $MgSO_4$, filtered and concentrated in vacuo to give crude 69 (4.88 g).

Step 2:

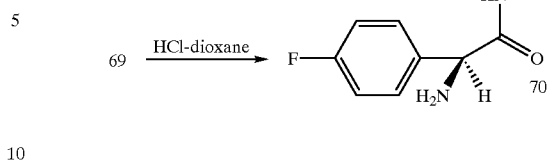

To a cooled solution of 69 (24.3 g, 86 mmol) in $CH_2Cl_2$ (58.8 ml) and $CH_3OH$ (30 ml) at 0° C. was added 4 M HCl-dioxane solution (200 ml, 800 mmol). The clear solution was kept at 0° C. for 2.5 hours. Solvent was evaporated and the solid material was taken up with distilled water (200 ml), neutralized with NaOH (3.4 g) in water (100 ml). Final pH was adjusted to 9.5 with $K_2CO_3$. This aqueous solution was extracted with $CH_2Cl_2$ (4×250 ml). The combined organic layer was dried over $MgSO_4$, filtered and concentrated in vacuo to give a white solid which further turned into a pale yellow solid 70. (14.9 g, 96%).

Step 3:

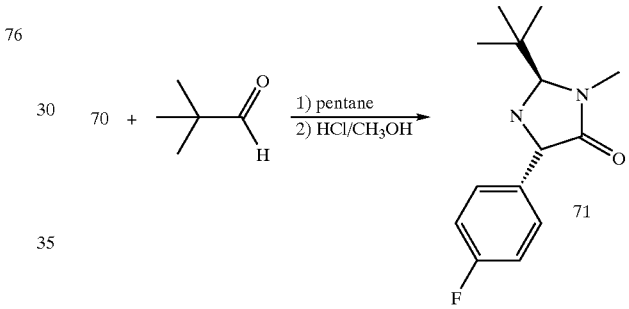

A mixture of compound 70 (14.84 g, 81.5 mmol), pentane (85 ml) and pivaldehyde (11.13 ml, 101.88 mmol) was heated to 65° C. with a Dean-Stark trap for 2.5 hours under $N_2$. The reaction mixture was then concentrated and the crude oil was taken up with $CH_3OH$ (22.5 ml), cooled down to 0° C., and the crude product was treated with saturated HCl—$CH_3OH$ (52.5 ml) through a dropping funnel over 20 min. and stirred at ambient temperature over night. Volatile solvent was again evaporated and the residue was suspended in a mixture of brine (100 ml) and 2% $K_2CO_3$ solution (150 ml). This basic solution (pH=9.5) was extracted with $CH_2Cl_2$ (4×200 ml) and the combined organic layer was dried over $MgSO_4$, filtered and concentrated in vacuo. The crude product (20 g) was purified on a silica gel column, eluting with 25% EtOAc in hexane (4 l), 30% EtOAc in hexane (4 l) to give compound 71 (11.67 g, 58%) as an oil.

Step 4:

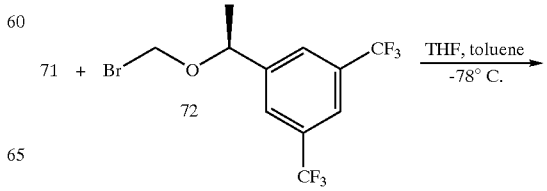

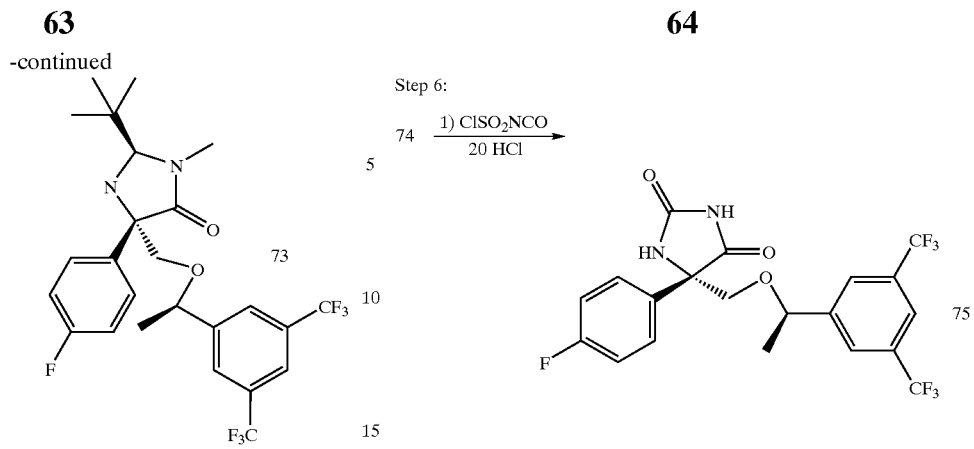

Step 6:

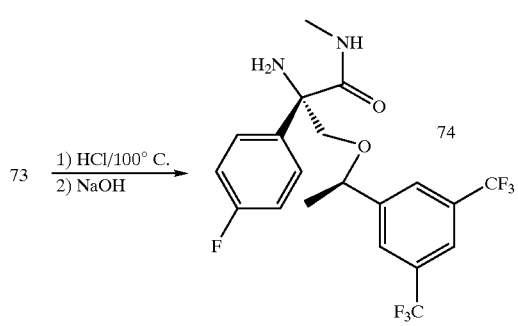

To a cooled solution of 71 (11.5 g, 46.08 mmol) in freshly distilled degassed THF (62 ml) and anhydrous degassed toluene (192 ml) at −78° C., 0.5M KHMDS (97 ml, 48.5 mmol) in toluene was added slowly over 10 min through an addition funnel. The solution was stirred at −78° C. for 40 min before 72 (17 g, 49 mmol) was added via a syringe. Kept stirring at this low temperature for another 2.5 hours, the reaction was quenched with saturated NH$_4$Cl solution (350 ml). The separated aqueous layer was extracted with CH$_2$Cl$_2$ (3×200 ml). The combined organic layer was dried over MgSO$_4$, filtered and concentrated. The crude product was further purified by flash chromatography, eluting with 15% EtOAc in hexane (6 l), 20% EtOAc in hexane (4 l). 73 was obtained as an oil (13.06 g, 56%).

Step 5:

A mixture of 73 (12.55 g, 24.2 mmol) and 6 N HCl (132 ml) was heated to 100° C. under N$_2$ for 4 h. After cooling to RT, volatile solvent was evaporated. The gummy material was redissolved in 2.5% K$_2$CO$_3$ solution (300 ml) and brine (100 ml). The aqueous solution was extracted with CH$_2$Cl$_2$ (4×250 ml). The combined organic layer was dried over MgSO$_4$, filtered and concentrated in vacuo to give a gummy material (10.9 g) which was purified on a silica gel column, eluting with 20% EtOAc in hexane then 1.5% NH$_3$—CH$_3$OH in CH$_2$Cl$_2$. 74 was obtained as an oil (8.45 g, 78%).

To a cooled solution of 74 (7.5 g, 16.6 mmol) in anhydrous CH$_2$Cl$_2$ (85 ml) at 0° C. was added ClSO$_2$NCO (1.45 ml, 16.6 mmol) using a syringe. After stirring for 20 min, the reaction was finished and the solvent was evaporated. Taken up with 1,4-dioxane (70 ml) and 4 N HCl (70 ml), the reaction mixture was then heated up to 95° C. under N$_2$ for 4.5 hours. TLC showed completed reaction. Evaporation of volatile solvents yielded crude gummy material, which was taken up with 2.5% K$_2$CO$_3$ solution (300 ml) and CH$_2$Cl$_2$ (200 ml). The aqueous solution was extracted with CH$_2$Cl$_2$ (4×200 ml). The combined organic layer was dried over MgSO$_4$, filtered and concentrated. The crude product was purified by flash chromatography, eluting with 3.5% (1:9) NH$_4$OH—CH$_3$OH in CH$_2$Cl$_2$ to give 75 as a solid (6.88 g, 90%). Step 7:

To a cooled flask containing AlCl$_3$ (4.3 g, 32.16 mmol) was added LAH (24.12 ml, 24.12 mmol) at 0° C. under N$_2$. After 15 min, a solution of 75 (3.73 g, 8.04 mmol) in anhydrous THF (126 ml) was added through a syringe. The reaction mixture was stirred at 0° C. for 10 min before warming up to RT. After 4 h, the reaction was quenched with saturated Na$_2$SO$_4$ solution (10 ml) in an ice-bath. Diluted with THF (200 ml) and stirred for 1 h at RT, the reaction was dried over MgSO$_4$, filtered and concentrated to give crude 76 (3.5 g), which was purified by flash chromatography eluting with 1% NH$_4$OH/CH$_3$OH (1:9) in CH$_2$Cl$_2$. mp 136–137° C., FABMS [M+1]$^+$ 451.1; [α]$_D$20° C.−49.4° C.

EXAMPLE 62

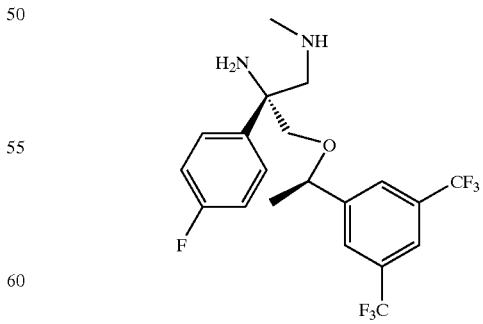

The title compound was prepared by a method analogous to step 7 of Example 61, using compound 74 in place of compound 75. FAB MS [M+1]$^+$ 439.1.

EXAMPLE 63

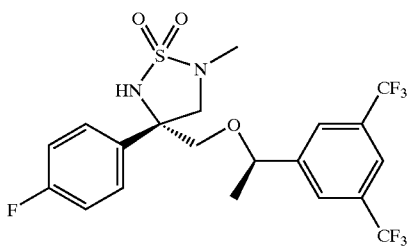

To a solution of Example 62 (180 mg, 0.41 mmol) in dioxane (4 ml), sulfamide (48.5 mg, 0.51 mmol) was added. After heating to 110° C. for 5 h, the reaction was concentrated. The residue was purified by flash chromatography, eluting with 4% $NH_4OH:CH_3OH(1:9)$ in $CH_2Cl_2$. The title compound was collected as off-white solid (35 mg, 17%). FAB MS $[M+1]^+$ 518.1.

EXAMPLE 64

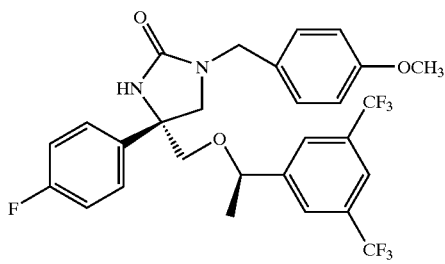

To a cooled solution of NaH (27 mg, 0.67 mmol) in anhydrous DMF (5 ml), was added compound 76 from Example 61 (0.25 g, 0.56 mmol) at 0° C. After 15 min, the cold bath was removed. The reaction was warmed to RT for 45 min before p-methoxy benzyl-chloride (0.08 ml, 0.59 mmol) was added. The reaction was then stirred at RT for another 2 h. Water was used to quench the reaction and the aqueous solution was extracted with EtOAc. The combined organic layer was dried over $Na_2SO_4$, filtered and concentrated. Crude material was purified through a silica gel column, eluting with 2:1 hexane to EtOAc to give the title compound as a solid (86.8 mg, 27%). FAB MS $[M+1]^+$ 571.1.

EXAMPLE 65

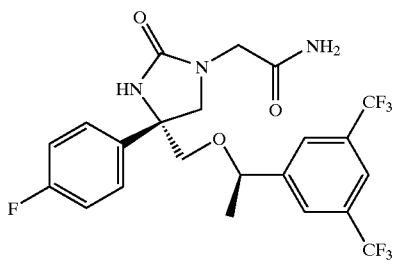

The title compound was prepared by a method analogous to Example 64, using bromo acetamide in place of p-methoxy benzyl chloride. FAB MS $[M+1]^+$ 508.1.

EXAMPLE 66

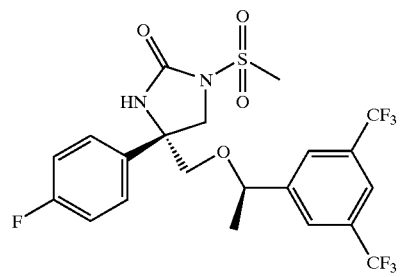

To a cooled solution of 76 (0.2 g, 0.44 mmol) in anhydrous $CH_2Cl_2$ (4.2 ml) at 0° C., diethylisopropylamine (0.12 ml, 0.69 mmol) was added dropwise followed by $CH_3SO_2Cl$ (0.04 ml, 0.52 mmol). The reaction was warmed to RT and stirred overnight. The volatile solvent was evaporated and the crude product was purified on silica gel column, eluting with 4% $CH_3OH$ (saturated with $NH_3$) in $CH_2Cl_2$. FAB MS $[M+1]^+$ 529.1.

EXAMPLE 67

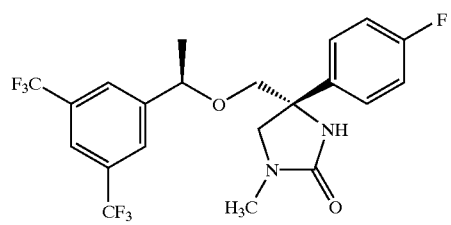

The title compound was prepared by methods analogous to Example 1, method 1, step 5, using the compound of Example 62 in place of 6. The title compound was obtained as a solid in a 51% yield. Electrospray MS $[M+1]^+$ 465.1.

EXAMPLE 68

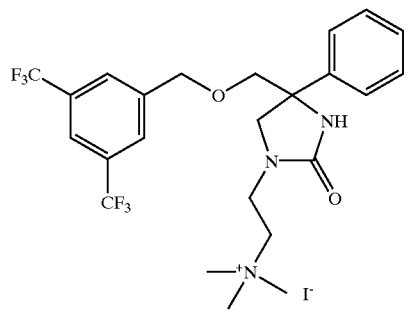

To a solution of compound of Example 67 (0.31 g, 0.64 mmol) in anhydrous THF (12.8 ml) at RT, $CH_3I$ (0.09 ml, 1.28 mmol) was added. The reaction mixture was stirred under $N_2$ for 5 h. Evaporation of the solvent gave a yellow foam, which was further purified by flash chromatography eluting with 7.5% $CH_3OH$ (saturated with $NH_3$) in $CH_2Cl_2$. Electrospray MS $[M+1]^+$ 504.

EXAMPLE 69

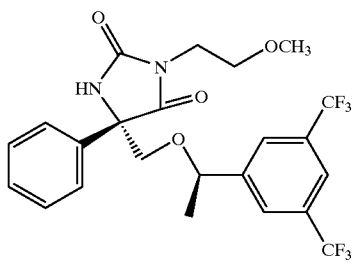

The title compound was prepared by a method analogous to Example 25, step 1, using 75 in place of 13 and 2-bromoethyl methyl ether in place of 4-(2- chloroethyl)morpholine hydrochloride salt. The title compound was obtained in a 61% yield. Electrospray MS [M+1]$^+$ 505.1.

EXAMPLE 70

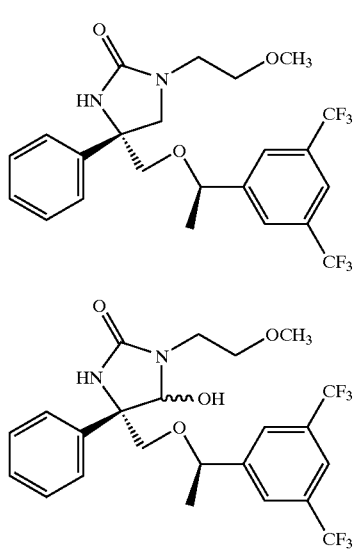

Reduction of the product of Example 69 with LAH—AlCl$_3$ complex at RT overnight, analogous to the method described in Example 26, gave the title compound 78 as a clear oil and compound 79 as a crystalline solid after separation of crude product using 3% CH$_3$OH(NH$_3$) in CH$_2$Cl$_2$. Electrospray MS: compound 78, MS [M+1]$^+$ 491.1 and compound 79, MS [M+1]$^+$ 507.4.

EXAMPLE 71

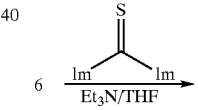

The title compound was prepared by analogous methods to that described in Examples 61, Step 7 and 62, using the phenyl analog in place of 74 in Example 62. The title compound was obtained as an oil. MS [M+1]$^+$ 407.1.

EXAMPLE 72

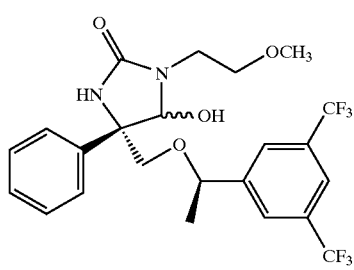

The title compound was prepared in a method analogous to Example 63, using Example 71 in place of the compound of Example 62. The title compound was obtained as an oil in 44% yield. NMR (CDCl$_3$) 1.45 (d, 3H), 2.38 (s, 3H), 3.87 (d, 1H), 3.27 (d,1H), 3.45 (d,1H), 3.55(d, 1H), 4.55 (q, 3H), and aromatic protons (7.3–7.4, 7.58, 7.78).

EXAMPLE 73

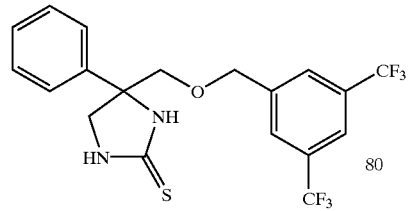

Step 1.

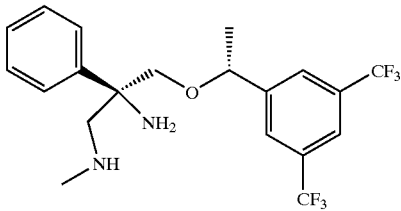

To a solution of compound 6 (1.85 g, 3.97 mmol) in dry THF (30 ml) was added Et$_3$N (0.6 ml, 4.3 mmol), 4 Å molecular sieve (3 g) and thiocarbonyl diimidazole (1.179 g, 5.95 mmol). The mixture was stirred at 0° C. under N$_2$ for 20 h. After completion, molecular sieve was filtered off and THF evaporated. The residue was redissolved in EtOAc (300 ml), washed with 0.04 N HCl (50 ml, 2×), dried (MgSO$_4$), filtered and evaporated. Pure 80 was obtained as a solid (1.41 g, 3.25 mmol) in 82% yield by flash silica chromatography (50 g), eluting with 5% (1:9) [NH$_4$OH/CH$_3$OH]/95% CH$_2$Cl$_2$.

Step 2.

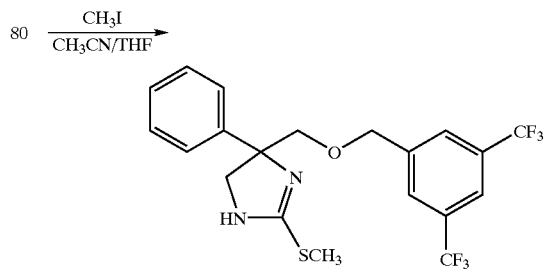

To a solution of 80 (0.75 g, 1.73 mmol) in CH₃CN and THF (6 ml) was added CH₃I (0.13 ml, 2.1 mmol). The solution was stirred at RT overnight under an atmosphere of N₂. After completion, solvent was evaporated and the product used in the next step without further purification. Step 3

81 (150 mg, 0.334 mmol) was treated with 2 M NH₃—CH₃OH solution (1 ml). The solution was stirred in a vial with a sealed cap for 5 days. After completion, solvent was evaporated and product was purified by flash silica gel (50 g), eluting with 5% (1:9) NH₄OH—CH₃OH/95% CH₂Cl₂. LCMS [M+1]⁺ 418.1.

EXAMPLE 74

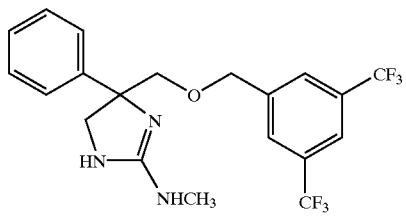

The title compound was prepared in a method analogous to Example 73, step 3, using 2M NH₂CH₃ in place of 2M NH₃. Product was purified on flash silica gel (50 g), eluting with 5% (1:9) NH₄OH—CH₃OH/95% CH₂Cl₂. LCMS [M+1]⁺ 432.1.

EXAMPLE 75

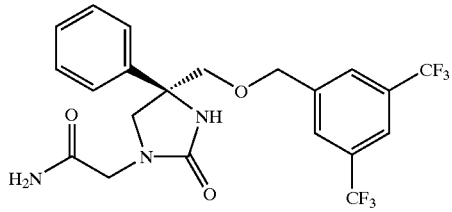

-continued

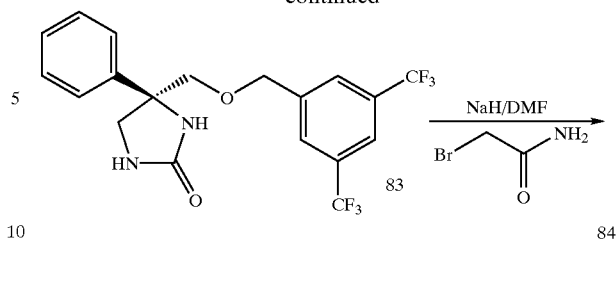

To a solution of 83 (0.4 g, 0.96 mmol) in anhydrous DMF (2 ml) was added 60% NaH (46.4 mg, 1.16 mmol) under N₂. After 20 min, 2-bromoacetamide (163.3 mg, 1.16 mmol) was added. The reaction was stopped by evaporating off the DMF after 20 h. The residue was redissolved in EtOAc (200 ml) and washed with brine (2×50 ml). The separated organic layer was dried over MgSO₄, filtered and concentrated in vacuo. Crude material was purified by flash silica chromatography, eluting with 4.5% (1:9) NH₄OH—CH₃OH in 96.5% CH₂Cl₂ to give the title compound 84 in a 25% yield. Electrospray MS [M+1]⁺ 476.1.

Example 76

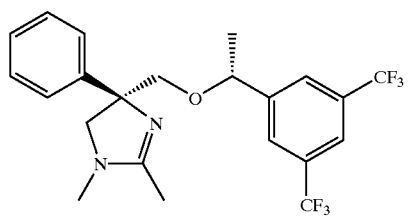

To a flask containing Example 71 (0.2 g, 0.48 mmol) and molecular sieves (0.18 g) in anhydrous toluene (4.5 ml), glacial acetic acid (0.3 ml, 5.24 mmol) was added. The reaction mixture was heated to 100° C. for 48 h. Cooled down to RT, the reaction was worked up by pouring into a separatory funnel containing EtOAc and saturated NaHCO₃. The aqueous layer was extracted with EtOAc (2×50 ml). The combined organic layer was washed with brine (50 ml), dried over Na₂SO₄, filtered and concentrated. The title compound 85 was obtained by purifying through flash chromatography, eluting with 20% EtOAc in hexane. Yield: 43%. Electrospray MS [M+1]⁺ 445.1.

EXAMPLE 77

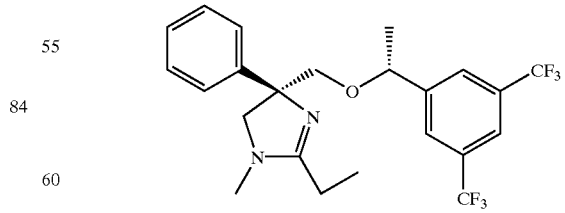

The title compound was prepared in a method analogous to Example 76, using propanoic acid in place of glacial acetic acid. The title compound was obtained in a 25% yield. Electrospray MS [M+1]⁺ 459.1.

EXAMPLE 78

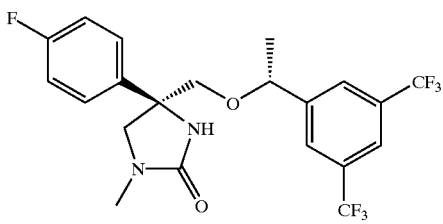

The title compound was prepared by a method analogous to Example 1, Method 1, Step 5, using Example 62 in place of 6. Purification by flash silica chromatography, using 5% (1:9)[NH$_4$OH/CH$_3$OH]/95% CH$_2$Cl$_2$ gave the title compound as a solid with a yield of 51%. LCMS [M+1]$^+$ 465.1.

EXAMPLE 79

Ex. 79a

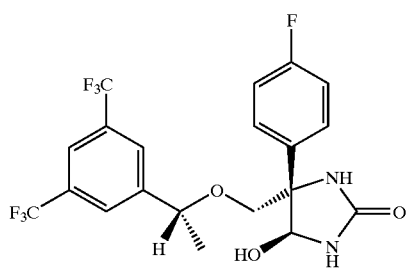

Ex. 79b

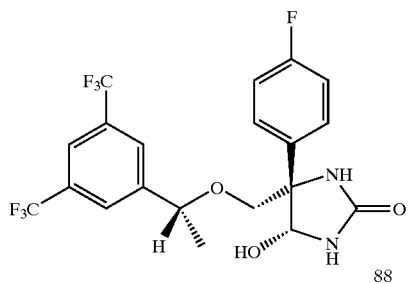

Step 1:

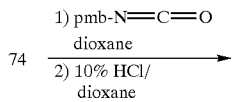

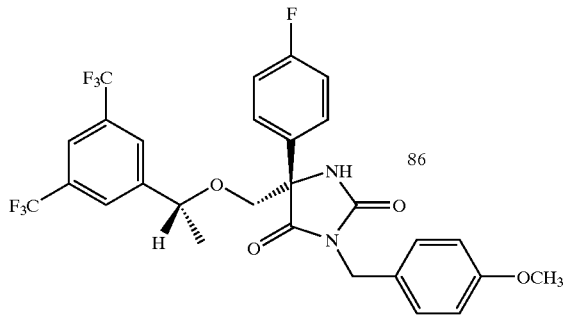

A solution of 74 (1.8 g, 4 mmol) in 1,4-dioxane (17 ml) and 4-methoxybenzyl-isocyanate (98 mg, 6 mmol) was stirred under N$_2$ at RT for 4 h. The mixture was mixed with 10% aqueous HCl in dioxane (17 ml), then heated to 90° C. for 5.5 h. After work-up, a solid was obtained as a crude product which was then purified by chromatography, eluting with 15% EtOAc/85% hexane to give 86 as a white solid (1.8 g, 82%). FAB MS [M+1] 584.

Step 2:

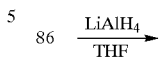

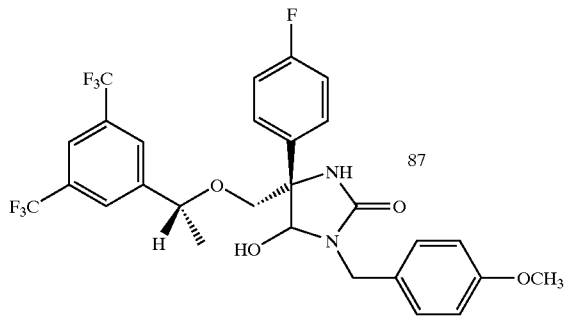

A mixture of 86 (1.7 g, 2.91 mmol) in THF (10 ml) and LiAlH$_4$ (1M in ether, 3.3 ml, 3.2 mmol ) was stirred under N$_2$ at 0° C. for 30 min., then RT for 3 h. After work-up, a solid was obtained as a crude product which was then purified by chromatography, eluting with 2% NH$_3$—CH$_3$OH (1:9)/98% CH$_2$Cl$_2$ to give 87 as a white solid (1.54 g, 91%). FAB MS [M+1] 587.4.

Step 3:

A mixture of 87 (1.48 g, 2.53 mmol) in CH$_3$CN (33 ml)/H$_2$O(10 ml) and Ce(NH$_4$)$_2$(NO$_3$)$_6$ (5.54 g, 10.1 mmol) was stirred under N$_2$ at RT for 50 min. After work-up, an oil was obtained as a crude product which was then purified by chiral HPLC (Chiralpak® AD), to give the title compounds, examples 79a and 79b, as a white solid (0.19 g, 16%). FAB MS [M+1] 467.1.

EXAMPLE 80

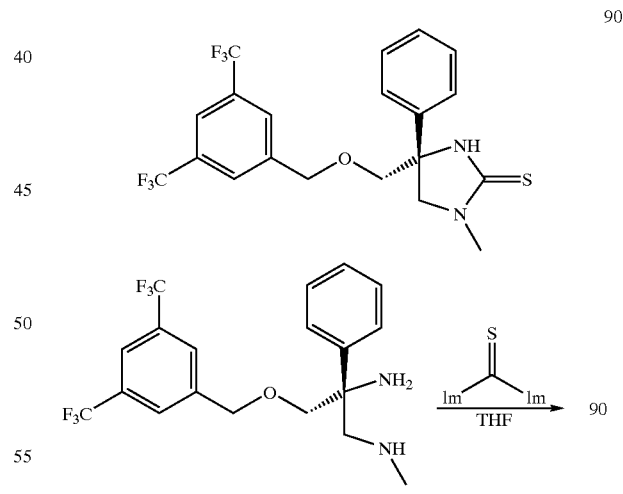

89 was prepared by a method analogous to Examples 61 and 62, using s-(+)-2-phenylglycine methyl ester hydrochloride in place of (s)—N-BOC-4-fluorophenylglycine in Example 61. A mixture of 89 (2.03 g, 5 mmol) in THF (6 ml) and 1,1-thiocarbonyldiimidazole (1.34 g, 7.5 mmol) was stirred under N$_2$ at RT for 18 h. After work-up, a yellow paste was obtained as a crude product which was then purified by chromatography, eluting with 25% EtOAc/75%

Example 81

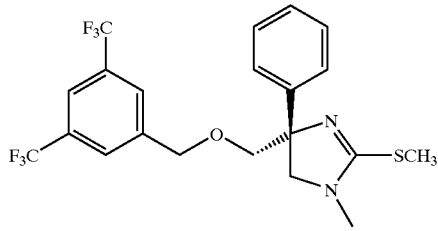

A solution of the product of Example 80 (1.2 g, 2.68 mmol) in THF (10 ml) and CH₃I (0.45 g, 3.2 mmol) was stirred under N₂ at RT for 5 h. After work-up, a solid was obtained as a crude product which was then purified by trituration with ether to give the title compound as a pale yellow salt (1. 5 g, 94%). FAB MS [M+1] 463.1.

EXAMPLE 82

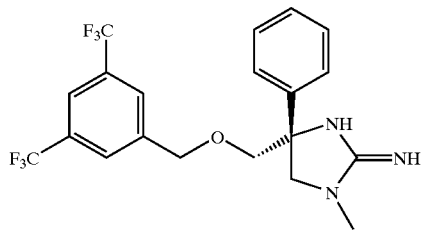

A solution of the product of Example 81 (0.3 g, 0.51 mmol) and 7 N NH₃ (2 ml, 14 mmol) in CH₃OH was stirred under N₂ at RT for 4 days. After work-up, a solid was obtained as a crude product which was then purified by chromatography, eluting with 9% NH₃—CH₃OH (1:9)/91% CH₂Cl₂ to give the title compound as a solid (0.19 g, 86%). FAB MS [M+1] 432.1.

EXAMPLE 83

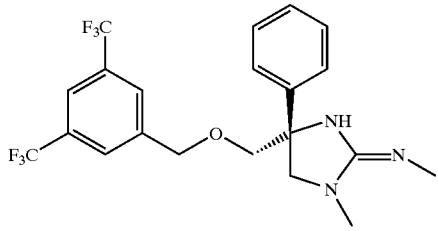

The title compound was prepared by a method analogous to Example 82, using 2 M CH₃NH₂ in CH₃OH in place of 7 M NH₃ in CH₃OH. The title compound was obtained as a solid in a 95% yield. FAB MS [M+1] 446.1.

EXAMPLE 84

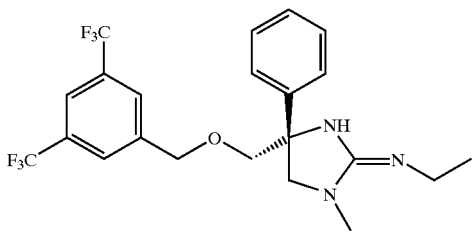

The title compound was prepared by a method analogous to Example 82, using 2 M ethylamine in CH₃OH in place of 7 M NH₃ in CH₃OH. The title compound was obtained as a solid in a 17% yield. FAB MS [M+1] 460.1.

EXAMPLE 85

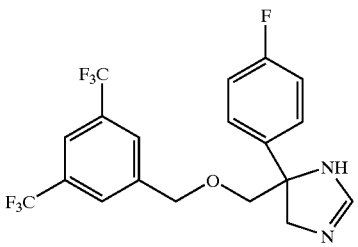

A mixture of 22 (0.3 g, 0.73 mmol) and N,N-dimethylformamide dimethyl acetal (87 mg, 0.73 mmol) was heated to 60° C. for 18 h. The reaction mixture was purified by chromatography, eluting with 3.5% NH₃—CH₃OH (1:9)/96.5% CH₂Cl₂ to give the title compound as an off-white solid (180 mg, 60%). FAB MS [M+1] 421.1.

EXAMPLE 86

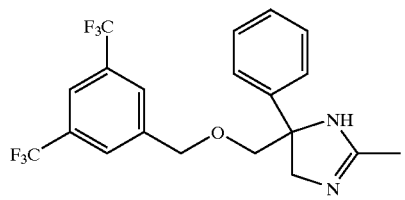

A mixture of 6 (0.4 g, 1 mmol) in toluene (3 ml) and acetic acid (0.24 g, 4 mmol) was heated to reflux for 6 days. After work-up, an oil was obtained as a crude product which was purified by chromatography, eluting with 5% NH₃—CH₃OH (1:9)/95% CH₂Cl₂ to give the title compound as a HCl salt (75 mg, 18%) after treating the pure compound with 1 eq. of 2 N HCl-Et₂O solution. FAB MS [M+1] 417.1.

EXAMPLE 87

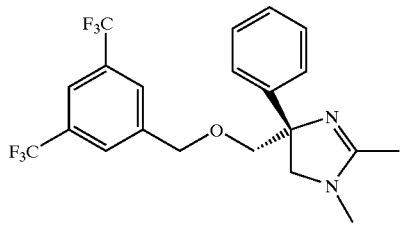

A mixture of 89 (0.4 g, 0.985 mmol) in toluene (3 ml) and acetic acid (0.59 g, 9.85 mmol) was heated to 100° C. for 40 h. After work-up, an oil was obtained as a crude product which was purified by chromatography, eluting with 3.5% $NH_3$—$CH_3OH$ (1:9)/96.5% $CH_2Cl_2$ to give the title compound as a HCl salt (0.32 g, 76%) after treating the pure compound with 1 eq. of 2 N HCl—$Et_2O$ solution. FAB MS [M+1] 431.1.

EXAMPLE 88

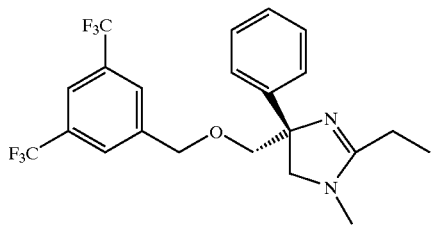

The title compound was prepared by a method analogous to Example 87, using propionic acid in place of acetic acid. The title compound was obtained as a HCl salt in a 59% yield. FAB MS [M+1] 445.1.

EXAMPLE 89

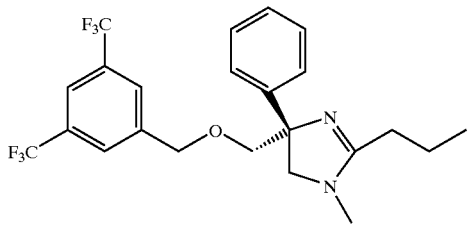

The title compound was prepared by a method analogous to Example 87, using n-butyric acid in place of acetic acid. The title compound was obtained as a HCl salt in a 88% yield. FAB MS [M+1] 459.1.

EXAMPLE 90

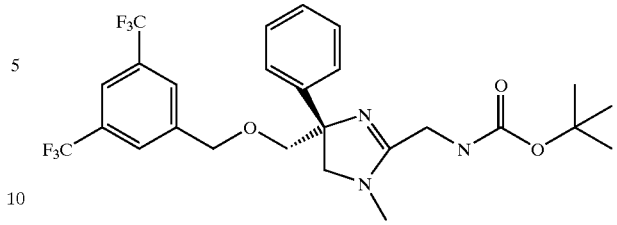

The title compound was prepared by a method analogous to Example 87, using N-t-BOC glycine in place of acetic acid. The title compound was obtained as a HCl salt in a 63% yield. FAB MS [M+1] 546.1.

EXAMPLE 91

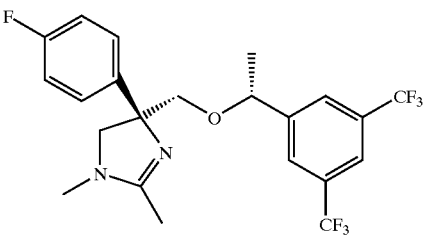

The title compound was prepared by a method analogous to Example 76 using Example 62 in place of Example 71. Purification the crude material by flash silica chromatography, using 5% (1:9)[$NH_4OH/CH_3OH$]/95% $CH_2Cl_2$ gave the title compound as a solid with a yield of 75%. LCMS [M+1] 463.1.

EXAMPLE 92

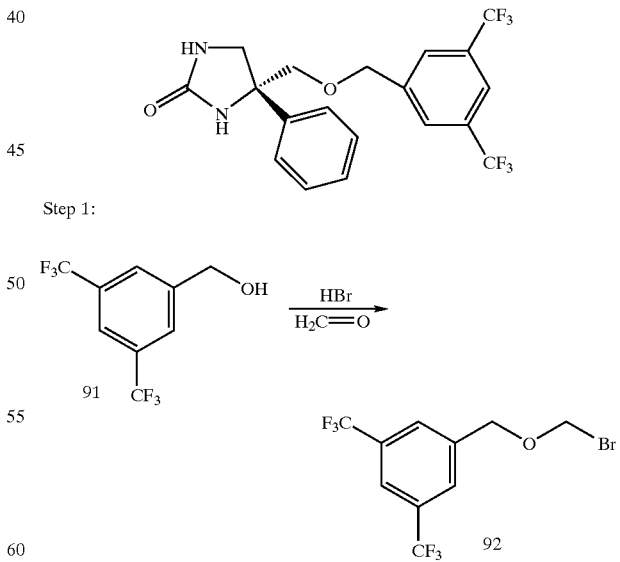

Step 1:

A flame-dried flask was charged with compound 91 (50 g, 204.8 mmol, 1 equiv.) and paraformaldehyde (6.76 g, 225.3 mmol, 1.1 equiv.). The solid mixture was dissolved under $N_2$ with a heat gun until the solution was homogeneous, approximately 20 min. The solution was allowed to cool to RT. HBr gas was bubbled into the solution at a fast rate at RT. The reaction was continued for 2.5 h. The layers were separated, the upper layer was diluted with hexane (150 ml) and any aqueous remnants were removed. The hexane layer was dried over MgSO$_4$ overnight, then filtered and concentrated. Short path distillation (high vac, 75° C.)gave pure 92 (67.86 g, 98%) as a clear oil. $^1$H NMR (CDCl$_3$)δ 4.85 (s, 2H), 5.79 (s, 2H), 7.84 (s, 2H), 7.87 (s, 1H).

Step 2:

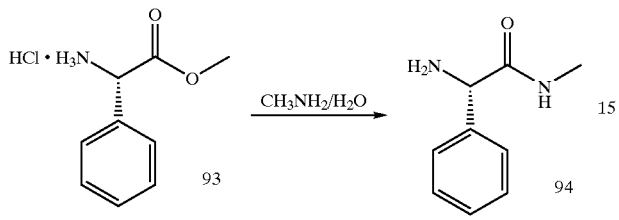

Compound 93 (100 g, 496 mmol, 1 equiv.) was added to CH$_3$NH$_2$ (160 ml, 40% in H$_2$O, 4 equiv.) in a cool water bath at 10–16° C. over a period of 15 min. After complete addition, the solution was warmed to RT and stirred for 1 h. The reaction was monitored by TLC in 98:2 EtOAc/CH$_3$OH. Upon completion, the reaction was quenched with brine (25% in H$_2$O, 500 ml). The solution was extracted with 1:1 THF/EtOAc (4×400 ml) and the combined organic phases were dried (Na$_2$SO$_4$) and concentrated. The residue was dried on high vacuum to give 94 (79.47 g, 98%). Electrospray MS [M+1]$^+$ 165.0.

Step 3:

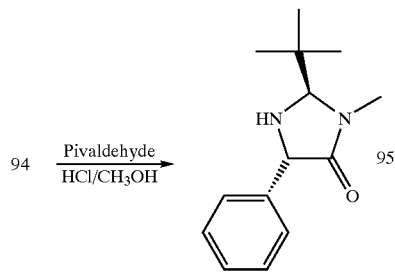

A mixture of 94 (79.44 g, 483.8 mmol, 1 equiv.), pentane (550 ml), and trimethylacetaldehyde (65.7 ml, 604.8 mmol, 1.25 equiv.) was heated to 65° C. in a system equipped with a condenser, Dean-Stark trap and N$_2$ inlet. The mixture was heated for 3 h and the suspension dissolved. The solution was cooled to RT and stirred overnight (16 h). The solution was concentrated, redissolved in CH$_3$OH (140–150 ml), cooled in an ice bath for 30 min, and then saturated HCl—CH$_3$OH (300 ml) was slowly added via a dropping funnel over 30 min. The solution was stirred at 0° C., then warmed to RT under N$_2$ overnight and concentrated on high vac to yield a crude, yellow oil (109.1 g). The oil was redissolved in CH$_2$Cl$_2$ (800 ml) and washed. with 25% K$_2$CO$_3$ (w/w, 400 ml). The aqueous portion was washed again with CH$_2$Cl$_2$ (2×400 ml). The combined organics were dried (Na$_2$SO$_4$) and concentrated to give a yellow solid (98.7 g). The crude solid was recrystallized out of hot MTBE (300 ml), then cooled to 0° C. to give 95 as a white solid (54.88 g, 49%). Mother liquor still contained product which could be isolated by another recrystallization or by chromatography. Electrospray MS [M+1]$^+$ 451.1

Step 4:

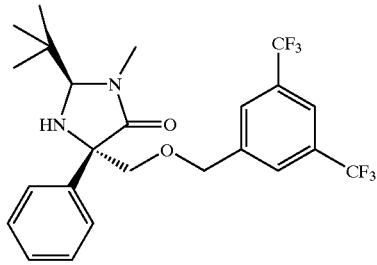

All reagents were deoxygenated under Ar prior to use. 95 (42.05 g, 181 mmol, 1 equiv.) was dissolved in dry THF from a still (550 ml) while agitating with a mechanical stirrer. The solution was cooled to approximately −70° C. in dry ice/acetone and a solution of 1.5 M LDA·THF in cyclohexane (124.3 ml, 186.5 mmol, 1.03 equiv.) was added over 20 min. The resultant dark orange/brown solution was allowed to stir at −78° C. for 30 min. Bromide 92 (64.0 g, 190 mmol, 1.05 equiv.) was slowly added via syringe over 20 min. The solution was stirred at −78° C. and monitored by TLC in 4:1Hex/EtOAc. The reaction was complete after 2 h. The reaction was quenched with sat. aq. NH$_4$Cl (300 ml) at −78° C. and then warmed to RT while stirring vigorously. Phases were separated and the organic phase washed with H$_2$O (2×150 ml). The aqueous layer was washed with EtOAc (300 ml). The combined organics were dried (Na$_2$SO$_4$) and concentrated to give a crude, light yellow solid (32.63 g), which was recrystallized out of hot pentane to give 96 (33.66 g). The mother liquor was again concentrated to an orange solid and recrystallized out of pentane (150 ml) to give an additional 10.50 g of product (Overall yield=44.16 g, 50%). The mother liquor (46.7 g, approximately 50% pure by NMR) still contained starting product which could be isolated. Electrospray MS [M+1]$^+$ 489.1

Step 5:

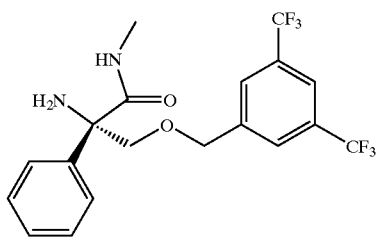

To a solution of 96 (33.58 g, 68.76 mmol, 1 equiv.) in CH$_3$OH (300 ml), concentrated HCl (300 ml) was added dropwise with stirring. The solution was heated to 95° C. and stirred vigorously, and was stirred and heated overnight. The reaction was monitored by TLC. Upon completion, solvent was evaporated and the residue was taken up in CH$_2$Cl$_2$ (750 ml). The solution was treated with 25% aq. K$_2$CO$_3$ (approximately 350 ml) until pH 12. The mixture was filtered and the layers separated. The organic layer was washed with 25% aq. K$_2$CO$_3$ (500 ml). Combined aqueous layers were extracted with CH$_2$Cl$_2$ (2×750 ml). Combined organic layers were dried (Na$_2$SO$_4$), and concentrated to a yellow oil. $^1$H NMR shows pure 97 (29.20 g, 100%). $^1$H NMR (CDCl$_3$) δ 2.04 (s, 2H), 2.80 (d, J=4.8 Hz, 3H), 3.67 (d, J=8.8 Hz, 1H), 4.53 (d, J=8.8 Hz, 1H), 4.67 (d, J=12.5

Hz, 1H), 4.77 (d, J=12.5 Hz, 1H), 7.26–7.36 (m, 3H), 7.51 (d, J=8.1 Hz, 2H), 7.65 (d, J=4.4 Hz, 1H), 7.75 (s, 2H), 7.79 (s, 1H).

Step 6:

The title compound was prepared from 97 using procedures similar to Example 61, steps 6 and 7.

EXAMPLE 93

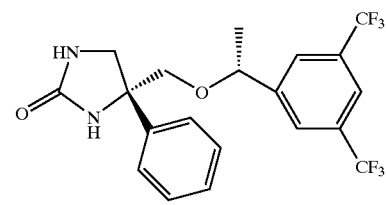

Step 1:

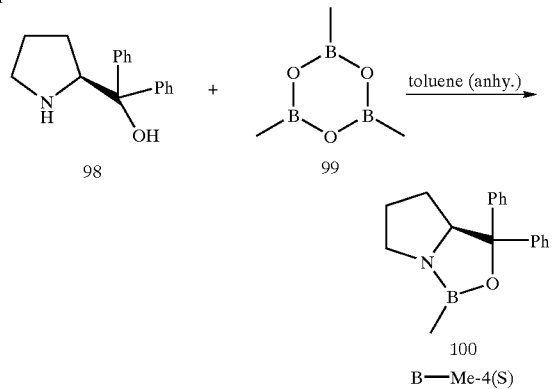

A flame-dried flask was charged with 98 (5.10 g, 20.1 mmol, 1.0 eq) and anhydrous toluene (56 ml). This cloudy solution was heated up to 140~150° C. 36 ml of dry toluene was azeotropically distilled through a Dean-Stark trap with an air condenser. Another 36 ml of toluene was added. This azeotropical distillation was repeated three times to ensure 98 was totally dry. After the third azotropical distillation was done, another 36 ml of anhydrous toluene was added. The solution was allowed to cool down to RT. 99 (1.90 ml, 13.5 mmol, 0.67 eq) was syringed in within 5 min. White solid was formed at about 6 min after completion of the addition. The reaction mixture was stirred at RT for 30 min, then 36 ml of toluene was distilled off. Another 36 ml of dry toluene was added and distilled off again. The distillation was repeated one more time, and 20 ml of 1.0 M of 100 (CBS catalyst B-Me-4(S)solution in toluene) was prepared. The almost colorless solution can be used in CBS reduction directly.

Step 2:

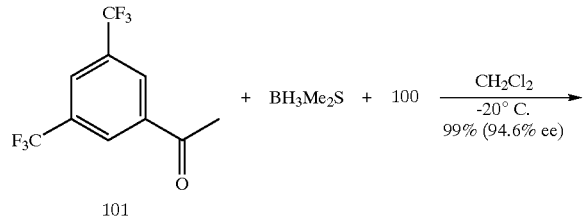

-continued

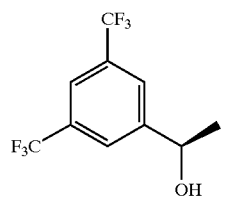

101 (102.14 g, 0.4 mol, 1.0 eq) was dissolved in anhydrous CH$_2$Cl$_2$ (780 ml) and the resulting solution was transferred into a dry dropping funnel. An oven-dried 3L flask was cooled to −20° C., and 20 ml of 102 toluene solution was syringed in, followed by 40 ml of 10.0~10.3 M borane-methylsulfide complex. Then the 101 solution was added dropwise through the dropping funnel over 2 days. During the addition, the temperature was maintained at −20° C. Once the addition was finished, the reaction was monitored by TLC in 4:1 hexane/EtOAc. When 101 was completely consumed, 250 ml of CH$_3$OH was added slowly. and hydrogen gas was emitted. The reaction solution was then concentrated to give white solid. The solid was dissolved in Et$_2$O (500 ml), then 45 ml of 2.0 M of HCl in Et$_2$O was added slowly at −20° C. White precipitate was formed. The reaction mixture was warmed to RT and stirred for 30~40 min. The mixture was filtered and the filtrate concentrated to give 101.5 g of white solid 102 (yield 98.7%). Chiral HPLC Chiral OD(Chiralcel) column (Hexane/IPA=98/2) showed 94.6% ee.

Step 3:

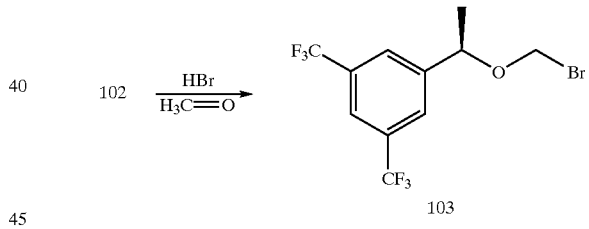

103 was prepared in a method analogous to Example 92, Step 1 using 102 in place of 91.

Step 4:

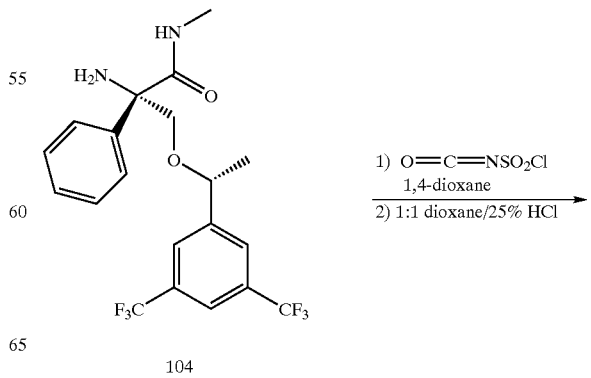

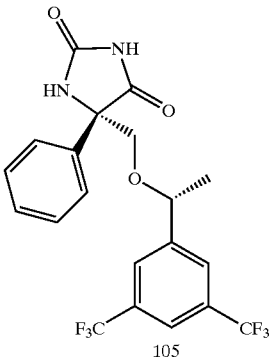

105

Amino amide 104 (14.14 g, 32.55 mmol, 1 equiv.) (prepared in a similar procedure to that described in Example 92, substituting 103 in place of 92 in step 4) was taken up in dry CH$_2$Cl$_2$ (120 ml). The solution was cooled to −78° C. and chlorosulfonyl isocyanate (2.84 ml, 32.55 mmol, 1 equiv.) was added. The reaction was stirred at 0° C. for 3 h and then concentrated to a white solid. The solid was dissolved in 1,4-dioxane (120 ml) and 3 N aqueous HCl (120 ml), then stirred at 90° C. for 5 h, then at RT overnight. The solution was diluted with H$_2$O (250 ml) and extracted with EtOAc (3×400 ml). The combined organics were dried (Na$_2$SO$_4$), and concentrated to a crude, white foam (15.80 g). the foam was purified by plug chromatography on a 600 ml fritted funnel, eluting with 2:1Hex/EtOAc. The fractions 2–8 were collected and concentrated to give pure 105 (10.26 g, 71%). FAB MS [M+1]$^+$ 447.1

Step 5:

AlCl$_3$ (12.2 g, 91.4 mmol, 4 equiv.) was added to a flask equipped with a N$_2$ inlet. The flask was cooled to 0° C. and a solution of 1 M LAH in ether (68.6 ml, 68.6 mmol, 3 equiv.) was slowly added. The resultant white slurry was stirred at 0° C. for 15 min. Next, a solution of hydantoin 105 (10.2 g, 22.85 mmol, 1 equiv.) in 150 ml dry THF was added via canula. The solution was warmed to RT and stirred for 41 h. The solution was again cooled to 0° C. and H$_2$O (20 ml) was added, then 15% aq. NaOH (w/w, 20 ml) followed by H$_2$O (60 ml). The biphasic solution was stirred for 30 min. All emulsion formed was dissolved with 1 N HCl (approximately 300–400 ml) and the layers were separated. The aqueous layer was extracted with EtOAc (2×500 ml). The combined organics were washed with H$_2$O (200 ml), dried (Na$_2$SO$_4$), and concentrated to give the crude (9.86 g). The crude material was initially purified by plug chromatography on a 2L fritted funnel, eluting with 1:1 Hex/EtOAc, followed by 98:2 EtOAc to give 8.0 g of material, which still contained 3% of a less polar impurity. The solid was recrystallized from hot MTBE (30 ml) to provide pure Example 93 (6.5 g, 79%). FAB MS [M+1]$^+$ 433.1

EXAMPLE 94

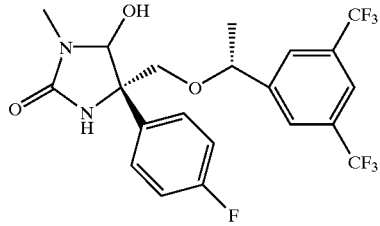

Step 1:

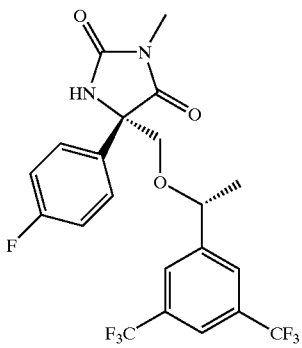

106

104 (3.0 g, 6.63 mmol, 1 equiv.) (prepared analogously to the procedure described in a Example 92) was dissolved in CH$_2$Cl$_2$ (100 ml) and cooled to 0° C. Et$_3$N (2.78 ml, 19.89 mmol, 3 equiv.) followed by triphosgene (787 mg, 2.65 mmol, 0.4 equiv.) was added and the solution was allowed to stir and warm to RT. Reaction as complete after 2 h as determined by TLC. The reaction was quenched with sat. aq. NaHCO$_3$ (100 ml) and the layers were separated. The organic layer was washed with brine (100 ml), dried (Na$_2$SO$_4$), and concentrated. The crude product was purified by Biotage chromatography, eluting with CH$_2$Cl$_2$ to give 2.024 g (64%) of 106. FAB MS [M+1]$^+$ 479.1.

Step 2:

106 (919 mg, 1.92 mmol, 1 equiv.) was dissolved in dry THF (10 ml) and cooled to 0° C. A 1 M solution of LAH in Et$_2$O (1.92 ml, 1.92 mmol, 1 equiv.) was slowly added and the solution was stirred at 0° C. for 10 min. The reaction was warmed to RT and completed after 2 h. The solution was cooled to 0° C. and water (3 ml) was slowly added, followed by 15% aq. NaOH (3 ml), and then more water (10 ml). The emulsion was dissolved with 1 M HCl and the layers were separated. The aqueous layer was extracted with EtOAc (2×100 ml) and the organic layers were combined, washed with water (50 ml), dried (Na$_2$SO$_4$), and concentrated to give crude product (914 mg). Biotage chromatography, eluting with 98:2 CH$_2$Cl$_2$/CH$_3$OH(NH$_3$) gave a 3:2 mixture of diastereomers (798 mg) (87%). Prep HPLC on 50 mg of product using a chiralcel OD column, eluting with 85:15Hex/IPA gave the title compound (t$_R$=6.4 min), a white powder (12.7 mg, 51%, 98% de). HRMS [M+1]$^+$ 481.1362.

EXAMPLE 95

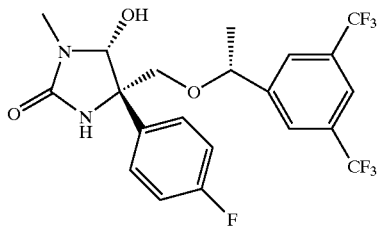

The title compound was prepared from 106 using the procedure of Example 94. Prep HPLC on 50 mg of material on chiralcel OD column, eluting with 85:15 Hex/IPA gave the title compound ($t_R$=8.2 min) as a clear oil (17.5 mg, 70%, 78% de). HRMS [M+1]$^+$ 481.1362

EXAMPLE 96

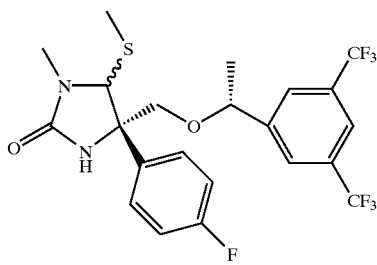

A 2:3 diastereomeric mixture of Examples 94 and 95 (100 mg, 0.208 mmol, 1 equiv.) was dissolved in $CH_2Cl_2$ (2 ml) and treated with $NaSCH_3$ (29.2 mg, 0.416 mmol, 2 equiv.). The suspension was treated with concentrated HCl (4–5 drops) and stirred at RT. The reaction was complete after 30 min as determined by TLC. The reaction mixture was diluted with $CH_2Cl_2$ (40 ml), washed with sat. aq. $NaHCO_3$ (30 ml) and brine (30 ml), dried ($Na_2SO_4$), and concentrated. The crude product was purified by Biotage chromatography, eluting with 1:1Hex/EtOAc to give the title purified by chromatography, eluting with 3.5% $NH_3$—$CH_3OH$ (1:9)/ 96.5% $CH_2Cl_2$ to [M+1]$^+$ 511.1

EXAMPLE 97

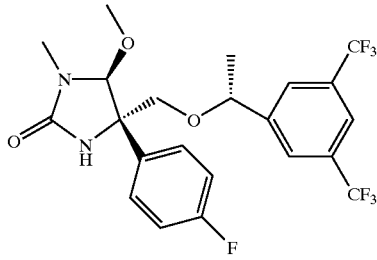

A 2:3 diastereomeric mixture of Examples 94 and 95 (100 mg, 0.208 mmol, 1 equiv.) was dissolved in $CH_3OH$ (3 ml), cooled to 0° C., and treated with concentrated HCl in $CH_3OH$ (14 drops). This was warmed to RT and stirred to completion (24h). The reaction mixture was diluted with $CH_2Cl_2$ (100 ml), washed with sat. aq. $NAHCO_3$ (30 ) and then brine (30 ml), dried ($Na_2SO_4$), and concentrated. the crude mixture was purified by Biotage chromatography, eluting with 3:2 EtOAc/Hex (2% $NEt_3$) to give a product as a 3:2 mixture of diastereomers. Isolation by prep HPLC on an chiralcel OD column, eluting with 95:5Hex/IPA gave the title compound ($t_R$=6.7 min) (29 mg, 28%). HRMS[M+1]$^+$ 495.1419

EXAMPLE 98

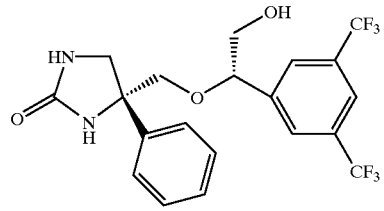

Step1:

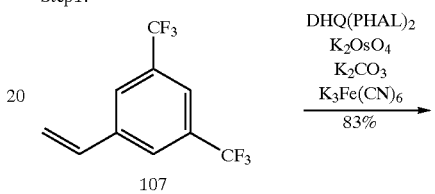

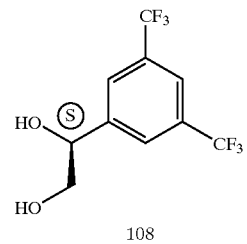

A solution of $K_2CO_3$ (31.0 g, 187.5 mmol, 3 equiv.), $K_3Fe(CN)_6$ (61.75 g, 187.5 mmol, 3 equiv.), (DHQ)$_2$PHAL (2.44 g, 3.13 mmol, 0.05 equiv.), and $K_2OsO_4.2H_2O$ (1.16 g, 3.13 mmol, 0.05 equiv.) in $^tBuOH/H_2O$ 1:1 (750 ml) was stirred and cooled to 0° C. The suspension was treated with 107 (11.25 ml, 62.5 mmol, 1 equiv.) and stirred at 0° C. for 3.5 h. The reaction mixture was treated with $Na_2SO_3$ (95 g, 750 mmol, 12 equiv.) and warmed to RT. The biphasic solution was separated and the aqueous layer was extracted with EtOAc (500 ml). Combined organic fractions were washed with brine (200 ml), dried ($Na_2SO_4$), and concentrated to a yellow solid. The crude product was recrystallized from minimum 1,2-dichloroethane to give 108 (14.12 g, 83%) as a white solid. $^1H$ NMR (CD$_3$OD)δ 3.67 (d, J=5.6 Hz, 2H), 4.85 (t, J=5.6 Hz, 1H), 7.85 (s, 1H), 7.99 (s, 2H).

Step 2:

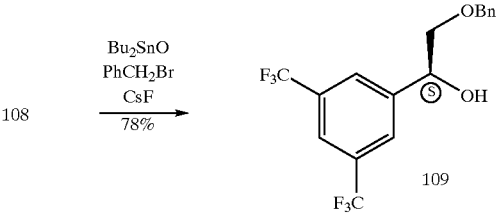

A mixture of 108 (4.0 g, 14.6 mmol, 1 equiv.) and dibutyltin oxide (3.64 g, 14.6 mmol, 1 equiv.) in toluene (60 ml) was refluxed for 2 h under a Dean Stark trap. The solution was concentrated to obtain a white solid. To this solid, CsF (4.30 g, 28.32 mmol, 1.94 equiv.) was added and the mixture was dried in vacuo overnight. Benzyl bromide (3.0 ml, 25.11 mmol, 1.72 equiv.) in dry DMF (60 ml) was added and the reaction mixture was stirred vigorously for 6 h. The solution was concentrated, taken up in EtOAc (200 ml) and the solid filtered off. The organics were extracted with water (4×100 ml), dried (Na$_2$SO$_4$), and concentrated. The crude product was purified by Biotage chromatography eluting with 9:1Hex/EtOAc→4:1Hex/EtOAc to give 109 (4.15 g, 78%) as a pale yellow oil. FAB MS [M+1]$^+$ 363.0.

Step 3:

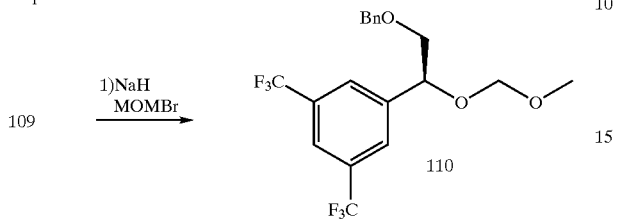

NaH (834 mg, 20.85 mmol, 1.1 equiv.) was added to a stirred solution of 109 (6.90 g, 18.95 mmol, 1 equiv.) in THF (20 ml) under N$_2$. The mixture was stirred for 1 h, then cooled to 0° C. MOMBr (2.63 g, 21.06 mmol, 1 equiv.) was added dropwise. The solution was warmed to RT and stirred for 1 h. The white mixture was filtered through a plug of celite and the filtrate was concentrated to give 110 (7.90 g, >95%) as a pure, yellow oil. $^1$H NMR (CDCl$_3$)δ 3.36 (s, 3H), 4.55 (s, 2H), 4.61 (d, 7.0Hz, 1H), 4.75 (d, 6.6 Hz, 1H), 4.92 (t, J=4.8 Hz, 1H), 7.21–7.31 (m, 5H), 7.82 (s, 1H), 7.83 (s, 2H).

Step 4:

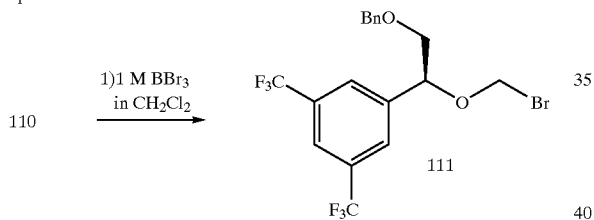

To an ice-cooled solution of 110 (5.85 g, 14.33 mmol, 3 equiv.) in CH$_2$Cl$_2$ (15 ml) was added a solution of 1 M BBr$_3$ in CH$_2$Cl$_2$ (1.64 ml, 1.64 mmol, 1 equiv.). The solution was warmed to RT and stirred for 4 h. The reaction mixture was concentrated to a crude brown oil 111 (6.1 g, 93%) which was used in the next step.

Step 5:
The title compound was prepared by a method analogous to Example 92 using 111 in place of 92 for step 4.

EXAMPLE 99

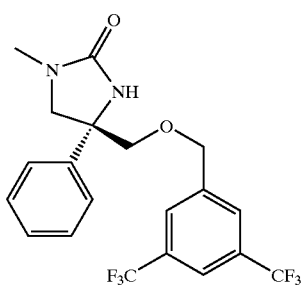

The product of example 92 (0.25 g, 0.59 mmol, 1.0 equiv.) was taken up in 4 ml dry DMF and cooled to 0° C. in a ice bath. NaH (60% dispersion in mineral oil) (0.0179 g, 0.59 mmol, 1.0 equiv.) was added to the reaction mixture, the solution was warmed to RT and stirred for 45 min. CH$_3$I (0.053 ml, 0.66 mmol, 1.1 equiv.) was added and reaction mixture was stirred at RT over night. The reaction was monitored by TLC in 4/1 EtOAc/Hexane. The reaction did not go to completion, hence was quenched with H$_2$O (3×15 ml). The mixture was extracted with EtOAc (2×15 ml) dried (Na$_2$SO$_4$), concentrated and dried on high vacuum. Purification using Biotage chromatography with 60/40 Hexane/EtOAc gave the title compound (0.127 g, 50%). MS [M+1]$^+$ 433.1.

EXAMPLE 100

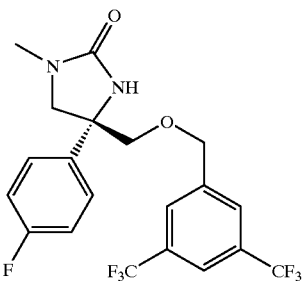

The title compound was prepared using a procedure similar to Example 99 using the product of Example 2B in place of Example 92. MS [M+1]$^+$ 451.1.

EXAMPLE 101

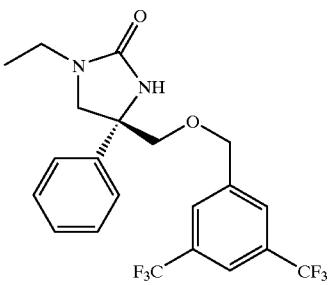

The title compound was prepared using a procedure similar to Example 99 using ethyl iodide in place of CH$_3$I to give the title compound. MS [M+1]$^+$ of crude 447.1.

EXAMPLE 102

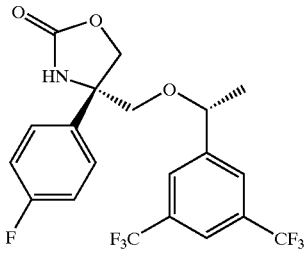

87

Step 1:

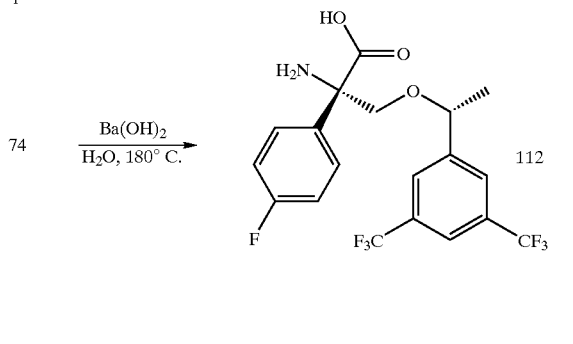

74 (6.0 g, 13.7 mmol, 1.0 eqv), Ba(OH)₂ (20.8 g, 65.9 mmol, 4.8 equiv.) a H₂O(50 ml) were combined in a high pressure bomb equipped with a stirring bar. It was heated at 165° C. for 64 h, and then the temperature was increased to 180° C. The bomb was heated for another 3 days, then cooled, and the crude product was treated with CH₃OH (NH₃) to transfer the hardened crude to solution. The mass gradually dissolved using 10 (40–50 ml) portions with sonication each time. The resulting turbid solution was filtered and concentrated. The crude was then dissolved in ether, filtered and concentrated to give pale yellow solid 112 (6.2 g, >95%).

Step 2:

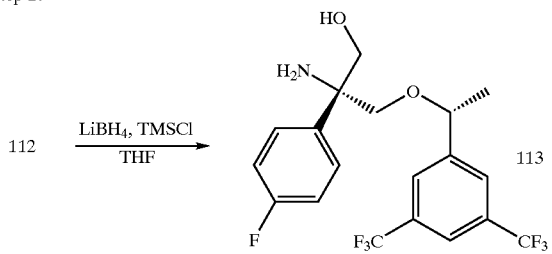

A solution of LiBH₄ (0.01 g, 0.46 mmol, 2.0 eqiv) was treated with TMSCl (0.115 ml, 0.91 mmol, 4.0 eqiv). After 5 min, 112 (0.1 g, 0.227 mmol, 1.0 equiv.) was added as a powder and the mixture was stirred for 18 h. It was monitored by TLC 70:10:20 (EtOAc: Et₃N:CH₃OH). Upon completion, the reaction was quenched with 5 ml CH₃OH and stirred for another 1 h. Purification by Biotage in 97:3 CH₂Cl₂/CH₃OH (NH₃) gave the product 113 (0.65 g, 67%).

Step 3:

A solution of 113 (0.63 g, 0.148 mmol, 1.0 equiv) in dry CH₂Cl₂ (4 ml) was treated with diisopropyl ethyl amine (0.077 ml, 0.444 mmol, 3.0 equiv.) followed by triphosgene (0.0176 g, 0.059 mmol, 0.4 equiv.). The reaction mixture was stirred at RT for 10 min. Monitoring by TLC 2/1 Hexane/EtOAc showed reaction completion. The crude product was purified using Biotage chromatography, eluting with 98/2 CH₂Cl₂/CH₃OH to give the title compound as a white foam (0.58 g, 86%). MS [M+1]⁺ 452.

88

EXAMPLE 103

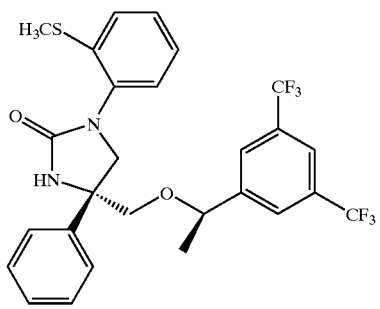

Step 1

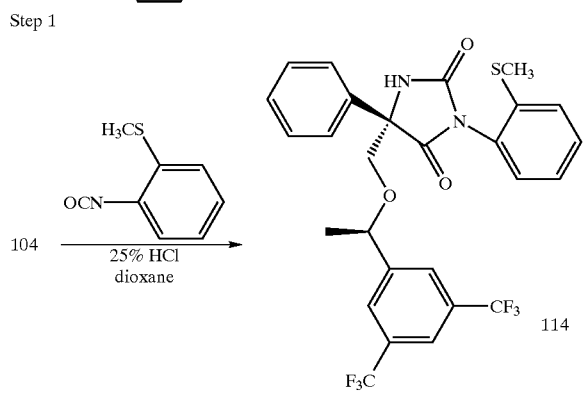

To a solution of 104 (0.225 g, 0.518 mmol) in CH₂Cl₂ (3 ml) was added 2-methylthiophenylisocynate and the resulting solution was stirred for 12 h. The solvent was removed and the residue treated with dioxane/25% HCl (4 ml, 2:1, v/v) and heated at 90° C. overnight. After cooling to RT, the solution was diluted with EtOAc and water and the layers separated. The aqueous layer was extracted with EtOAc three times. The combined organic layers were washed with half saturated NaHCO₃ solution and brine, dried over MgSO₄, filtered and concentrated. Flash chromatography afforded 114 (0.265 g, 95%). Electrospray MS [M+1]⁺ 569.1

Step 2:

To solid AlCl₃ (346.7 mg, 2.6 mmol) at 0° C. under N₂ was added LiAlH₄ (2.03 ml, 1M in Et₂O, 2.03 mmol). The resulting suspension was stirred for 10 min, then a solution of 114 (320 mg ) in THF (19 ml) was cannulated into the hydride suspension dropwise. After 5 min, the solution was allowed to warm to 23° C. and stirred for 2 h. The reaction mixture was cooled to 0° C., quenched with 10 ml saturated sodium potassium tartrate, stirred at 23° C. for 2 h, then patitioned between water and EtOAc. The organic layer was washed with brine, dried over MgSO₄, filtered and concentrated.

Step 3

A solution of the crude hydroxyurea from Step 2 in CH₂Cl₂ (3 ml) was treated with triethylsilane (1.5 ml) followed by addition of TFA (0.178 ml), stirred overnight, further treated with TFA (0.098 ml) and stirred for 4 h. The mixture was concentrated, then re-dissolved in CH₂Cl₂ and stirred with solid K₂CO₃ for 2 h. The solution was filtered and concentrated. Flash chromatography afforded the title urea. Electrospray MS [M+1]⁺ 555.1.

EXAMPLES 104–111

The following examples were prepared in a similar fashion to Example 103 using the appropriate isocycanate:

EXAMPLES 112–113

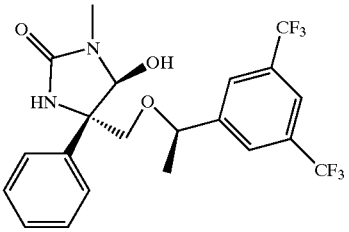
Ex. 112

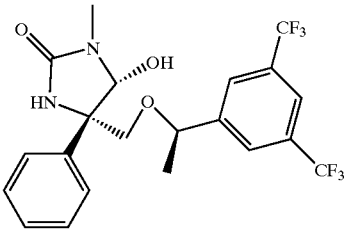
Ex. 113

Step 1:

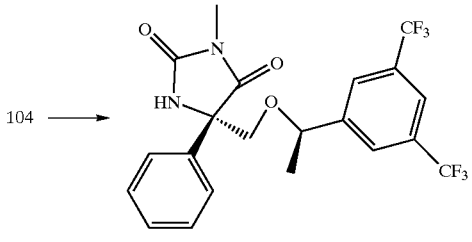

104 (1.26 g, 2.9 mmol) was dissolved in $CH_2Cl_2$ (58 ml) at 0° C., followed by addition of $Et_3N$ (1.2 ml, 8.7 mmol). Triphosgene (0.35 g, 1.13 mmol) was added in one portion. The solution was allowed to warm to 23° C. and stirred for 2 h. The reaction was then diluted with EtOAc, washed with 5% HCl(aq.), half saturated $NaHCO_3$ solution and brine, then dried over $Na_2SO_4$, filtered, and concentrated under reduced pressure. The residue was purified by flash column chromatography to give 115 (1.31 g, 98%).

Step 2:

Using a procedure similar to Example 94, step 2, a mixture of Examples 112 and 113 was prepared. Separation by silica gel chromatography using gradient of hexane to $EtOAc/NEt_3$ 9:1:provided the title compounds.

EXAMPLES 114–115

The following examples were prepared in a similar fashion to Example 103, steps 1–2, omitting step 3 and using the appropriate isocycanate:

EXAMPLES 116–117

The following examples were prepared in a similar fashion to Example 96, using 116 to prepare Example 116 and Example 115 to prepare Example 117 in place of hydroxyureas from Examples 94 and 95:

| Example | R⁵ | MS [M + 1]⁺ |
|---|---|---|
| 114 | ‒C₆H₄‒OMe | 555.1 |
| 115 | 2,6-difluorophenyl | 561.1 |
| 116 | Me | 493.1 |
| 117 | 2,6-difluorophenyl | 591.1 |

EXAMPLES 118–119

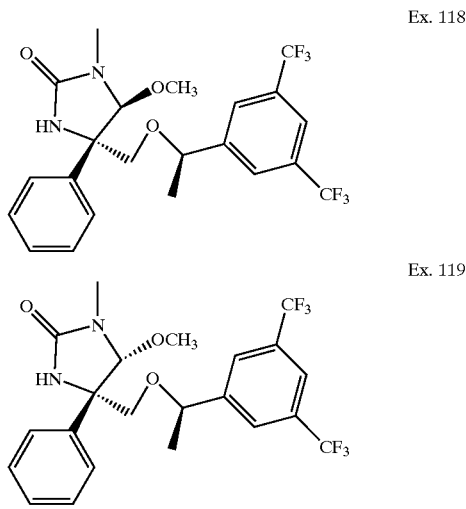

To the alcohol mixture of Examples 112 and 113 was added saturated dry HCl in CH₃OH (5 ml, precooled to −20° C.). The solution was stirred at 23° C. for 2 h, then poured into 10% Na₂CO₃ (25 ml). The aqueous layer was extracted with EtOAc (3×30 ml). The combined organic layer was washed with brine, dried over Na₂SO₄, filtered and concentrated under reduced pressure. Flash chromatography afforded an inseparable mixture of two methyl ethers. The mixture was then separated on HPLC using Chiralpak OD eluted with (95:5) Hexane/iPA. Electrospray MS [M+1]⁺ 477.1

EXAMPLE 120

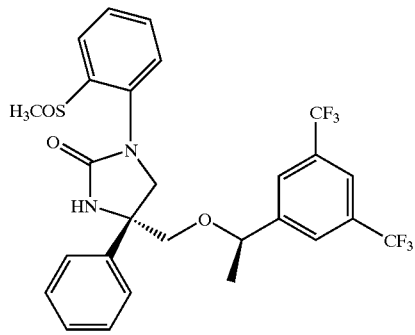

To a solution of Example 103 (170 mg, 0.306 mmol) in CH₂Cl₂ was added solid Oxone (1.14 g, 17.4 mmol), the resulting suspension was stirred vigorously for 20 h, then quenched with saturated NaHCO₃ solution and extracted with EtOAc. The organic layers were washed with brine, dried over Na₂SO₄ and concentrated. Flash chromatography afforded the title compound. Electrospray MS [M+1]⁺ 571.1

EXAMPLE 121

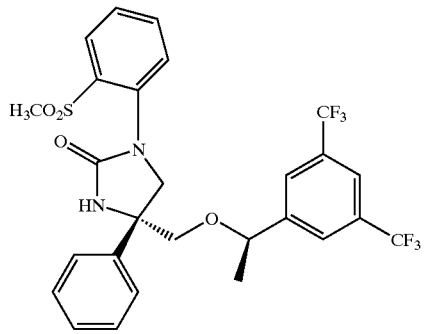

To a solution of Example 120 in $CH_2Cl_2$ was added m-CPBA and the resulting solution was stirred for 30 h, then quenched with $NaHCO_3$ solution and extracted with EtOAc. The organic layers were washed with brine, dried over $Na_2SO_4$ and concentrated. Flash chromatography afforded the title compound. Electrospray MS $[M+1]^+$ 587.1.

EXAMPLE 122

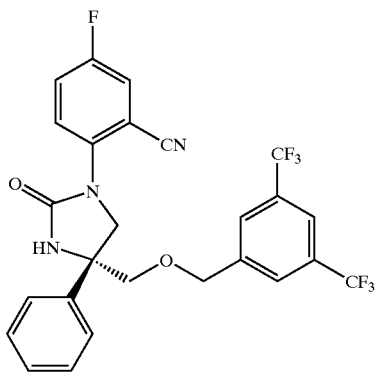

To Example 92 (0.150 g, 0.36 mmol), CsF (0.109 g, 0.72 mmol) in DMF (3.5 ml) at 0° C. and NaH 0.018 g (60% in mineral oil) was added. After stirring for 10 min, 2,5-difluorobenzonitrile (0.0587 g, 0.0378 mmol) was added in small portions. The solution was allowed to warm to 23° C. and was stirred overnight. The reaction was quenched with saturated $NH_4Cl$ solution, extracted with EtOAc, and the combined organic layer was washed with water and brine, dried over $Na_2SO_4$ and concentrated. Flash chromatography afforded the title compound (0.051 g, 26%). Electrospray MS $[M+1]^+$ 538.1.

EXAMPLE 123

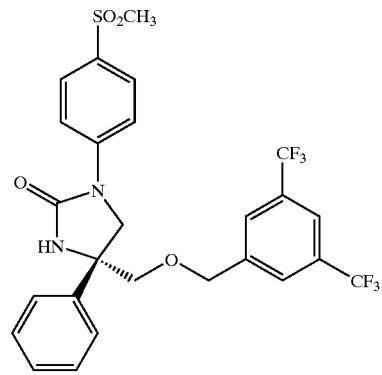

In a procedure similar to Example 122, 4-F-phenylmethylsulfone was used in place of 2,5-difluorobenzonitrile to obtain the title compound. Electrospray MS $[M+1]^+$ 573.1.

EXAMPLE 124

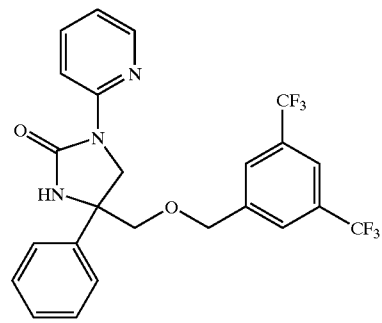

In a procedure similar to Example 122, 2-F-pyridine was used in place of 2,5-difluorobenzonitrile and Example 1 was used in place of Example 92 to obtain the title compound. Electrospray MS $[M+1]^+$ 496.1

EXAMPLE 125

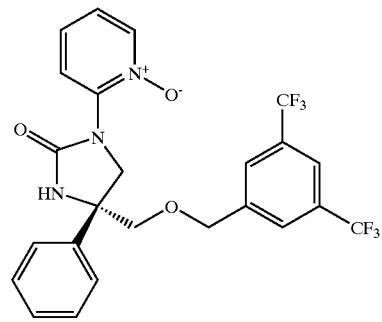

In a procedure similar to Example 122, 2-F-pyridine was used in place of 2,5-difluorobenzonitrile in step 1, followed by a procedure similar to that used in Example 121 for the oxidation to the N-oxide to obtain the title compound. Electrospray MS [M+1]$^+$ 512.1.

EXAMPLE 126–127

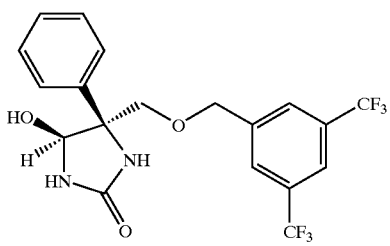
Ex. 126

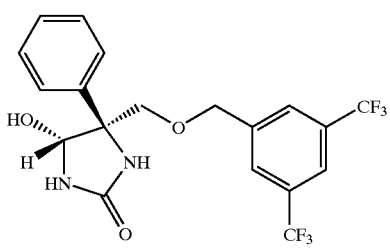
Ex. 127

Step 1:

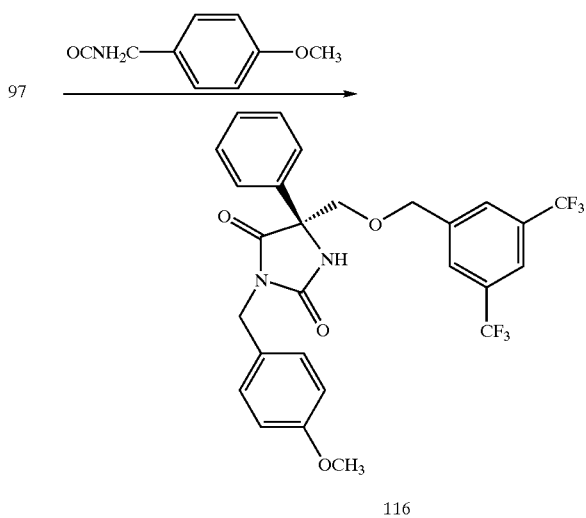

A mixture of hydantoin (prepared from 97 using procedures similar to Example 61, step 6) (5.0 g, 11.6 mmol, 1 equiv.), and p-methoxybenzylisocyanate (2.5 ml, 17.4 mmol, 1.5 equiv.) in dry dioxane (20 ml) was stirred at RT for 3 h, then 3N aqueous HCl (20 ml) was added and the mixture stirred at 90° C. for 14 h. The mixture was poured into 250 ml EtOAc and washed with H$_2$O(2×125 ml). The organic layer was dried over anhydrous Na$_2$SO$_4$, filtered and concentrated to give 6.5 g of the crude racemic 116.

Step 2:

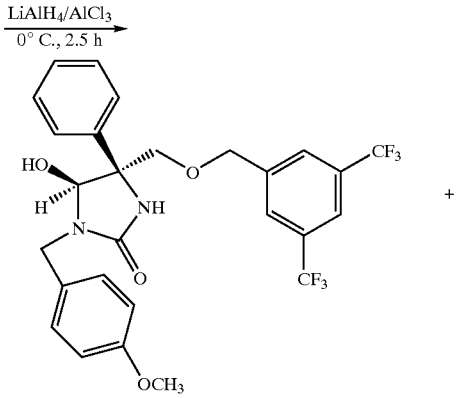

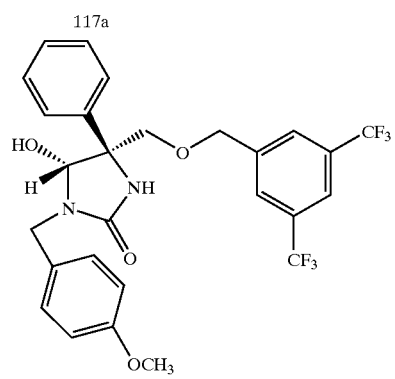

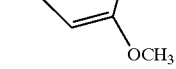

LiAlH$_4$ (35 ml of 1 M solution in ether, 35 mmol, 3 equiv.) was added slowly to AlCl$_3$ (6.3 g, 47.06 mmol, 4 equiv.) at 0° C., and stirred for 10 min, then a solution of 116 (6.5 g, 11.76 mmol, 1 equiv.) in dry THF (70 ml) was carefully added. After stirring at 23° C. for 2.5 h, the mixture was cooled to 0° C., quenched slowly with 30 ml saturated aqueous sodium potassium tartarate and stirred for 14 h at 23° C. The mixture was diluted with water (100 ml), and extracted with EtOAc (2×200 ml). The organic layers were dried over anhydrous Na$_2$SO$_4$, filtered and concentrated. Purification using 400 ml silica and eluting with 2/1 hexane/EtOAc provided 4.62 g of the product as white solid.

Step 3:

To a suspension of 117a/b (4.62 g, 8.33 mmol, 1 equiv.) in CH$_3$CN/water (150 ml, 2:1) at RT was added ceric ammonium nitrate (18.27 g, 33.33 mmol, 4 equiv.). After stirring at 23° C. for 1 h, the mixture was poured into 300 ml EtOAc/150 ml saturated aq. NaHCO$_3$ and filtered through a frit. The organic layer was isolated, the aqueous layer was washed with EtOAc (1×300 ml) and the combined organic layers were dried over anhydrous Na$_2$SO$_4$, filtered and concentrated. Purification using the Biotage silica gel system, eluting with 1/1 hexane/EtOAc, 1 L, followed by 5% CH$_3$OH/EtOAc, 1 L, provided 2.0 g of the product as a mixture of two isomers. HPLC separation on chiralpak AD column, eluting with (90/10) hexane/IPA mixture gave Example 127 FAB, (M$^{+1}$)=435.0, and Example 126, FAB, (M$^{+1}$)=435.0.

EXAMPLES 128–129

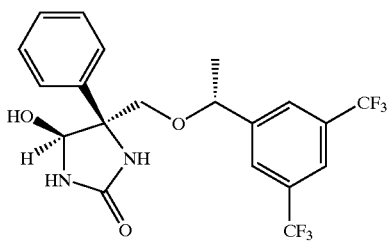
Ex. 128

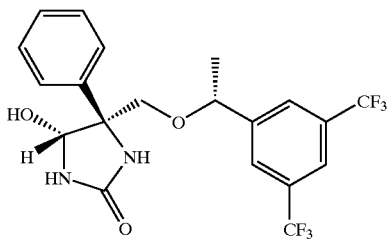
Ex. 129

Step 1:

A mixture of 105 (0.976 g, 2.19 mmol, 1 equiv.), K$_2$CO$_3$ (0.453 g, 3.28 mmol, 1.5 equiv.) in dry DMF (10 ml) was stirred at RT for 30 min. p-Methoxy-benzyl chloride (0.34 ml, 2.5 mmol, 1.15 equiv.) was added at once and the resulting mixture was stirred at 23° C. for 14 h. The mixture was then poured into EtOAc (150 ml) and washed with H$_2$O(3×100 ml) and saturated aq. NaCl (100 ml). The organic layer was dried over Na$_2$SO$_4$, filtered and concentrated to give 1.27 g of the crude product. It was used in the next step without further purification.

Step 2:

The product of step 1 was converted to Examples 128 and 129 using procedures similar to Examples 126 and 127, steps 2–3, using LAH in place of LAH/AlCl$_3$ in step 2 to provide 0.14 g of the products, obtained as mixture of two isomers. HPLC separation on chiralpak AD column using (85/15) hexane/IPA mixture gave 80 mg (29% yield) of Example 129, FAB, (M$^{+1}$) 449.2 and 30 mg (11% yield) of Example 128 FAB, (M$^{+1}$) 449.2.

EXAMPLE 130

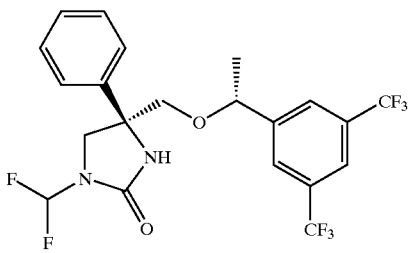

Step 1:

Ex. 93 $\xrightarrow[\text{0° C., to RT}]{\text{POCl}_3, \text{DMF}}$ 68%

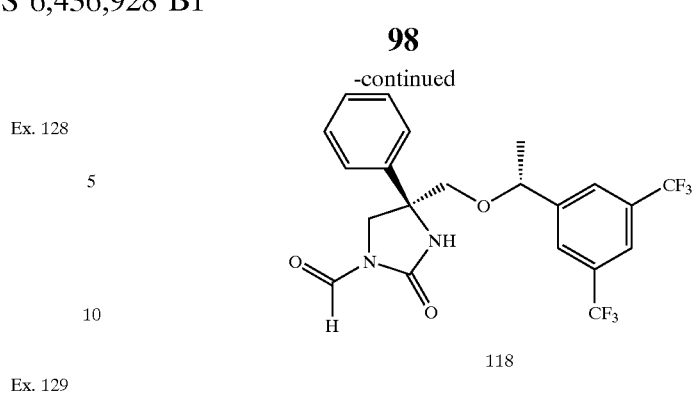
118

To a solution of Example 93 (0.1 g, 0.23 mmol, 1.0 equiv.) in dry DMF (0.5 ml) cooled to 0° C., POCl$_3$ (0.024 ml, 0.254 mmol, 1.1 equiv.) was added slowly. The mixture was warmed to RT, stirred for 30 min, and poured into 5 g ice. The resultant mixture was poured into water (100 ml) and extracted with EtOAc (100 ml). The organic layer was separated, washed with saturated aq. NaCl (1×100 ml), dried over anhydrous Na$_2$SO$_4$ and concentrated. Flash chromatography over 200 ml silica using (1) 4/1 hex/EtOAc, and (2) 1/1 hex/EtOAc gave 0.070 g (66% yield) of 118 as solid. MS (M$^{+1}$) 461.1.

Step 2:

118 $\xrightarrow[\text{toluene, 80° C.}]{\text{Lawesson reagent}}$ 81%

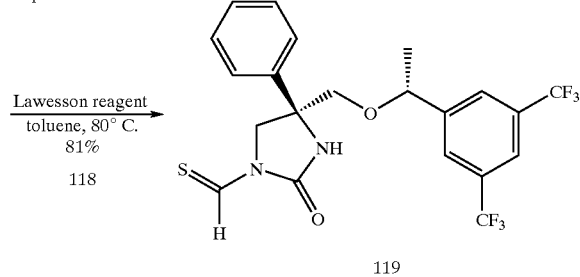
119

118 (0.1 g, 0.22 mmol, 1.0 equiv.) and Lawesson's reagent (0.044 g, 0.108 mmol, 0.5 equiv.) in toluene (1 ml) were heated at 80° C. for 0.5 h. The solvent was evaporated and the residue purified by Biotage chromatography using 15% EtOAc/hexane to obtain 119 as a yellow foam, 0.085 g (81% yield).

Step 3:

119 (0.3 g, 0.626 mmol, 1.0 equiv.) was taken up in CH$_2$Cl$_2$ (3 ml) at RT. DAST (0.17 ml, 1.25 mmol, 2.0 equiv.) was added slowly and the mixture was stirred at RT overnight. The reaction was slowly quenched with saturated aq. NaHCO$_3$ (5 ml), the mixture was poured into saturated aq. NaHCO$_3$ (100 ml) and CH$_2$Cl$_2$ (100 ml) added. The organic layer was separated, dried over anhydrous Na$_2$SO$_4$, filtered and concentrated. The residue was purified by Biotage chromatography using 4/1 hex/EtOAc to obtain the title compound, 0.080 g (27% yield). MS (M$^{+1}$)=483.1.1.

EXAMPLE 131

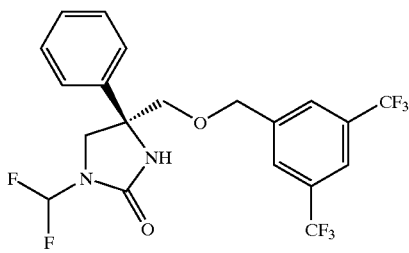

Using procedures similar to Example 130, substituting Example 92 for Example 93, the title compound was prepared. Electrospray MS [M+1]+ 469.1

EXAMPLE 132

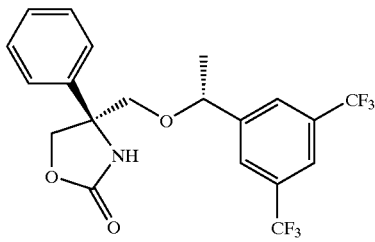

Using procedures similar to those in Example 102, and substituting 97 for 74 in step 1, the title compound was prepared. Electrospray MS [M+1]+ 434.1.

EXAMPLE 133

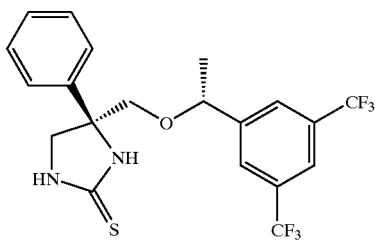

Example 93 (0.633 g, 1.465 mmol, 1.0 equiv.), Lawesson's reagent (0.81 g, 2.04 mmol, 1.37 equiv.) and toluene (12 ml) were heated at 85° C. for 1.5 h, then cooled to RT and concentrated. The residue was purified by silica gel chromatography using 15% EtOAc/hex, then 10% EtOAc/CH$_2$Cl$_2$ to give 0.61 g (93% Yield) of the title compound. MS (M$^{+1}$)=449.1.

EXAMPLE 134

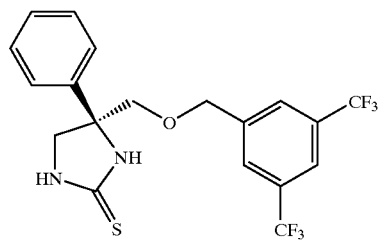

A procedure similar to that used in Example 133, using Example 92 in place of Example 93, provided the title compound. MS (M$^{+1}$)=435.1

EXAMPLES 135–139

The compounds were prepared using procedures similar to those used in Example 99, using Example 92 and the appropriate alkyliodide. For Example 139, Example 76 was used as the starting cyclic urea.

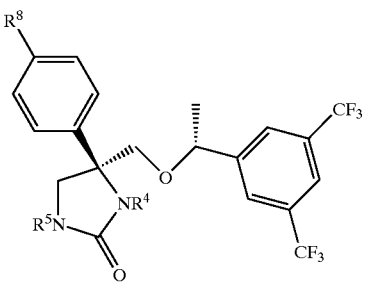

| Example | R$^5$ | R$^4$ | R$^8$ | MS [M + 1]+ |
|---|---|---|---|---|
| 135 | Me | H | H | 447.1 |
| 136 | Et | H | H | 461.1 |
| 137 | H | Et | H | 461.1 |
| 138 | iPr | H | H | 475.1 |
| 139 | Et | H | F | 479.1 |

EXAMPLES 140–141

Ex. 140

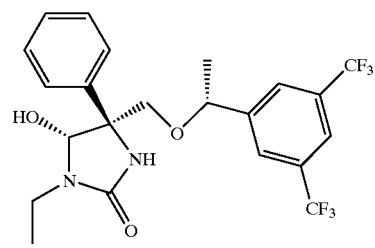

-continued

Ex. 141

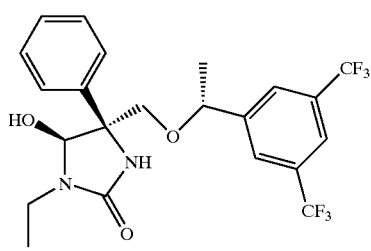

The title compounds were prepared using procedures similar to those in Example 94, using ethyl isocyanate in place of methyl isocyanate. Purification via HPLC (Chirapak AD column using 98/2 hex/isopropanol) provided Example 140 MS [M+1]$^+$ 477.1 and Example 141 MS [M+1]$^+$ 477.1.

EXAMPLE 142

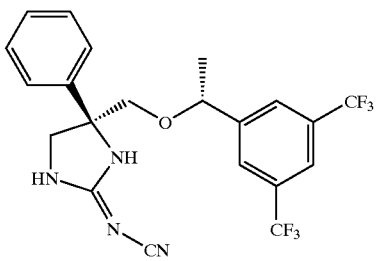

Example 133 (0.61 g, 1.36 mmol, 1.0 equiv.) in THF (20 ml) was treated with CH$_3$I (0.10 ml, 1.36 mmol, 1.2 equiv.), stirred for 14 h, then concentrated. The crude was dissolved in CH$_3$OH (20 ml), treated with NH$_2$CN (0.37 g, 8.84 mmol, 6.7 equiv.) and heated to 60° C. for 14 h. The mixture was concentrated and purified by silica gel chromatography, using 1/1 EtOAc/hex to give the title compound, 0.1 g (17% yield) as a white solid. MS (M$^{+1}$)=457.1.

EXAMPLE 143

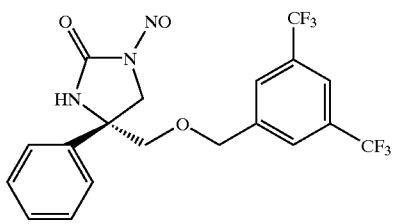

To Example 92 (2.0 g, 4.78 mmol) in THF (15 ml) at 0° C. was added NaNO$_2$ (0.39 g, 5.7 mmol) in H$_2$O (7.5 ml), then H$_2$SO$_4$ (conc.) (1 ml) was added slowly. The solution was allowed to warm to 23° C. and stirred for 1 h. It was then diluted with water and extracted with EtOAc. The organic layers were washed with NaHCO$_3$ solution, brine, dried over Na$_2$SO$_4$ and concentrated to give the title compound. Electrospray MS [M+1]$^+$ 448.1.

EXAMPLE 144

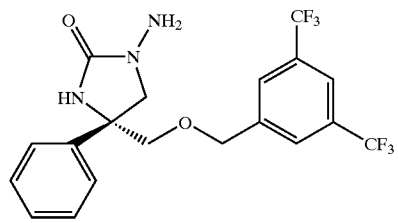

To Example 143 (0.95 g, 2.1 mmol) in Et$_2$O (10 ml) at 0° C. was added dropwise LiAlH$_4$ (4.2 ml, 1M in Et$_2$O). The solution was allowed to warm to 23° C. and stirred for 2 hr. It was quenched with saturated K,Na tartrate solution and then partitioned between water and EtOAc. The aqueous layer was extracted with EtOAc. The combined organic layers were washed with brine, dried over Na$_2$SO$_4$ and concentrated to give the title compound. Electrospray MS [M+1]$^+$ 434.1

EXAMPLE 145

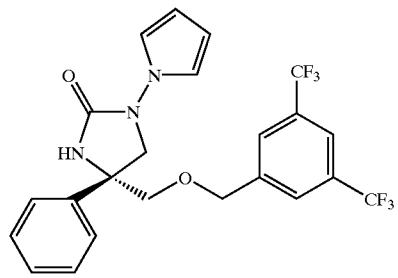

To Example 144 (0.3 g, 0.69 mmol) in acetic acid (3 ml) was added 2,5-dimethoxy-3-tetrohydrofuran (3 ml) and the mixture was heated at 70° C. for 1.5 h. It was cooled to 23° C. and diluted with EtOAc. The organic layers were washed with NaHCO$_3$, brine, dried over Na$_2$SO$_4$ and concentrated. A stream of N$_2$ was introduced into the residue to remove excess 2,5-dimethoxy-3-tetra-hydrofuran. The crude product was purified by silica gel chromatography to give the title compound. Electrospray MS [M+1]$^+$ 484.1.

EXAMPLE 146

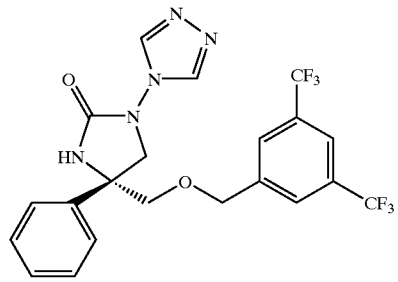

Example 144 (0.65 g, 1.5 mmol) in pyridine (15 ml) was concentrated under reduced pressure at 500° C. using a water bath. The procedure was repeated twice. The residue was treated with 1,2-diformylhydrozine (0.34 g, 3.6 mmol), followed by the addition of pyridine (7.5 ml), Et$_3$N (1.5 ml) and TMSCl (3 ml). The thick paste was heated at 80° C.

under N₂ for 65 h, then concentrated under reduced pressure to give a yellow residue. The residue was partitioned between water and EtOAc. The aqueous layer was extracted with EtOAc. The combined organic layers were washed with brine, dried over Na₂SO₄ and concentrated to give a crude product. Further purification using biotage followed by a prep TLC afforded the title compound. Electrospray MS [M+1]⁺ 486.1.

EXAMPLE 147

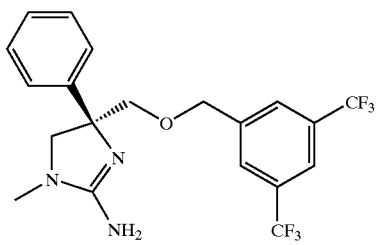

The title compound was prepared in a method analogous to Example 73, using 89 in place of 6. The title compound was obtained in 95% yield. Electrospray MS [M+1]⁺ 432.1.

EXAMPLE 148

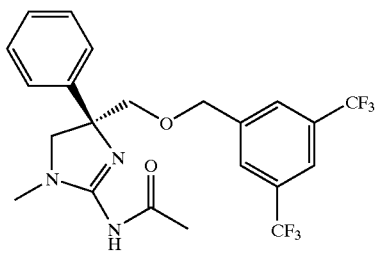

To a cooled solution of Example 147 (0.3 g, 0.70 mmol), DEC (0.14 g, 0.73 mmol), HOBT (0.1 g, 0.74 mmol) and NaSO₄ (0.59 g) in anhydrous CH₂Cl₂ (4.5 ml), glacial acetic acid (0.05 ml, 0.87 mmol) was added followed by Et₃N (0.1 ml, 0.72 mmol). The reaction was allowed to react for 18 h at RT, then quenched with brine. The aqueous solution was extracted with CH₂Cl₂ (50 ml×3). The combined organic layer was dried, filtered and concentrated. The pure title compound was obtained through flash chromatography, eluting with 2% (1:9) NH₄OH—CH₃OH in CH₂Cl₂ to give the final product in 39% yield. Electrospray MS [M+1]⁺ 474.1.

EXAMPLE 149

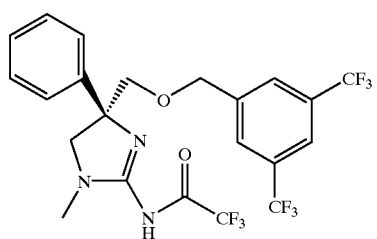

To a cooled solution of Example 147 (0.2 g, 0.46 mmol) in anhydrous CH₂Cl₂ (5 ml) at 0° C., trifluoroacetic anhydride (0.09 ml, 0.64 mmol) neat was added followed by Et₃N (0.08 ml, 0.57 mmol). The reaction was allowed to react for 18 h at RT. Volatile solvents were evaporated. The pure title compound was obtained through flash chromatography, eluting with 50% EtOAc in hexane to give the final product in 33% yield. Electrospray MS [M+1]⁺ 528.1.

EXAMPLE 150

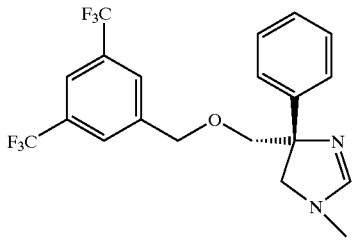

A mixture of 89 (0.38 g, 0.93 mmol) and N,N-dimethylformamide dimethyl acetal (0.11 g, 0.93 mmol) was heated to 60° C. for 18 h. The reaction mixture was purified by chromatography, eluting with 3.5% NH₃—CH₃OH (1:9)/96.5% CH₂Cl₂ to give the title compound later as a HCl salt ( 0.2 g, 50%). FAB MS [M+1] 417.

EXAMPLE 151

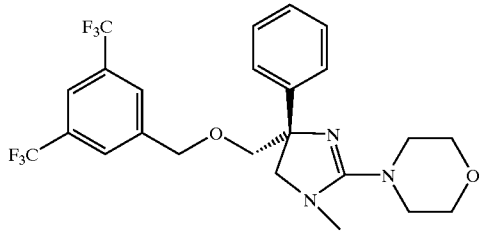

Using a method analogous to Example 82, using morpholine in place of 7 M NH₃ in CH₃OH, the title compound was obtained as a solid in a 36% yield. FAB MS [M+1] 502.

EXAMPLE 152

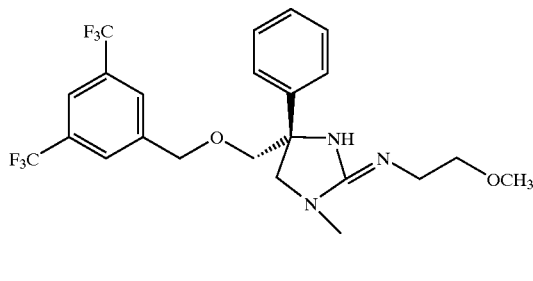

Using a method analogous to that Example 82, using 2-methoxyethyl-amine in place of 7 M NH₃ in CH₃OH, the title compound was obtained as a solid in a 80% yield. FAB MS [M+1] 490.1.

EXAMPLE 153

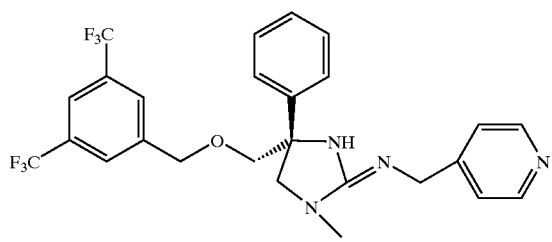

Using a method analogous to Example 82, using 4-(aminomethyl)pyridine in place of 7 M NH₃ in CH₃OH, the title compound was obtained as a solid in a 26% yield. FAB MS [M+1] 523.4.

EXAMPLE 154

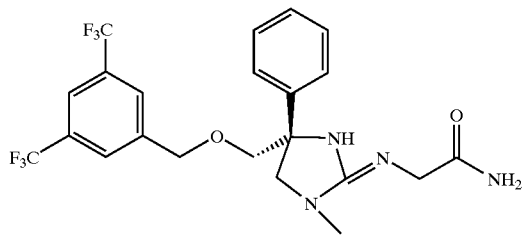

Using a method analogous to Example 82, using glycinamide in place of 7 M NH₃ in CH₃OH, the title compound was obtained as a solid in a 14% yield. FAB MS [M+1] 489.2.

EXAMPLE 155

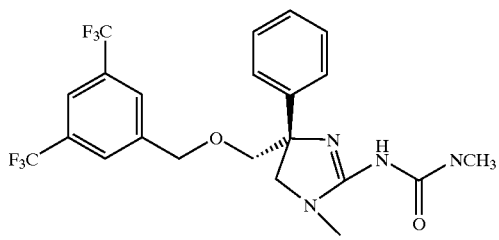

A solution of Example 82 (0.2 g, 0.464 mmol) in CH₂Cl₂ (2 ml) and isocyanate (53 mg, 0.93 mmol was stirred under N₂ at RT for 18 h. After work-up, a solid was obtained as a crude product which was then purified by chromatography, eluting with 2% NH₃—CH₃OH (1:9)/98% CH₂Cl₂ to give the title compound as a solid (55 mg, 24%). FAB MS [M+1] 489.3.

EXAMPLE 156

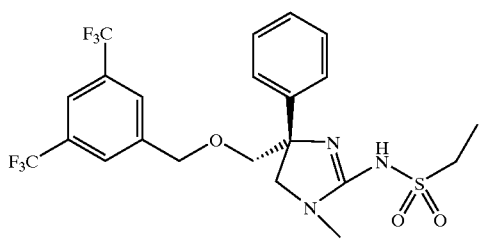

Using a method analogous to Example 155, using ethane sulfonyl chloride in place of isocyanate, the title compound was obtained later as a HCl salt in a 25% yield. FAB MS [M+1] 524.3.

EXAMPLE 157

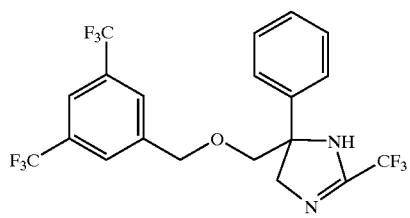

Using a method analogous to Example 87, using 6 in place of 89 and TFA in place of acetic acid, the title compound was later obtained as a HCl salt in a 34% yield. FAB MS [M+1] 471.

EXAMPLE 158

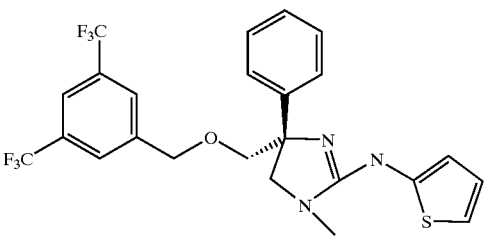

Using a method analogous to Example 89, using 2-thiophene acetic acid in place of acetic acid, the title compound was later obtained as a HCl salt in a 24% yield. FAB MS [M+1] 512.9.

EXAMPLE 159

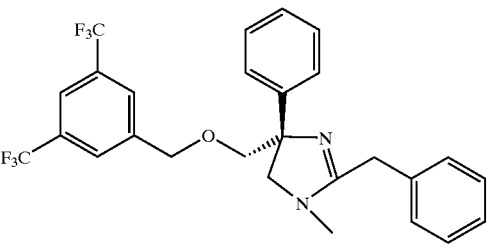

Using a method analogous to Example 89, using phenyl acetic acid in place of acetic acid, the title compound was later obtained as a HCl salt in a 15% yield. FAB MS [M+1] 507.1.

EXAMPLE 160

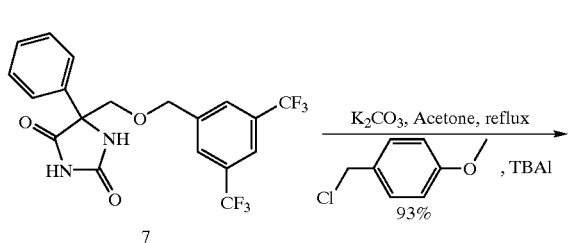
7

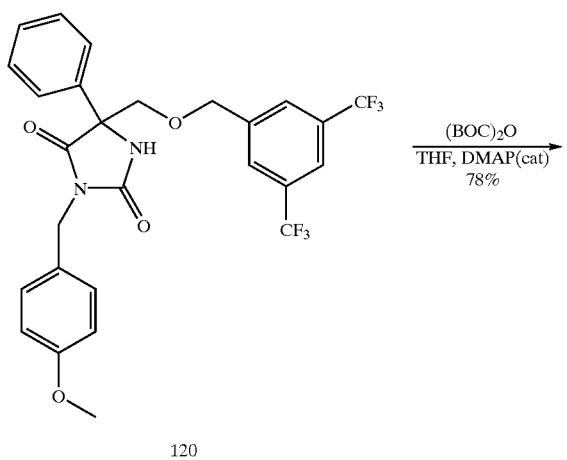
120

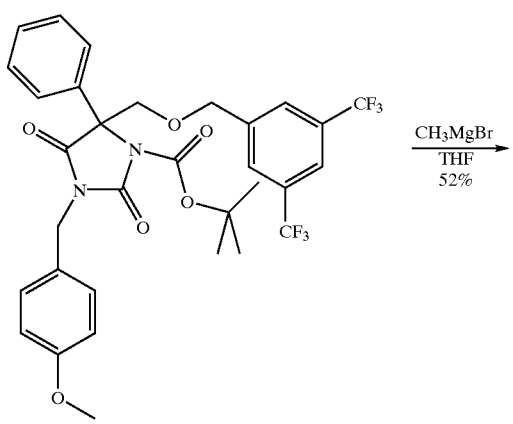
121

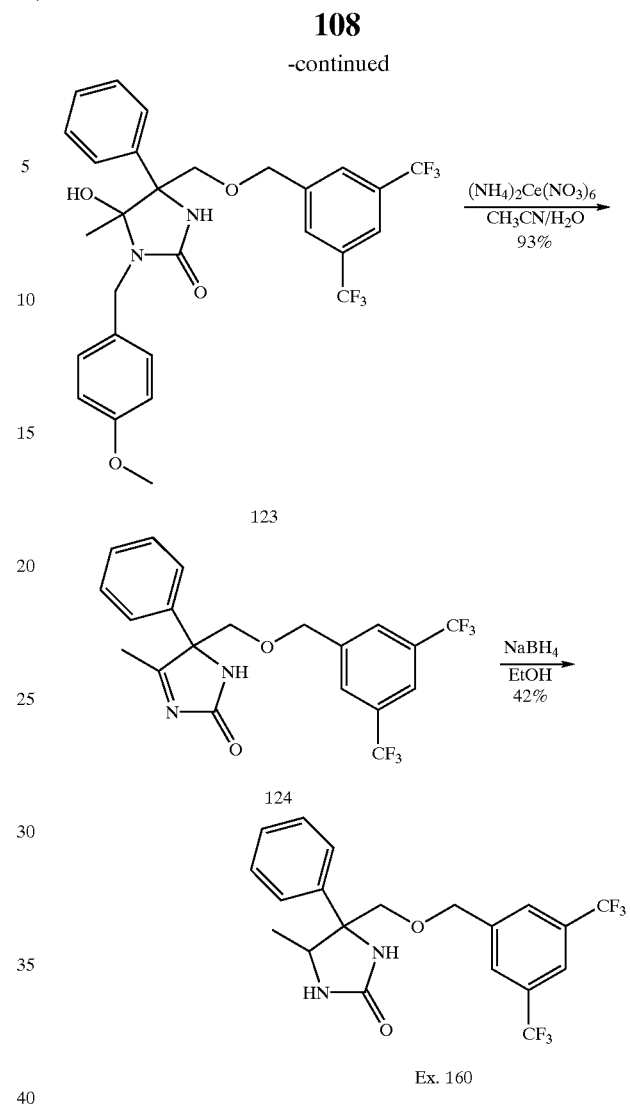
122
123
124
Ex. 160

Step 1 A mixture of hydantoin 7 (9.2 g, 21.3 mmol, 1 equiv.), $k_2CO_3$ (8.8 g, 63.9 mmol, 3.0 equiv.) and tetrabutylammonium iodide (0.79 g, 2.13 mmol, 0.1 equiv.) in 180 mL acetone was stirred at room temperature for 30 minutes, treated with p-methoxybenzyl chloride (3.25 mL, 23.9 mmol, 1.12 equiv.) at reflux for 2 hours, then cooled to room temperature and filtered through sintered glass funnel. The filtrate was concentrated to give pale yellow solid, which was washed with small amount of ice-cold $Et_2O$ (2×5 mL) to give 11 g of the crude racemic p-methoxybenzyl (pmb)-hydantoin 120. It was used in the next step without further purification.

Step 2 A mixture of pmb-hydantoin 120 (6.0 g, 10.9 mmol, 1 equiv.), 4-(dimethylamino)pyridine (DMAP) (0.02 g, 0.16 mmol, 1.5% equiv.) in 60 mL dry THF was stirred at room temperature for 1.5 hours. The solvent was evaporated under vacuum. The residue was taken up in $CH_2Cl_2$ (150 mL) and washed with saturated sodium bicarbonate (50 mL). The organic layer was dried over anhydrous $Na_2SO_4$, then concentrated. The crude was purified with Biotage (EtOAc/Hexane=10%) to give 5.5 g (77.7% yield) of BOC-pmb-hydantoin 121 as white solid.

Step 3 A solution of BOC-pmb-hydantoin 121 (540 mg, 0.83 mmol, 1 equiv.) in 10 mL dry THF was treated with 3.0

M methylmagnesium bromide Et$_2$O solution (0.42 mL, 1.25 mmol, 1.5 equiv.) at 0° C. After addition, the reaction was warmed up to room temperature gradually and stirred for another hour. THF was evaporated under vacuum. The residue was taken up with 100 mL CH$_2$Cl$_2$, then washed with 10 mL of saturated aq. NaHCO$_3$ solution. The resulting white solid was filtered off. The filtrate was concentrated and purified by Biotage (EtOAc/Hexane=20%) to give 290 mg(52.3% yield) of Methyl-hydroxy-BOC-pmb-urea 122 as white solid.

Step 4 A solution of methyl-hydroxy-BOC-pmb-urea 122 (310 mg, 0.46 mmol, 1 equiv.) in 5 mL of dry CH$_2$Cl$_2$ was treated with 1.16 mL of 4.0 M HCl in 1,4-dioxane at 0° C. The reaction was allowed to warm up to room temperature and stirred overnight. The crude product was taken up with Et$_2$O, then washed with 3 mL of saturated NaHCO$_3$. The aqueous layer was further extracted with ether. The combined organic layer was dried over Na$_2$SO$_4$, then concentrated, and purified with Biotage (EtOAc/Hexane= 15%) to give 150 mg (56.5% yield) of Methyl-hydroxy-pmb-urea 123 as white solid.

Step 5 A white suspension of Methyl-hydroxy-pmb-urea 123 (1 g, 1.76 mmol, 1 equiv.) in 22.5 mL of CH$_3$CN and 6.75 mL of water was treated with ceric ammonium nitrate (7.72 g, 14.0 mmol, 8 equiv.). Stirred at room temperature for 8 hours, then partitioned between 300 mL of EtOAc and 100 mL of saturated aq. NaHCO$_3$. The yellow solid was filtered off and aqueous layer was further extracted with 2×100 mL EtOAc. Combined organic layers were dried over anhy. Na$_2$SO$_4$, filtered and concentrated. Flashed over Biotage (EtOAc/Hexane/Et$_3$N=1:1:2%) to give 703 mg (93% yield) of 124 as white solid.

Step 6 A solution of 124 (312 mg, 93 mmol, 1 equiv.) in 8 mL EtOH was reacted with NaBH$_4$ (600 mg, 15.9 mmol, 17 equiv.) at room temperature for 2 days. The crude was partitioned between 2×100 mL of CH$_2$Cl$_2$ and 100 mL saturated aq. NaHCO$_3$, then washed with 80 mL of Brine. The combined organic layer was dried over anhy. Na$_2$SO$_4$, filtered, concentrated to give 300 mg of liquid as crude. It was purified with Biotage (EtOAc/Hexane=30%) to give two diastereomers (100 mg and 70 mg each), which were separated on HPLC with a ChiralCel OD column to give the 4 stereoisomers of example 160. MS: (M+1)=433.

EXAMPLE 161

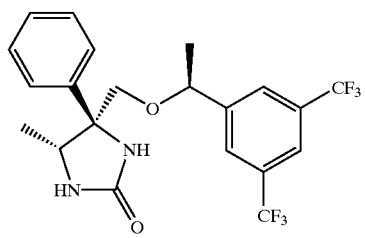

Example 161a

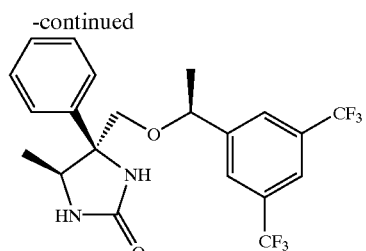

Example 161b

Examples 161a and 161b were synthesized using procedure similar to example 160 starting from optical pure hydantoin 105. MS: (M+1)=447.

EXAMPLES 162–164

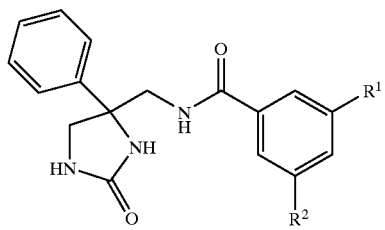

| Example | R$^1$ | R$^2$ | MS [M + 1]$^+$ |
|---------|-------|-------|----------------|
| 162 | F | CF$_3$ | 382.1 |
| 163 | Cl | Cl | 364.1 |
| 164 | CF$_3$ | CF$_3$ | 432.1 |

The title compounds were prepared using the acylation procedure similar to those used in example 21 using amine 39 and the appropriate substituted benzoyl chloride to provide the title benzamides.

EXAMPLE 165

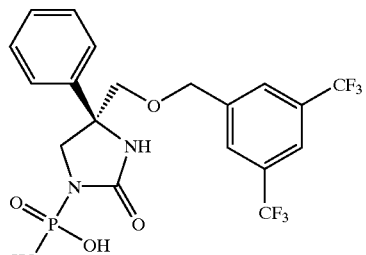

• 2 N-methylglucamine
Example 165a

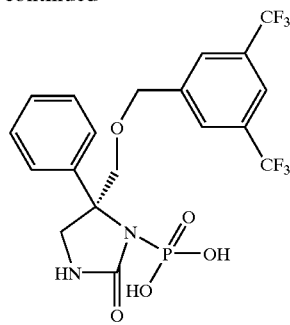

• 2 N-methylglucamine
Example 165b

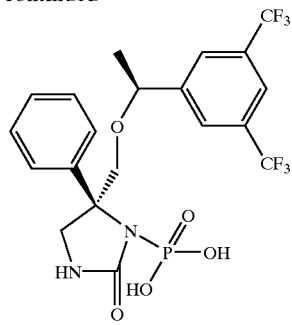

• 2 N-methylglucamine
Example 166b

Step 1

A solution of Example 92 (224 mg, 0.536 mmol, 1 equiv.) in THF (12 mL) at 0° C. was treated with 2.5 M n-BuLi (215 µL, 0.536 mmol, 1 equiv.). The resulting mixture was stirred cold for 5 min. Tetrabutyl pyrophosphate (405 mg, 0.751 mmol, 1.4 equiv.) was added to the reaction mixture as a solid in one portion. The cooling bath was removed and the reaction was stirred at room temperature for 45 minutes at which point a white suspension formed. The reaction was quenched with sat. aq. NaHCO$_3$ (20 mL) and extracted with EtOAc (2×30 mL). The solution was dried (Na$_2$SO$_4$), filtered, and concentrated to give crude product (461 mg). This was not purified and used crude in the next step.

Step 2

A solution of the product of step 1 (364 mg, 0.536 mmol, 1 equiv.) in MeOH (10 mL), a solution of N-Me-D-glucamine (206 mg, 1.072 mmol, 2 equiv.) in H$_2$O (2 mL), and 10% Pd/C (29 mg) were combined and the mixture was hydrogenated at 40 psi for 2 h. The reaction mixture was filtered through a pad of Celite and rinsed with MeOH (80 mL). The solution was concentrated under reduced pressure and the crude product redissolved in MeOH (5 mL)__. $^i$PrOH (25 mL) was added to the solution and the resulting mixture was aged at room temperature for 30 min to form a white precipitate. The precipitate was filtered, washed with PrOH (15 mL) and EtOAc (15 mL), and dried. The solid was partitioned between EtOAc (30 mL) and H$_2$O (30 mL) and an emulsion formed. The emulsion was transferred in 10–12 mL portions to centrifuge tubes and centrifuged at 3000 rpm for 15 min. Decanted away the organic layer. The aqueous layers were combined, filtered, and lyophilized to provide example 165 (306 mg, 64% yield, 1:1 mixture of regioisomers 165a and 165b).

EXAMPLE 166

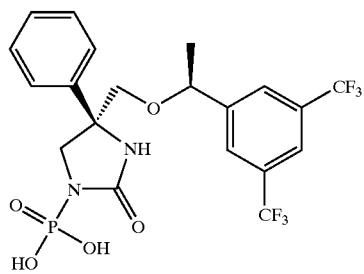

• 2 N-methylglucamine
Example 166a

Using procedures similar to those in example 165 and substituting Example 93 for Example 92, the title compounds were prepared.

Compounds of formula I have been found to be antagonists of the NK$_1$ receptor and of the effect of Substance P at its receptor site, and are therefore useful in treating conditions caused or aggravated by the activity of said receptor.

The in vitro and in vivo activity of the compounds of formula I can be determined by various procedures known in the art, such as a test for their ability to inhibit the activity of the NK$_1$ agonist Substance P. % Inhibition of neurokinin agonist activity is the difference between the percent of maximum specific binding (MSB) and 100%. The percent of MSB is defined by the following equation, wherein "dpm" is disintegrations per minute:

$$\% \ MSB = \frac{(dpm \ \text{of unknown}) - (dpm \ \text{of nonspecific binding})}{(dpm \ \text{of total binding}) - (dpm \ \text{of nonspecific binding})} \times 100$$

The concentration at which the compound produces 50% inhibition of binding is then used to determine the inhibition constant (ki) using the Chang-Prusoff equation.

In addition, functional antagonism of calcium channel activity is measured using FLIPR technology known to those skilled in the art.

In vivo activity is measured by inhibition of agonist-induced foot tapping in the gerbil, as described in Science, (1998), 281, p.1640–1695.

It will be recognized that compounds of formula I exhibit NK$_1$ antagonist activity to varying degrees, e.g., certain compounds have strong NK$_1$ antagonist activity, while others are weaker NK$_1$ antagonists.

Compounds of the present invention exhibit a range of activity: Ki values range from about 0.1 to 1000 nM, with Ki values of about 0.1 to 100 being preferred and Ki values of 0.1 to 25 nM being more preferred. Most preferred are compounds having a Ki≦110 nM for the NK$_1$ receptor.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18 th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of $NK_1$ receptor antagonists in combination with selective serotonin reuptake inhibitors in a unit dose of preparation may be varied or adjusted from about 10 mg to about 300 mg of $NK_1$ receptor antagonists with about 10 mg to about 100 mg of SSRI. A further quantity of $NK_1$ receptor antagonists in combination with selective serotonin reuptake inhibitors in a unit dose of preparation may be varied or adjusted from about 50 mg to about 300 mg of $NK_1$ receptor antagonists with about 10 mg to about 100 mg of SSRI. An even further quantity of $NK_1$ receptor antagonists in combination with selective serotonin reuptake inhibitors in a unit dose of preparation may be varied or adjusted from about 50 mg to about 300 mg of $NK_1$ receptor antagonists with about 20 mg of SSRI, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

While the present has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound represented by the structural formula

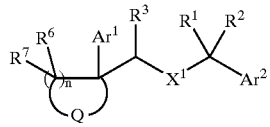

I or a pharmaceutically acceptable salt thereof, wherein
$Ar^1$ and $Ar^2$ are independently selected from the group consisting of

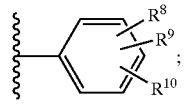

$X^1$ is —O—, —$NR^{12}$—, —$N(COR^{12})$— or —$N(SO_2)R^{15}$—;

$R^1$, $R^2$, $R^3$ and $R^7$ are each independently selected from the group consisting of H, $C_1$–$C_6$ alkyl, hydroxy $(C_1$–$C_3)$alkyl, $C_3$–$C_6$ cycloalkyl, —$CH_2F$, —$CHF_2$ and —$CF_3$; or $R^1$ and $R^2$, together with the carbon to which they are attached, form a $C_3$–$C_6$ alkylene ring;

each $R^6$ is independently selected from H, $C_1$–$C_6$ alkyl, —$OR^{13}$ or —$SR^{12}$;

n is 1;

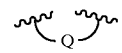

is

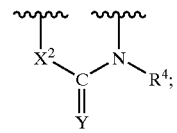

$X^2$ is —$NR^5$—;
Y is =O;
$R^5$ is H or —$(CH_2)_{n1}$—G, wherein $n_1$ is 0–5, G is H, —$CF_3$, —$CHF_2$, —$CH_2F$, —OH, —O—$(C_1$–$C_6$ alkyl), —$SO_2R^{13}$, —O—$(C_3$–$C_8$ cycloalkyl), —$NR^{13}R^{14}$, —$SO_2NR^{13}R^{14}$, —$NR^{13}SO_2R^{15}$, —$NR^{13}COR^{12}$, —$NR^{12}(CONR^{13}R^{14})$, —$CONR^{13}R^{14}$, —$COOR^{12}$, $C_3$–$C_8$ cycloalkyl, $R^{19}$-aryl,

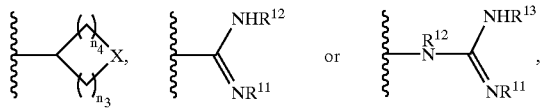

or when $n_1$ is 0, $R^5$ can also be —$C(O)R^{13}$ or —$C(S)R^{13}$; provided that G is not H when $n_1$=0;

X is —$CF_2$—, —$CH_2$— or —$CR^{12}F$—;

$R^8$, $R^9$ and $R^{10}$ are independently selected from the group consisting of H, $C_1$–$C_6$ alkyl, $C_3$–$C_8$ cycloalkyl, —$OR^{12}$, halogen, —CN, —$NO_2$, —$CF_3$, —$CHF_2$, —$CH_2F$, —$OCF_3$, —$OCHF_2$, —$OCH_2F$, —$COOR^{12}$, —$CONR^{21}R^{22}$, —NR²¹COR¹², —NR²¹CO₂R¹⁵, —NR²¹CONR²¹R²², —NR²¹SO₂R¹⁵, —NR²¹R²², —SOO₂NR²¹R²², —S(O)$_{n5}$R¹⁵, R¹⁶-aryl and R¹⁹-heteroaryl;

R¹¹ is H, C₁–C₆ alkyl, C₃–C₈ cycloalkyl, —NO₂, —CN, OH, —OR¹², —O(CH₂)$_{n6}$R¹², —(C₁–C₃) alkyl-C(O)NHR¹², R¹⁹-aryl(CH₂)$_{n6}$— or R¹⁹-heteroaryl-(CH₂)$_{n6}$—;

R⁴ and R¹² are each independently selected from the group consisting of H, C₁–C₆ alkyl and C₃–C₈ cycloalkyl;

R¹³ and R¹⁴ are independently selected from the group consisting of H, C₁–C₆ alkyl, C₃–C₈ cycloalkyl, or R¹⁹-aryl(CH₂)$_{n6}$—;

R¹⁵ is C₃–C₆ alkyl, C₃–C₈ cycloalkyl or —CF₃;

R¹⁶ is 1 to 3 substituents independently selected from the group consisting of H, C₁–C₆ alkyl, C₃–C₈ cycloalkyl, C₁–C₆ alkoxy, halogen and —CF₃;

R¹⁹ is 1 to 3 substituents independently selected from the group consisting of H, C₁–C₆ alkyl, C₃–C₈ cycloalkyl, —OH, halogen, —CN, —NO₂, —CF₃, —CHF₂, —CH₂F, —OCF₃, —OCHF₂, —OCH₂F, —O—(C₁–C₆ alkyl), —O—(C₃–C₈ cycloalkyl), —COOR¹², —CONR²¹R²², —NR²¹R²², —NR²¹COR¹², —NR²¹CO₂R¹², —NR²¹CONR²¹R²², —NR²¹SO₂R¹⁵ and —S(O)$_{n5}$R¹⁵;

R²¹ and R²² are independently selected from the group consisting of H, C₁–C₆ alkyl, C₃–C₈ cycloalkyl and benzyl;

n₃ and n₄ are independently 1–5, provided that the sum of n₃ and n₄ is 2–6;

n₅ is independently 0–2; and n₆ is independently 0–3;

wherein heteroaryl means a 5- to 10-membered single or benzofused aromatic ring comprising 1 to 4 heteroatoms independently selected from the group consisting of —O—, —S—, —N= and —NH—, provided that the rings do not include adjacent oxygen and/or sulfur atoms.

2. The compound of claim 1 wherein R¹, R³, R⁴ and R⁷ are each hydrogen.

3. The compound of claim 1 wherein R⁶ is H or OH.

4. The compound of claim 1 wherein X¹ is —O— or —NR¹²—.

5. The compound of claim 1 selected from the group of compounds represented by the formula

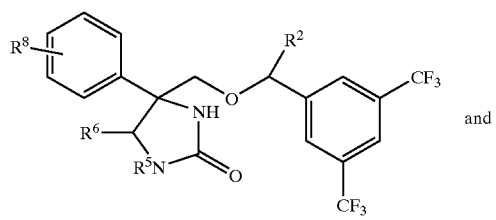

and

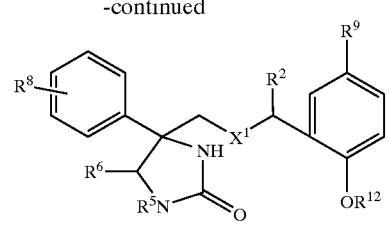

wherein R⁸ is H or halogen; R² is H, —CH₃ or —CH₂OH; R⁶ is H or —OH; and R⁵ is selected from the group consisting of hydrogen and groups of the formula —(CH₂)$_{n1}$—G.

6. The compound of claim 5 wherein X¹ is —O—, —NH—, —N(CH₃)— or —N(COCH₃); R⁸ is H or halogen; R² is H, —CH₃ or —CH₂OH; R⁶ is H or —OH; R⁹ is —OCF₃ or 5-(trifluoromethyl)-1H-tetrazol-1-yl; R¹² is —CH₃ or cyclopropyl; and R⁵ is selected from the group consisting of hydrogen and groups of the formula —(CH₂)$_{n1}$—G, wherein —(CH₂)$_{n1}$—G is selected from the group consisting of

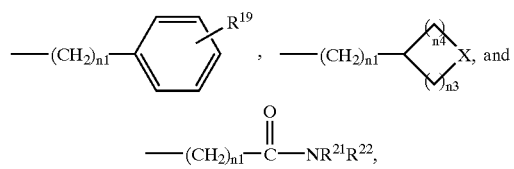

and —(CH₂)$_{n1}$—G', wherein n1 is 2–4 and G' is H, —OH, —OCH₃—, ethoxy, isopropyloxy, —O-cyclopropyl, or —CONR¹³R¹⁴, wherein R¹³ and R¹⁴ are independently selected from the group consisting of H, —CH₃, ethyl, isopropyl, or cyclopropyl.

7. The compound of claim 1 wherein said compound is

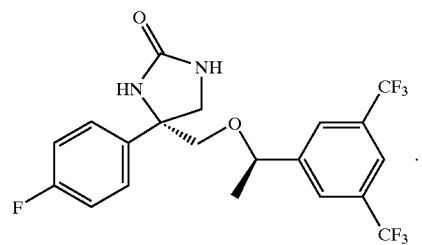

8. The compound of claim 1 wherein said compound is

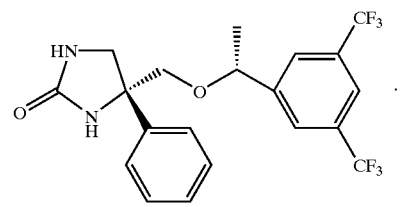

9. The compound of claim 1 wherein said compound is

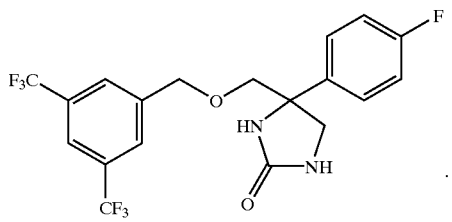

10. The compound of claim 1 wherein said compound is

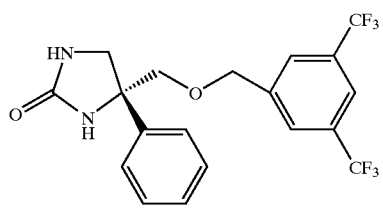

11. The compound of claim 1 wherein said compound is

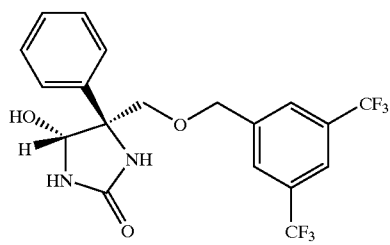

12. The compound of claim 1 wherein said compound is

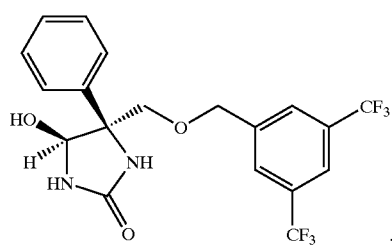

13. The compound of claim 1 wherein said compound is

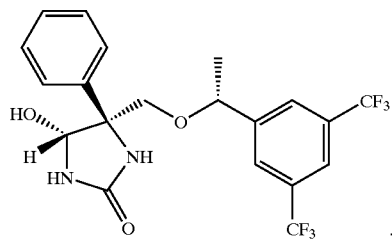

14. The compound of claim 1 wherein said compound is

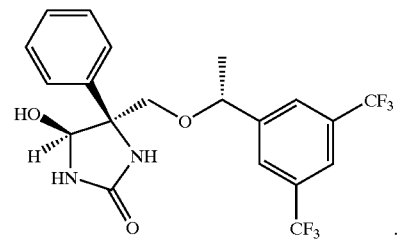

15. The compound of claim 1 wherein said compound is

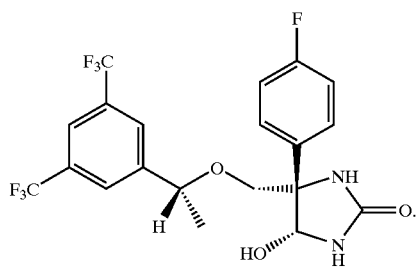

16. The compound of claim 1 wherein said compound is

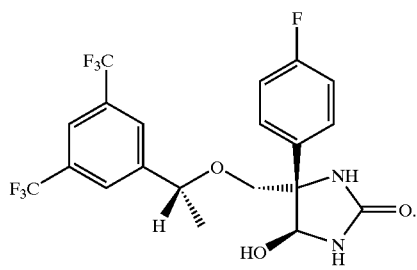

17. A pharmaceutical composition comprising an effective amount of the compound of claim 1 and a pharmaceutically acceptable carrier.

18. The pharmaceutical composition of claim 17 wherein the compound is selected from the group consisting of

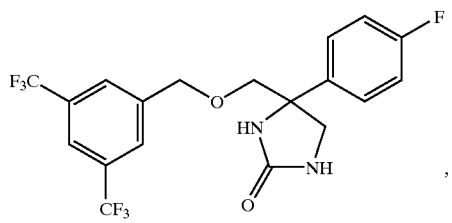

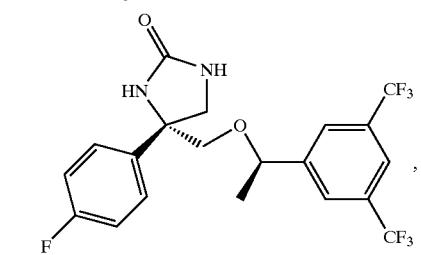

-continued

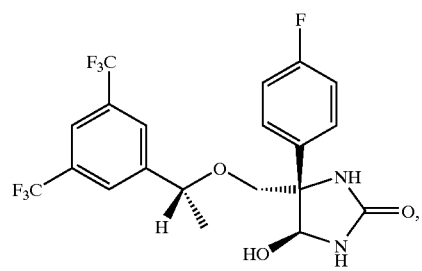

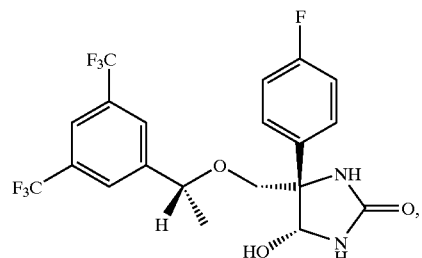

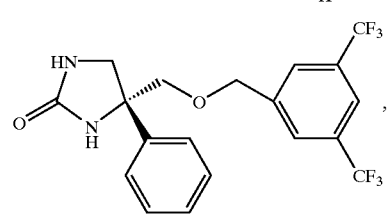

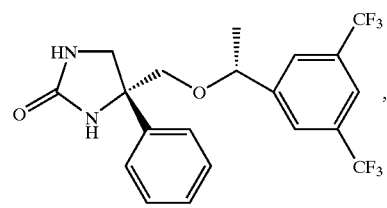

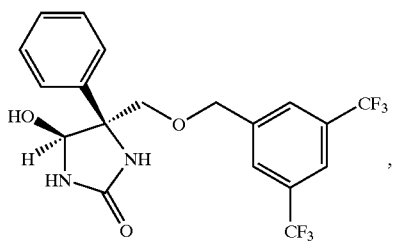

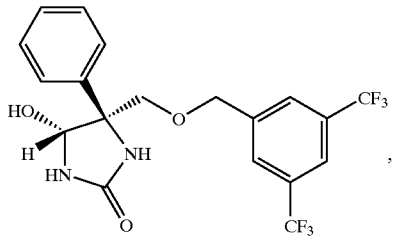

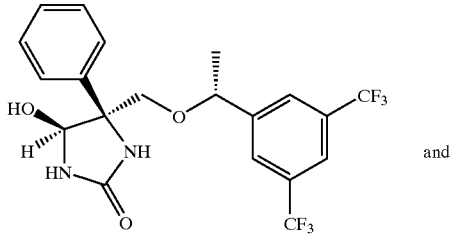 and

-continued

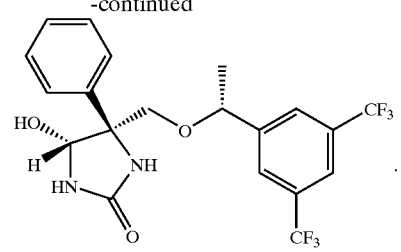

19. A method of treating respiratory diseases; inflammatory diseases; stress related disorders; obsessive/compulsive disorders; mania; anxiety; depression; emesis; migraine; obesity; or pain related disorders comprising administering to a patient in need of such treatment an effective amount of a compound of claim 1.

20. The method of claim 19 wherein the compound used is selected from the group consisting of

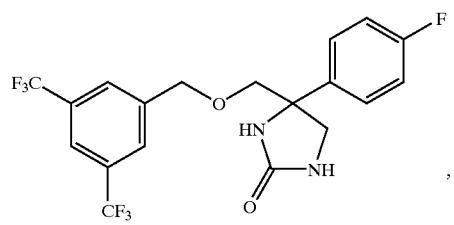

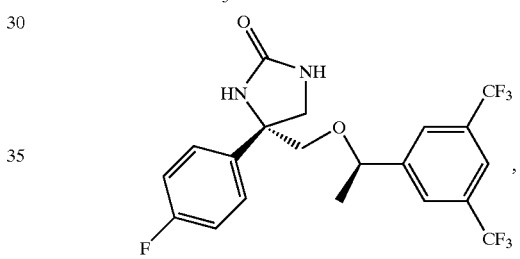

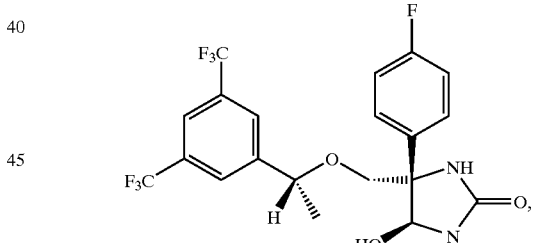

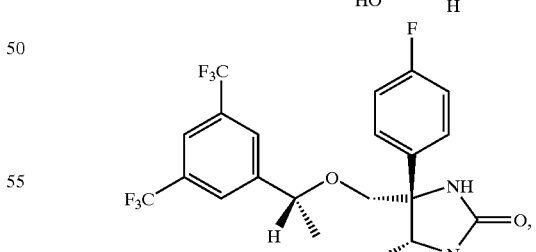

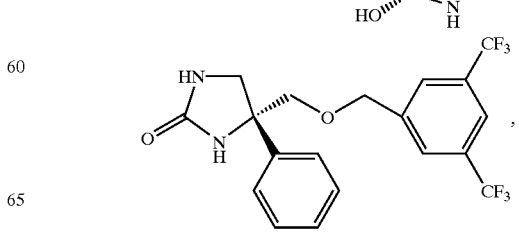

121
-continued
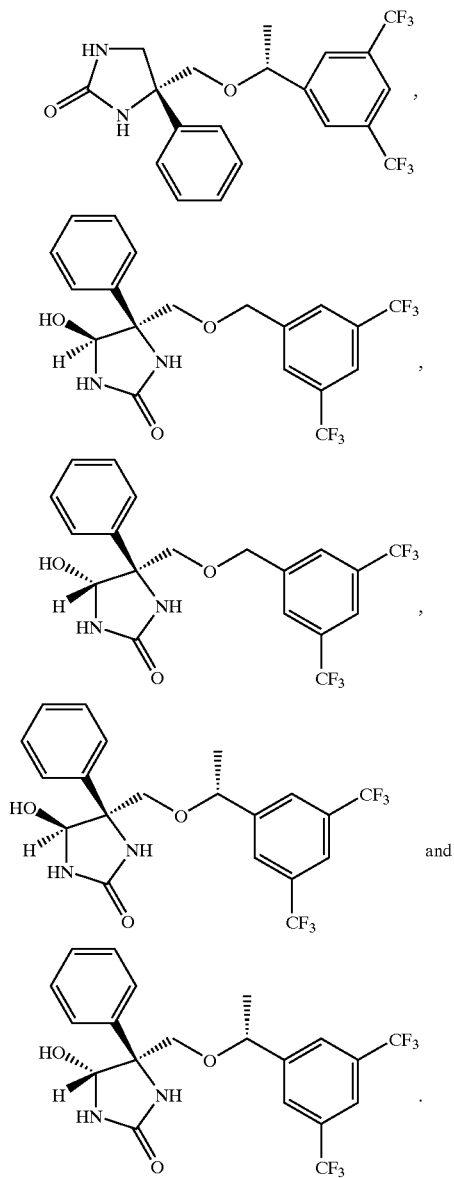
122
-continued
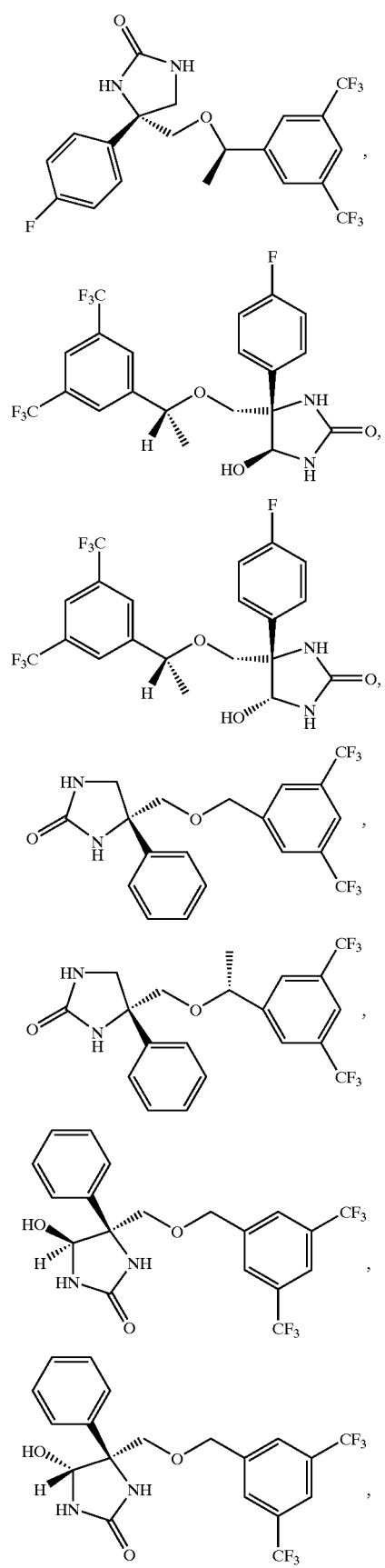
21. A method of treating emesis, depression, anxiety, mania, obesity or cough comprising administering to a patient in need of such treatment an effective amount of a compound of claim 1.
22. The method of claim 21 wherein the compound used is selected from the group consisting of
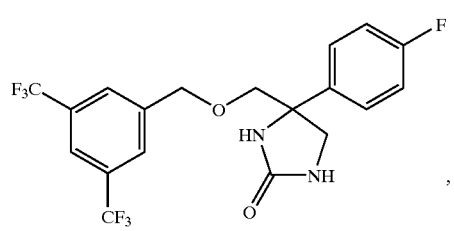

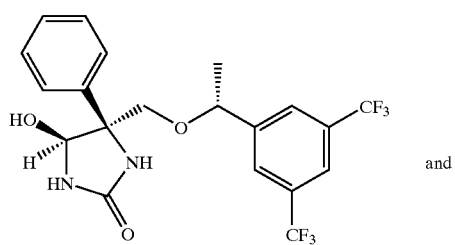
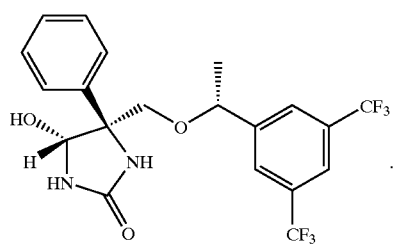 and
23. The compound of claim 1 selected from the group consisting of
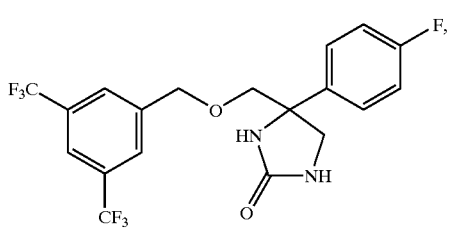
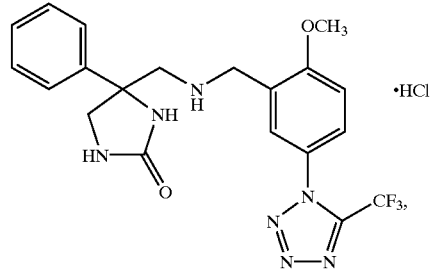
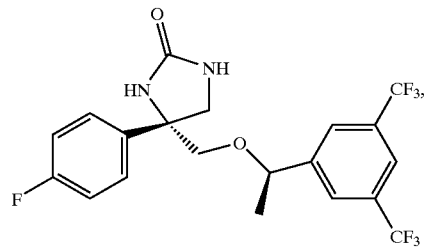
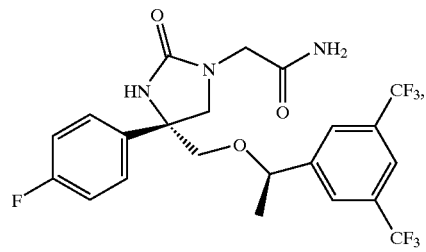
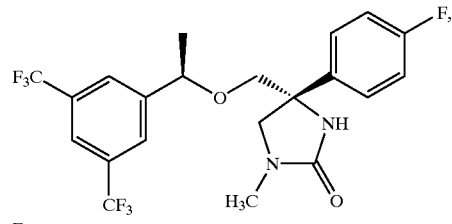
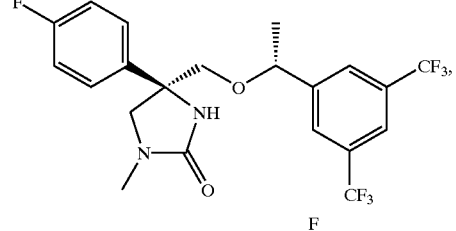
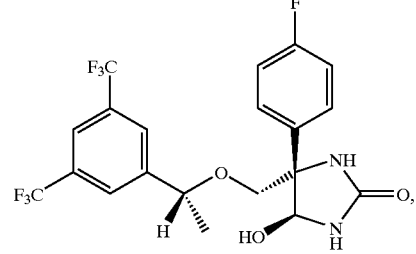
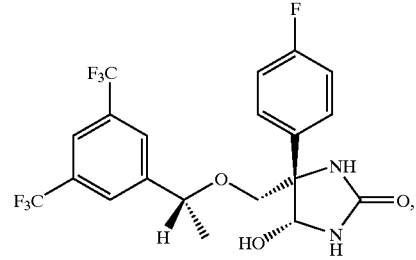
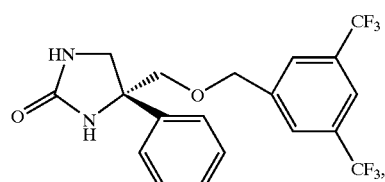
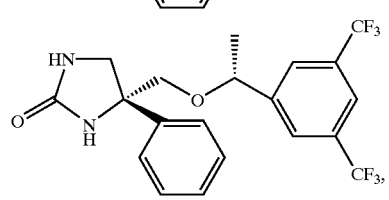
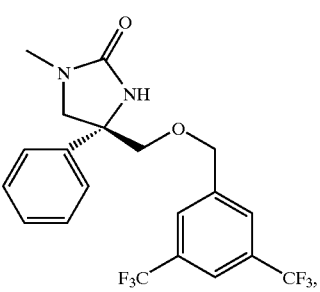

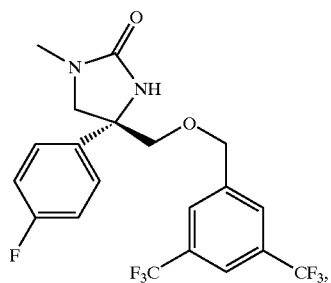
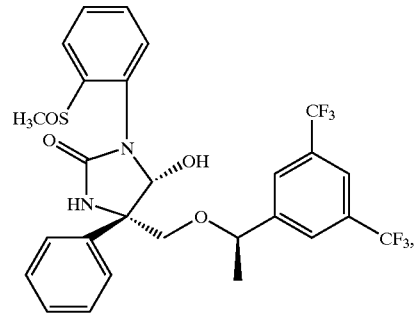
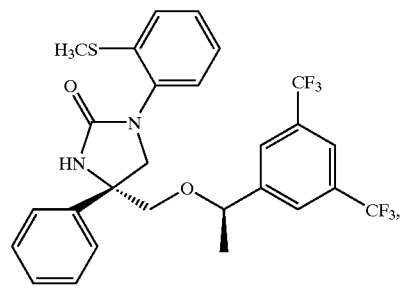
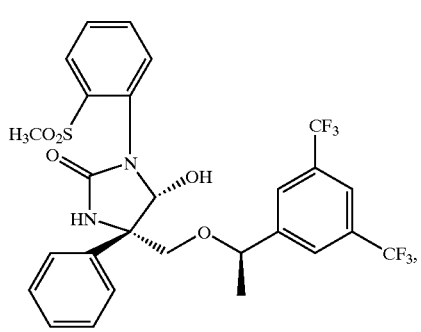
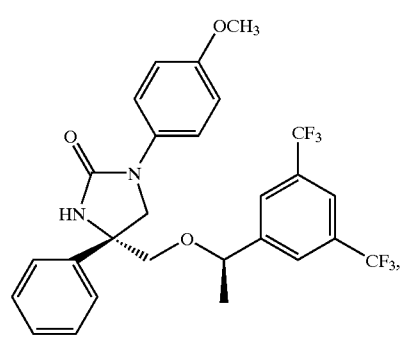
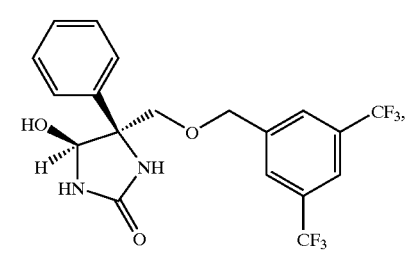
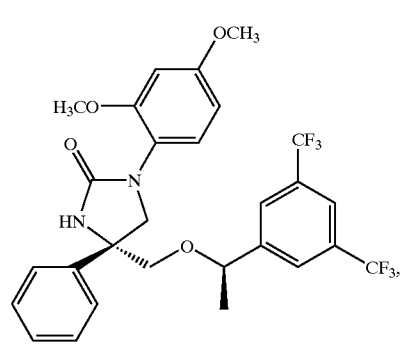
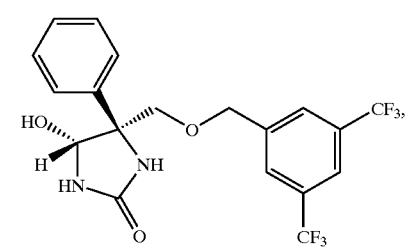
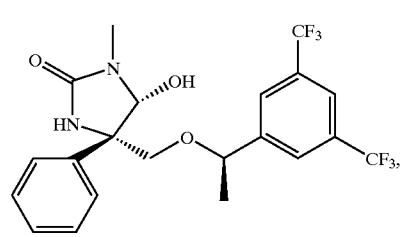
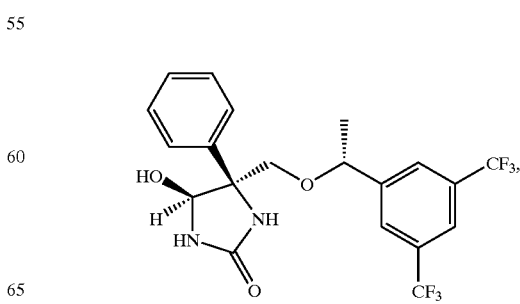

127
-continued
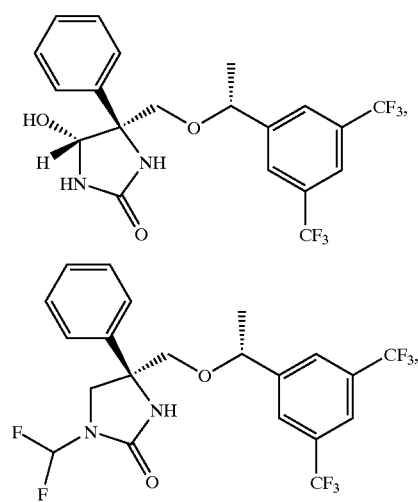
128
-continued
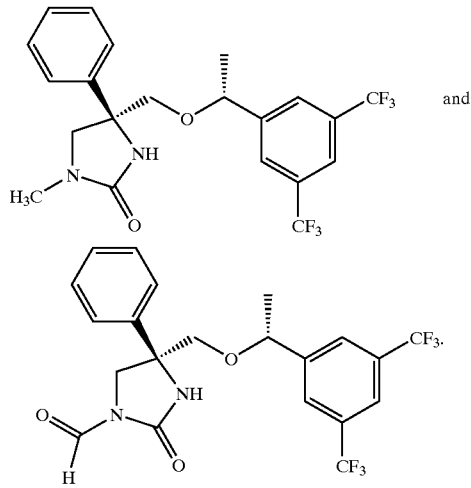
and
* * * * *

UNITED STATES PATENT AND TRADEMARK OFFICE
CERTIFICATE OF CORRECTION

PATENT NO. : 6,436,928 B1
DATED : August 20 2002
INVENTOR(S) : Neng-Yang Shih et al.

It is certified that error appears in the above-identified patent and that said Letters Patent is hereby corrected as shown below:

Column 115,
Line 3, please change "-SOO2NR21R22" to -- SO2NR21R22 --.

Signed and Sealed this

Twenty-second Day of June, 2004

JON W. DUDAS
*Acting Director of the United States Patent and Trademark Office*